(12) United States Patent
Tada et al.

(10) Patent No.: US 10,603,653 B2
(45) Date of Patent: Mar. 31, 2020

(54) SUPER ABSORBENT POLYACRYLIC ACID (SALT)-BASED RESIN POWDER, METHOD FOR MANUFACTURING SAME, AND METHOD FOR EVALUATING SAME

(71) Applicant: NIPPON SHOKUBAI CO., LTD., Osaka-shi, Osaka (JP)

(72) Inventors: Kenji Tada, Hyogo (JP); Kazushi Torii, Hyogo (JP)

(73) Assignee: NIPPON SHOKUBAI CO., LTD., Osaka-shi, Osaka (JP)

( * ) Notice: Subject to any disclaimer, the term of this patent is extended or adjusted under 35 U.S.C. 154(b) by 24 days.

(21) Appl. No.: 15/562,169

(22) PCT Filed: Mar. 29, 2016

(86) PCT No.: PCT/JP2016/060175
§ 371 (c)(1),
(2) Date: Sep. 27, 2017

(87) PCT Pub. No.: WO2016/158975
PCT Pub. Date: Oct. 6, 2016

(65) Prior Publication Data
US 2018/0185820 A1    Jul. 5, 2018

(30) Foreign Application Priority Data

Mar. 31, 2015   (JP) .................................. 2015-074180
Sep. 30, 2015   (JP) .................................. 2015-193458
Oct. 2, 2015    (JP) .................................. 2015-197077

(51) Int. Cl.
*B01J 20/26*   (2006.01)
*C08L 33/02*   (2006.01)
(Continued)

(52) U.S. Cl.
CPC .......... *B01J 20/267* (2013.01); *B01J 20/043* (2013.01); *B01J 20/103* (2013.01);
(Continued)

(58) Field of Classification Search
CPC ..... C08J 3/12; C08J 3/075; C08J 3/245; C08J 2331/02; C08L 33/02; C08F 20/04;
(Continued)

(56) References Cited

U.S. PATENT DOCUMENTS 9,533,433 B2 *   1/2017   Torii ........................ B29B 9/06
2004/0068057 A1  4/2004   Kim
(Continued)

FOREIGN PATENT DOCUMENTS

CN    103059327 A    4/2013
EP      2565211 A1   3/2013
(Continued)

OTHER PUBLICATIONS

European Search Report from European Application No. 16772856.7 dated Oct. 26, 2018 (9 pages).
(Continued)

*Primary Examiner* — Angela C Scott
(74) *Attorney, Agent, or Firm* — Harness Dickey & Pierce P.L.C.

(57) ABSTRACT

The present invention provides polyacrylic acid (salt)-based water-absorbing resin powder having an excellent fluid retention capacity under pressure, an excellent water absorption speed, and an excellent liquid permeability and a method for producing the polyacrylic acid (salt)-based water-absorbing resin powder. The earlier-described objects are attained by: a method for producing water-absorbing resin powder which includes adding an inorganic compound to a crosslinked hydrogel polymer obtained in a polymerization step of polymerizing a polyacrylic acid (salt) and
(Continued)

performing crushing in specific gel-crushing conditions; and the resultant water-absorbing resin powder.

4 Claims, 3 Drawing Sheets

(51) Int. Cl.
| C08K 3/00 | (2018.01) |
| C08J 3/12 | (2006.01) |
| B01J 20/04 | (2006.01) |
| B01J 20/10 | (2006.01) |
| B01J 20/28 | (2006.01) |
| B01J 20/30 | (2006.01) |
| C08F 20/04 | (2006.01) |
| C08J 3/24 | (2006.01) |
| G01N 15/02 | (2006.01) |
| C08J 3/075 | (2006.01) |

(52) U.S. Cl.
CPC ... *B01J 20/28016* (2013.01); *B01J 20/28047* (2013.01); *B01J 20/3021* (2013.01); *B01J 20/3085* (2013.01); *C08F 20/04* (2013.01); *C08J 3/12* (2013.01); *C08J 3/245* (2013.01); *C08K 3/00* (2013.01); *C08L 33/02* (2013.01); *G01N 15/0255* (2013.01); *C08F 2810/20* (2013.01); *C08J 3/075* (2013.01); *C08J 2331/02* (2013.01)

(58) Field of Classification Search
CPC .............. C08F 2810/20; B01J 20/3085; B01J 20/28047; B01J 20/28016; B01J 20/267; B01J 20/103; B01J 20/043; B01J 20/3021; C08K 3/00; G01N 15/0255
USPC ........................................................ 524/430
See application file for complete search history.

(56) References Cited

U.S. PATENT DOCUMENTS

| 2006/0247351 | A1 | 11/2006 | Torii et al. |
| 2006/0282052 | A1 | 12/2006 | Saito et al. |
| 2011/0001087 | A1 | 1/2011 | Hillebrecht et al. |
| 2011/0118430 | A1 | 5/2011 | Funk et al. |
| 2011/0313113 | A1 | 12/2011 | Sakamoto et al. |
| 2012/0258851 | A1 | 10/2012 | Nakatsuru et al. |
| 2013/0026412 | A1 | 1/2013 | Machida et al. |
| 2013/0101851 | A1 | 4/2013 | Takaai et al. |
| 2013/0102750 | A1 | 4/2013 | Watanabe et al. |
| 2014/0296465 | A1 | 10/2014 | Sakamoto et al. |
| 2015/0011388 | A1 | 1/2015 | Matsumoto et al. |
| 2015/0259494 | A1 | 9/2015 | Takaai et al. |
| 2016/0199529 | A1 | 7/2016 | Torii et al. |
| 2016/0207226 | A1 | 7/2016 | Torii et al. |
| 2016/0332141 | A1 | 11/2016 | Machida et al. |

FOREIGN PATENT DOCUMENTS

| JP | 2001/213914 A | 8/2001 |
| JP | 2004/517179 A | 6/2004 |
| JP | 2005/097569 A | 4/2005 |
| JP | 2009/203383 A | 9/2009 |
| JP | 2011/513543 A | 4/2011 |
| JP | 2011/528050 A | 11/2011 |
| WO | WO-2006/098271 A1 | 9/2006 |
| WO | WO-2011/126079 A1 | 10/2011 |
| WO | WO-2011/136301 A1 | 11/2011 |
| WO | WO-2015/030129 A1 | 3/2015 |
| WO | WO-2015/030130 A1 | 3/2015 |

OTHER PUBLICATIONS

English Translation of International Preliminary Report on Patentability dated Oct. 3, 2017 issued in International Patent Application No. PCT/JP2016/060175.
International Search Report Issued in International Patent Application No. PCT/JP2016/060175, dated May 31, 2016.

* cited by examiner

SUPER ABSORBENT POLYACRYLIC ACID (SALT)-BASED RESIN POWDER, METHOD FOR MANUFACTURING SAME, AND METHOD FOR EVALUATING SAME

PRIORITY STATEMENT

This patent application is a U.S. national stage filing under 35 U.S.C. § 371 of International Application No. PCT/JP2016/060175 filed 29 Mar. 2016, which claims priority to Japanese Patent Application No. 2015-074180 filed on 31 Mar. 2015, Japanese Patent Application No. 2015-193458 filed 20 Sep. 2015, and Japanese Patent Application No. 2015-197077 filed 2 Oct. 2015. The entire disclosures of each of the above recited applications are incorporated herein by reference.

TECHNICAL FIELD

The present invention relates to polyacrylic acid (salt)-based water-absorbing resin powder, a method for producing the polyacrylic acid (salt)-based water-absorbing resin powder, and an evaluation method for evaluating the polyacrylic acid (salt)-based water-absorbing resin powder. In regard to the evaluation method, the present invention relates to a method for evaluating the degree of collapse of swollen gel particles when the polyacrylic acid (salt)-based water-absorbing resin powder swells to become the swollen gel particles.

BACKGROUND ART

A water-absorbing resin (SAP/Super Absorbent Polymer) is a water-swellable, water-insoluble polymer gelling agent, and is often used for absorbents such as sanitary materials including disposable diapers and sanitary napkins, agricultural and horticultural water retaining agents, and industrial water blocking materials.

Such water-absorbing resins are produced using a variety of monomers or hydrophilic polymers as raw materials. Of these, a polyacrylic acid (salt)-based water-absorbing resin produced using acrylic acid and/or salt thereof as monomer is most commonly produced industrially because of its high water absorption performance.

The water-absorbing resin is produced through a polymerization step, a gel-crushing step, and a drying step, and optionally, through a pulverizing step, a classification step, a surface-crosslinking step, and/or the like. As disposable diapers, which are major applications of the water-absorbing resin, grow in performance, the water-absorbing resin is also required to have various functions (physical properties). Specific examples of such physical properties include not only high fluid retention capacity but also high gel strength, low water-soluble content, high water absorption speed, high fluid retention capacity under pressure, high liquid permeability, small particle size distribution, urine resistance, antibacterial property, impact resistance (damage resistance), powder fluidity, deodorizing property, coloration resistance (whiteness), and low dust generation.

Of the physical properties listed above, liquid permeability and water absorption speed are important as basic physical properties of the water-absorbing resin, and many improvement techniques have been proposed. However, since high liquid permeability and high water absorption speed are the physical properties in a trade-off relationship, there has been a demand for a technique to achieve both high liquid permeability and high water absorption speed.

One such technique to achieve both high liquid permeability and high water absorption speed has been proposed, by which a crosslinked hydrogel polymer obtained through a polymerization step is crushed in specific gel-crushing conditions to obtain a water-absorbing resin having an excellent liquid permeability and an excellent water absorption speed (refer to Patent Literature 1).

It is noted that techniques to improve physical properties of a water-absorbing resin have been proposed, by which various additives are added in a polymerization step, a gel-crushing step, a granulation step, and/or the like (refer to Patent Literatures 2 to 9).

Furthermore, in regard to measurement of swollen water-absorbing resin particles (i.e., gel particles), methods of measuring the weight average particle diameter (D50) and the particle size distribution of a particulate hydrogel resulting from gel-crushing are disclosed (Patent Literature 1, Patent Literatures 10 and 11).

CITATION LIST

Patent Literature

[Patent Literature 1]
Pamphlet of International Publication No. WO 2011/126079
[Patent Literature 2]
Japanese Patent Application Publication Tokukai No. 2005-097569
[Patent Literature 3]
Japanese Patent Application Publication Tokukai No. 2001-213914
[Patent Literature 4]
Japanese Translation of PCT Patent Application Publication, Tokuhyo, No. 2011-528050
[Patent Literature 5]
Japanese Translation of PCT Patent Application Publication, Tokuhyo, No. 2011-513543
[Patent Literature 6]
Japanese Patent Application Publication Tokukai No. 2009-203383
[Patent Literature 7]
Japanese Translation of PCT Patent Application Publication, Tokuhyo, No. 2004-517179
[Patent Literature 8]
Pamphlet of International Publication No. WO 06/098271
[Patent Literature 9]
Chinese Patent Application Publication No. 103059327
[Patent Literature 10]
Pamphlet of International Publication No. WO 2015/030129
[Patent Literature 11]
Pamphlet of International Publication No. WO 2015/030130

SUMMARY OF INVENTION

Technical Problem

However, the method disclosed in Patent Literature 1, by which a crosslinked hydrogel polymer is crushed in specific gel-crushing conditions to obtain a water-absorbing resin having an excellent liquid permeability and an excellent water absorption speed, has a problem in that the resulting water-absorbing resin powder has insufficient fluid retention capacity under pressure.

It is an object of the present invention to solve the above problem of an existing technique and provide: water-absorbing resin powder that undergoes little collapse when swelling into gel and that has an excellent fluid retention capacity under pressure, an excellent water absorption speed, and an excellent liquid permeability; and a method for producing the water-absorbing resin powder.

In a case where water-absorbing resin powder is used as an absorbent body of an absorbent article such as a disposable diaper and the water-absorbing resin powder is to absorb liquid such as urine, the water-absorbing resin powder is normally caused to absorb the liquid more than once. Therefore, if it was possible to find and evaluate a factor that influences the water absorption performance of swollen gel particles when a water-absorbing resin absorbs liquid and swells to become the gel particles, it would be possible to make a more advanced product design of the water-absorbing resin.

The already proposed methods for measurement of gel particles are to measure gel particles generated in a polymerization step of polymerizing a water-absorbing resin or in a gel-crushing step subsequent to the polymerization step. There has been no report on a technique of measuring swollen gel particles when water-absorbing resin powder, which is produced through a drying step and, optionally, a pulverizing step, a classification step, a surface-crosslinking step, and/or the like, has absorbed liquid and swollen to become the swollen gel particles.

It is another object of the present invention to provide a novel method for evaluating swollen gel particles when water-absorbing resin powder has absorbed liquid and swollen to become the swollen gel particles, in order to make a more advanced product design of a water-absorbing resin.

Solution to Problem

In order to attain the above objects, the inventors of the present invention studied hard and found that, by adding an inorganic compound and/or water-absorbing resin fine particles to a crosslinked hydrogel polymer obtained in a polymerization step of polymerizing polyacrylic acid (salt) and by performing crushing in specific gel-crushing conditions, it is possible to obtain water-absorbing resin powder that has an excellent fluid retention capacity under pressure, an excellent water absorption speed, and an excellent liquid permeability and that undergoes less collapse when swelling into gel. On the basis of this finding, the inventors accomplished the present invention.

Specifically, in order to attain the above object, polyacrylic acid (salt)-based water-absorbing resin powder in accordance with an aspect of the present invention contains a polyacrylic acid (salt) as a main component, the polyacrylic acid (salt)-based water-absorbing resin powder satisfying the following physical properties (1) to (4):

(1) a water absorption time according to a vortex method (Vortex) is 42 seconds or less or a free swell rate (FSR) is 0.28 g/(g·s) or more;

(2) a percentage of water-absorbing resin powder having a particle size of 150 μm or more and less than 850 μm is 90 weight % or more;

(3) a gel particle's collapse rate at swelling is 10 weight % or less;

(4) an internal gas bubble ratio defined by the following equation is 0.1% to 2.5%:

Internal gas bubble ratio (%)=(true density−apparent density)/true density×100.

In order to attain the above object, a method for producing polyacrylic acid (salt)-based water-absorbing resin powder in accordance with another aspect of the present invention includes a polymerization step of polymerizing an acrylic acid (salt)-based aqueous monomer solution, a gel-crushing step of crushing a crosslinked hydrogel polymer during or after polymerization, and a drying step performed after gel-crushing, where an inorganic compound and/or water-absorbing resin fine particles is/are added in the gel-crushing step to the crosslinked hydrogel polymer having a resin solid content of 10 weight % or more and 80 weight % or less, and after gel-crushing which satisfies at least one of the following (1) and (2) is performed:

(1) a gel grinding energy (GGE) is 18 J/g to 60 J/g; and (2) a gel grinding energy (2) (GGE (2)) is 9 J/g to 40 J/g, a particulate crosslinked hydrogel polymer obtained from the gel-crushing step is dried using a dryer at a drying temperature of 150° C. to 250° C. in the drying step.

In order to attain the above objects, the inventors of the present invention studied hard and found that the degree of collapse of swollen gel particles, when the water-absorbing resin powder has swollen to become the swollen gel particles, significantly influences the performance of a water-absorbing resin at water absorption, and found a method for evaluating the degree of collapse of swollen gel particles when the water-absorbing resin powder has swollen to become the swollen gel particles. On the basis of this finding, the inventors accomplished the present invention.

Specifically, in order to attain the above object, a method for evaluating polyacrylic acid (salt)-based water-absorbing resin powder in accordance with a further aspect of the present invention is a method for evaluating a gel particle's collapse rate at swelling of water-absorbing resin powder including:

(procedure 1) classifying water-absorbing resin powder having a moisture content of 10 weight % or less with use of two or more sieves having different mesh sizes;

(procedure 2) allowing all or part of the water-absorbing resin powder to swell with a sweller liquid to become swollen gel particles;

(procedure 3) further classifying the swollen gel particles with use of two or more sieves having different mesh sizes and finding a cumulative percentage of swollen gel particles that pass through each of the two or more sieves;

(procedure 4) calculating a swelling capacity from a weight or a volume of the all or part of the water-absorbing resin powder subjected to the procedure 2 and a weight or a volume of the swollen gel particles obtained in the procedure 3;

(procedure 5) on the basis of the swelling capacity, converting the mesh sizes of the two or more sieves used in the procedure 1 into respective mesh sizes of sieves for use in the procedure 3 or converting the mesh sizes of the two or more sieves used in the procedure 3 into respective mesh sizes of sieves for use in the procedure 1; and (procedure 6) finding a rate of collapse of the swollen gel particles from a plot of the mesh sizes of the two or more sieves obtained by conversion in the procedure 5 and the cumulative percentage of the swollen gel particles that pass through each of the two or more sieves obtained in the procedure 3.

Advantageous Effects of Invention

The polyacrylic acid (salt)-based water-absorbing resin powder in accordance with an aspect of the present invention is arranged as described above. Such water-absorbing resin powder brings about the effect of being excellent as an absorbent body of an absorbent article such as a disposable diaper. That is, this aspect of the present invention brings about an effect such that the water-absorbing resin powder which has excellent physical properties, such as a low gel particle's collapse rate at swelling, also has an excellent shape retention capacity when swollen to become the gel particles. Therefore, in a case where the water-absorbing resin powder is used as an absorbent body of an absorbent article such as a disposable diaper, it gives improved comfort to skin of a wearer of the absorbent article.

The method for producing polyacrylic acid (salt)-based water-absorbing resin powder in accordance with another aspect of the present invention is arranged such that, as described above, in a gel-crushing step, an inorganic compound and/or water-absorbing resin fine particles is/are added to a crosslinked hydrogel polymer and crushing is performed. Water-absorbing resin powder obtained by such a production method brings about the effect of being excellent as an absorbent body in an absorbent article such as a disposable diaper.

The method of another aspect of the present invention makes it possible to evaluate the degree of collapse of swollen gel particles when water-absorbing resin powder has swollen to become the swollen gel particles. Therefore, according to the method of another aspect of the present invention, for example, it is possible to predict to what degree the particle size distribution of the unswollen water-absorbing resin powder would change due to the collapse after liquid absorption and swelling. Therefore, the method of another aspect of the present invention makes it possible to make a more advanced product design of a water-absorbing resin.

When a water-absorbing resin absorbs water, its water absorption performance such as liquid permeability and water absorption speed is closely related to the degree of collapse of swollen gel particles. For example, in a case where the degree of collapse of swollen gel particles is high, the surface area of the swollen gel particles increases, resulting in a water-absorbing resin having a high water absorption speed. On the other hand, in a case where the degree of collapse of swollen gel particles is low, liquid pathways are not blocked by collapsed swollen gel particles, resulting in a water-absorbing resin having a high liquid permeability.

As described above, the difference in degree of collapse of swollen gel particles significantly influences the functions of a water-absorbing resin when the water-absorbing resin absorbs water. Therefore, it is very important to determine the degree of collapse of swollen gel particles in order to predict the functions of the water-absorbing resin.

BRIEF DESCRIPTION OF DRAWINGS

FIG. 3 shows positions at which a gel layer having a liquid absorbed therein is pressed.

DESCRIPTION OF EMBODIMENTS

Figure 1:
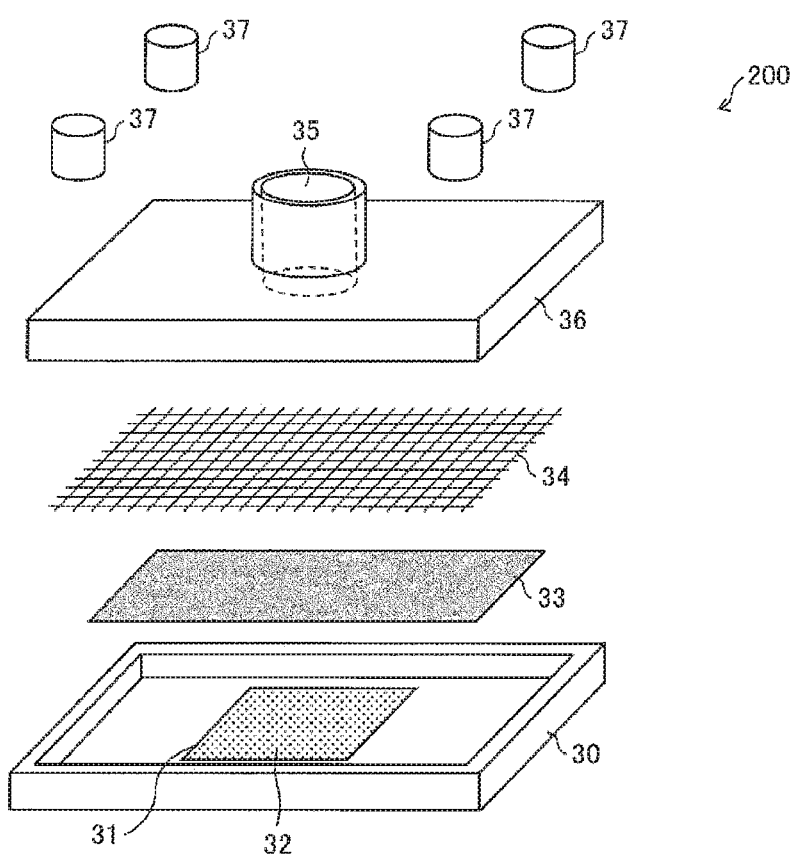
FIG. 1 schematically illustrates a structure of a measurement instrument for use in measuring the shape retention capacity of gel particles.

The following describes, in detail, polyacrylic acid (salt)-based water-absorbing resin powder, a method for producing the polyacrylic acid (salt)-based water-absorbing resin powder, and a method for evaluating the polyacrylic acid (salt)-based water-absorbing resin powder, in accordance with embodiments of the present invention. The present invention is not limited to the embodiments described below, but can be altered in various ways within the scope of the claims. The present invention also encompasses, in its technical scope, any embodiment derived by combining technical means disclosed in different embodiments.

[1] Term Definition

[1-1] "Water-absorbing Resin"

The term "water-absorbing resin" in an embodiment of the present invention denotes a water-swellable, water-insoluble polymer gelling agent. As used herein, the term "water-swellable" means that the centrifuge retention capacity (CRC) determined by ERT442.2-02 is 5 g/g or more, and the term "water-insoluble" means that the water-soluble content (Ext) determined by ERT470.2-02 is 50 weight % or less. It is noted that the "centrifuge retention capacity (CRC)" may also be referred to as "fluid retention capacity without pressure".

The water-absorbing resin may be designed appropriately according to its use and is not limited to a particular kind. However, the water-absorbing resin is preferably a hydrophilic crosslinked polymer created via crosslinking polymerization of carboxyl-containing unsaturated monomers. Furthermore, the water-absorbing resin is not limited to a 100% (100 weight %) polymer and may be a composition that contains an additive or the like, provided that the above-described performance is maintained.

Furthermore, the term "water-absorbing resin" in an embodiment of the present invention not only includes water-absorbing resins in powder form that are obtained by crushing and drying the hydrophilic crosslinked polymer but also includes water-absorbing resins in some other form obtained in various steps, examples of which include: partially or entirely polymerized, uncrushed water-absorbing resins in sheet form, fibrous form, film form, and particle form (crosslinked hydrogel polymers); crushed water-absorbing resins in particle form (particulate crosslinked hydrogel polymers); dried water-absorbing resins in powder form; and, in a case where the steps of pulverizing, classifying, surface treating, addition of additives, granulating and/or the like are performed after the drying, water-absorbing resins obtained in the respective steps.

In a case where the "water-absorbing resin" is a water-absorbing resin in powder form that is obtained by crushing and drying the hydrophilic crosslinked polymer, such a water-absorbing resin is referred to as "water-absorbing resin powder". Therefore, the term "water-absorbing resin powder" in an embodiment of the present invention includes a water-absorbing resin that has not been subjected to surface treatment including surface crosslinking and a water-absorbing resin that has been subjected to surface treatment including surface crosslinking, provided that the water-absorbing resin is in powder form that is obtained by crushing and drying the hydrophilic crosslinked polymer. Furthermore, the term "water-absorbing resin powder" in an embodiment of the present invention also includes, in a case where the steps of pulverizing, classifying, surface treating, addition of additives, granulating and/or the like are performed after the drying, water-absorbing resins obtained in the respective steps.

[1-2] "Polyacrylic Acid (Salt)"

The term "polyacrylic acid (salt)" in an embodiment of the present invention denotes a polymer that optionally contains a graft component and that contains, as a main component, acrylic acid and/or salt thereof as repeating unit.

Specifically, the term "polyacrylic acid (salt)" in an embodiment of the present invention denotes a polymer in which acrylic acid (salt) essentially accounts for 50 mol % to 100 mol %, preferably 70 mol % to 100 mol %, more preferably 90 mol % to 100 mol %, particularly preferably substantially 100 mol % of all the monomers to be polymerized (except an internal crosslinking agent). In a case where a polyacrylic acid (salt) is used as a polymer, the polyacrylic acid (salt) necessarily contains a water-soluble salt, and the main component of the water-soluble salt (neutralized salt) is preferably a monovalent salt, more preferably an alkali metal salt or an ammonium salt, even more preferably an alkali metal salt, particularly preferably a sodium salt.

[1-3] "EDANA" and "ERT"

The term "EDANA" is an acronym for the European Disposables and Nonwovens Associations, and the term "ERT" is an acronym for EDANA recommended test methods, which are European standard (de facto international standard) methods for measuring water-absorbing resins. It is noted that, unless otherwise stated, the measurements in an embodiment of the present invention are performed in accordance with ERT (Known Literature: revised in 2002).

(a) "CRC" (ERT441.2-02)

The term "CRC" is an acronym for "centrifuge retention capacity" and denotes a fluid retention capacity without pressure. Specifically, the term "CRC" denotes a fluid retention capacity (unit: g/g) of a water-absorbing resin determined by allowing 0.200 g of the water-absorbing resin in a non-woven fabric bag to freely swell for 30 minutes in a large excess of a 0.9 weight % aqueous sodium chloride solution and thereafter draining the water-absorbing resin with the use of a centrifugal separator. It is noted that the CRC of a crosslinked hydrogel polymer (in this specification, hereinafter may be referred to as "gel CRC") was measured under the conditions in which the amount of a sample was changed to 0.4 g and the free ペ—ジ: 21 swelling time was changed to 24 hours.

(b) "AAP" (ERT442.2-02)

The term "AAP" is an acronym for "absorption against pressure" and denotes a fluid retention capacity under pressure. Specifically, the term "AAP" denotes a fluid retention capacity (unit: g/g) of a water-absorbing resin determined by allowing 0.900 g of the water-absorbing resin to swell in a 0.9 weight % aqueous sodium chloride solution under a load of 2.06 kPa (0.3 psi, 21 g/cm$^2$) for 1 hour. It is noted that, although ERT442.2-02 uses the term "Absorption Under Pressure", the "AAP" is substantially the same as "Absorption Under Pressure". In embodiments and examples of the present invention, the measurements were performed under the condition in which the load was changed to 4.83 kPa (0.7 psi, 49 g/cm$^2$).

(c) "Ext" (ERT470.2-02)

The term "Ext" is an abbreviation for "extractables" and denotes a water-soluble component (amount of water-soluble component, or water-soluble content). Specifically, the term "Ext" denotes the amount (unit: weight %) of dissolved polymer determined by adding 1.0 g of a water-absorbing resin to 200 ml of a 0.9 weight % aqueous sodium chloride solution and stirring the solution at 500 rpm for 16 hours. The amount of dissolved polymer is determined by pH titration. It is noted that the water-soluble content of a crosslinked hydrogel polymer (in this specification, this water-soluble content may be hereinafter referred to as "gel Ext") was measured under the conditions in which the amount of a sample was changed to 5.0 g and the stirring time was changed to 24 hours.

(d) "PSD" (ERT420.2-02)

The term "PSD" is an acronym for "particle size distribution" and denotes a particle size distribution of a water-absorbing resin determined by sieve classification. It is noted that weight average particle diameter (D50) and particle size distribution are measured by methods similar to "1) Average Particle Diameter and Distribution of Particle Diameter" disclosed in lines 25 to 43 on page 7 of the specification of European Patent No. 0349240. A method of measuring the PSD of a crosslinked hydrogel polymer will be described later. The number of standard sieves (mesh sizes) for use in particle size measurement may be increased as needed depending on the particle size of a to-be-measured object. In regard to measurement conditions and the like which are not disclosed in European Patent No. 0349240, reference may be made to European Patent No. 1594556 depending on need.

(e) "Residual Monomers" (ERT410.2-02)

The term "residual monomers" denotes monomers (monomer content) (hereinafter referred to as "residual monomers") remaining in a water-absorbing resin. Specifically, the term "residual monomers" denotes a monomer content (unit: ppm) determined by adding 1.0 g of a water-absorbing resin to 200 ml of a 0.9 weight % aqueous sodium chloride solution and stirring the solution with the use of a stirrer chip 35 mm in length at 500 rpm for 1 hour and thereafter determining the amount of monomers dissolved in the solution. The amount of dissolved monomers is determined using high performance liquid chromatography (HPLC). It is noted that the amount of residual monomers in a crosslinked hydrogel polymer is a value (unit: ppm) obtained by performing the measurement under the conditions in which the amount of a sample is changed to 2 g and the stirring time is changed to 3 hours and converting the measured value to weight per resin solid content of the crosslinked hydrogel polymer.

(f) "Moisture Content" (ERT430.2-02)

The term "moisture content" denotes a moisture content of a water-absorbing resin. Specifically, the "moisture content" is a value (unit: weight %) calculated from a drying loss resulting from drying 1 g of a water-absorbing resin at 105° C. for 3 hours. It is noted that, in an embodiment of the present invention, each sample was measured five times under the condition in which the drying temperature was changed to 180° C. and the mean of the measured values was used. The moisture content of a crosslinked hydrogel polymer was measured under the conditions in which the amount of a sample was changed to 2 g, the drying temperature was changed to 180° C., and the drying time was changed to 16 hours. Furthermore, in an embodiment of the present invention, a value calculated through "100−moisture content (weight %)" is used as a "resin solid content" and this is applicable to both a water-absorbing resin and a crosslinked hydrogel polymer.

[1-4] "Liquid Permeability"

In an embodiment of the present invention, the term "liquid permeability" denotes flowability of liquid between swollen gel particles under load or without load. Typical methods of measuring the "liquid permeability" are, for example, saline flow conductivity (SFC) and gel bed permeability (GBP).

The "SFC" refers to a liquid permeability of a water-absorbing resin under a load of 2.07 kPa with respect to a 0.69 weight % aqueous sodium chloride solution, and is measured in accordance with the SFC testing method disclosed in U.S. Pat. No. 5,669,894. The "GBP" refers to a liquid permeability of a water-absorbing resin with respect to a 0.69 weight % aqueous sodium chloride solution under load or in freely swellable conditions, and is measured in accordance with the GBP testing method disclosed in International Publication No. WO 2005/016393.

[1-5] "Water Absorption Speed"

In an embodiment of the present invention, the term "water absorption speed" denotes a water absorption speed represented by "free swell rate (FSR)" (unit: g/(g·s)) or "water absorption time according to a vortex method (Vortex)" (unit: seconds). It is noted that the term "FSR" is an acronym for "free swell rate". Specifically, the "free swell rate (FSR)" is the speed (unit: g/(g·s)) of absorption of 20 g of a 0.9 weight % aqueous sodium chloride solution by 1 g of a water-absorbing resin and is a water absorption speed determined in accordance with the method defined in International Publication No. WO 2009/016055. The "water absorption time according to a vortex method (Vortex)" is water absorption time determined in accordance with the "Testing method for water absorption rate of super absorbent polymers" in JIS K7224 and is time taken by 2 g of a water-absorbing resin to absorb 50 g of physiological saline.

[1-6] "Gel-crushing"

In an embodiment of the present invention, the term "gel-crushing" denotes an operation of applying, for example, shear force, compressive force, and/or the like to the obtained crosslinked hydrogel polymer and thereby crushing the crosslinked hydrogel polymer into smaller pieces.

Specifically, the "gel-crushing" is to subject a crosslinked hydrogel polymer to gel-crushing in a way such that the crushed crosslinked hydrogel polymer has a weight average particle diameter (D50) of 300 μm to 3000 μm, more preferably 350 μm to 2000 μm, and has a particle size distribution with a logarithmic standard deviation (σζ) of preferably 0.2 to 1.0.

It is noted that the resulting crosslinked hydrogel polymer may differ in form depending on the type of polymerization apparatus. For example, in a case of aqueous solution polymerization without stirring (static aqueous solution polymerization, in particular, belt polymerization), gel-crushing is performed after polymerization. On the other hand, in a case of kneader polymerization, the polymerization and gel-crushing are sequentially performed within a single apparatus. That is, embodiments of the present invention encompass both of the above arrangements. However, it is preferable that kneader polymerization and gel-crushing be sequentially performed in a single apparatus and thereafter another gel-crushing be performed.

[1-7] "Swollen Gel Particles"

In an embodiment of the present invention, the term "swollen gel" denotes a water-absorbing resin in the form of hydrogel which is generated when water-absorbing resin powder has swollen with a sweller liquid, and the term "swollen gel particles" denotes water-absorbing resin particles that constitute the "swollen gel". The term "swell" in an embodiment of the present invention means that, as a result of take-up of a sweller liquid by water-absorbing resin powder, the weight or volume of the water-absorbing resin powder increases.

[1-8] "Swelling Capacity"

In an embodiment of the present invention, the term "swelling capacity" denotes, when water-absorbing resin powder has swollen with a sweller liquid to become swollen gel particles, the ratio of the amount of the swollen gel particles to the amount of the unswollen water-absorbing resin powder. The ratio may be weight ratio of the swollen gel particles to the water-absorbing resin powder, or may be volume ratio of the swollen gel particles to the water-absorbing resin powder. It is preferable that the swelling capacity be weight ratio. A specific method of calculating the "swelling capacity" and the like will be described later in detail.

[1-9] "Gel Particle's Collapse Rate at Swelling"

In an embodiment of the present invention, the term "gel particle's collapse rate at swelling" denotes the weight percentage of fine gel particles resulting when water-absorbing resin powder swells with a 0.9 weight % aqueous sodium chloride solution, and is determined by the following method.

i) Allow water-absorbing resin powder having a particle size of 150 μm or more and less than 850 μm to swell with a 0.9 weight % aqueous sodium chloride solution for 1 hour.

ii) Subject the swollen gel obtained in step i) to wet classification with sieves, find the cumulative percentage of swollen gel particles passed through each of the sieves from the amount of swollen gel particles remaining on the mesh of each sieve, convert the mesh sizes of the sieves used in wet classification into mesh sizes for dry classification, and create a graph that plots the cumulative percentages and the mesh sizes.

iii) Find the weight percentage (unit: weight %) of particles having a particle size less than 180 μm, in terms of dry classification, from the graph created in step ii), and use the found weight percentage as a "gel particle's collapse rate at swelling".

[1-10] "Weight Average Molecular Weight of Water-soluble Component"

In an embodiment of the present invention, the term "weight average molecular weight of water-soluble component" denotes a value (unit: daltons, which, in this specification, is hereinafter referred to as "Da" for short) of the weight average molecular weight, determined by gel permeation chromatography (GPC), of a component (water-soluble component) of a water-absorbing resin which dissolves in a 0.9 weight % aqueous sodium chloride solution when the water-absorbing resin is added in the 0.9 weight % aqueous sodium chloride solution. That is, the "weight average molecular weight of water-soluble component" is a value determined by GPC of the solution obtained in the measurement method described in the above section (1-3) (c) "Ext". It is noted that the weight average molecular weight of the water-soluble component of a crosslinked hydrogel polymer was measured under the conditions in which the amount of a sample grain-refined to a particle size of preferably 5 mm or less, more preferably 1 mm to 3 mm, was changed to 5.0 g and the stirring time was changed to 24 hours.

[1-11] "Gel Grinding Energy" (GGE, GGE (2))

In an embodiment of the present invention, the term "gel grinding energy" denotes mechanical energy per unit weight of a crosslinked hydrogel polymer required for a gel-crusher to crush the crosslinked hydrogel polymer. It is noted that the "gel grinding energy" does not include energy to heat or cool a jacket or energy of introduced water or steam. The "gel grinding energy" is referred to as "GGE" for short. The GGE is calculated using the following Equation (1) in a case where a gel-crusher is driven by three-phase electric power.

$$\text{GGE[J/g]} = \frac{\{\sqrt{3} \times \text{voltage} \times \text{current} \times \text{power factor} \times \text{motor efficiency}\}}{\{\text{weight of crosslinked hydrogel polymer fed into gel-crusher per second}\}} \quad \text{Equation (1)}$$

In the equation, the "power factor" and the "motor efficiency" are values inherent to the gel-crusher and vary depending on operation conditions and the like of the gel-crusher, and may have a value of 0 to 1. In a case where the gel-crusher is driven by single-phase electric power, the GGE can be calculated using a modified equation where "$\sqrt{3}$" in the above equation is changed to "1". In the equation, the unit of voltage is V, the unit of current is A, and the unit of weight of the crosslinked hydrogel polymer is g/s. It is also possible to employ an arrangement in which a plurality of gel-crushers are used to crush a crosslinked hydrogel polymer. In this arrangement, the GGE may be calculated for each gel-crusher.

The mechanical energy applied to a crosslinked hydrogel polymer is one of the important factors in an embodiment of the present invention. Therefore, it is more preferable that the gel grinding energy be calculated excluding the value of current flowing while the gel-crusher is in the idle state. Especially in a case where a plurality of gel-crushers are used to crush gel, the total value of current during the idle state is large and thus a calculation excluding the values of current during the idle state is preferred. The gel grinding energy in this case is calculated using the following Equation (2). It is noted that, for distinction from the above-described GGE, the gel grinding energy calculated using the following Equation (2) is represented as GGE (2).

$$GGE(2)[J/g]=\{\sqrt{3}\times voltage\times(current\ during\ gel\text{-}crushing-current\ during\ idle\ state)\times power\ factor\times motor\ efficiency\}/\{weight\ of\ crosslinked\ hydrogel\ polymer\ fed\ into\ gel\text{-}crusher\ per\ second\}$$   Equation (2)

The "power factor" and the "motor efficiency" in the GGE (2) are those during gel-crushing. Since the value of current during the idle state is small, the values of the power factor and the motor efficiency are defined approximately as in the Equation (2). The "weight of crosslinked hydrogel polymer fed into gel-crusher per second (g/s)" in the Equations (1) and (2) is, for example, in a case where the crosslinked hydrogel polymer is continuously fed with the use of a quantitative feeder and where the unit of the feeding amount is t/hr, the value obtained by converting the amount to g/s.

[1-12] Other

In this specification, a range of "X to Y" denotes "X or more and Y or less". A unit of weight "t (ton)" denotes "metric ton" and, in addition, unless otherwise noted, the unit "ppm" denotes "ppm by weight". Furthermore, the terms "weight" and "mass" are used as synonyms, the terms "weight %" and "mass %" are used as synonyms, and the terms "parts by weight" and "parts by mass" are used as synonyms. Furthermore, the term "XX acid (salt)" denotes "XX acid and/or salt thereof", and the term "(meth)acrylic" denotes "acrylic and/or methacrylic".

[2] Physical Properties of Polyacrylic Acid (Salt)-based Water-absorbing Resin Powder Water-absorbing resin powder in accordance with an embodiment of the present invention is water-absorbing resin powder containing a polyacrylic acid (salt) as a main component and satisfies the following physical properties (1) to (4). It is noted that the term "water-absorbing resin powder containing a polyacrylic acid (salt) as a main component" denotes water-absorbing resin powder that contains a polyacrylic acid (salt) in an amount of preferably 50 weight % or more, more preferably 80 weight % or more, even more preferably 90 weight % or more. In this specification, the "water-absorbing resin powder containing a polyacrylic acid (salt) as a main component" may be referred to as "polyacrylic acid (salt)-based water-absorbing resin powder".

(1) A water absorption time according to a vortex method (Vortex) is 42 seconds or less, or a free swell rate (FSR) is 0.28 g/(g·s) or more.

(2) The percentage of water-absorbing resin powder having a particle size of 150 μm or more and less than 850 μm is 90 weight % or more.

(3) A gel particle's collapse rate at swelling is 10 weight % or less.

(4) An internal gas bubble ratio defined by the following equation is 0.1% to 2.5%:

Internal gas bubble ratio (%)=(true density−apparent density)/true density×100.

The following describes the physical properties (1) to (4) and other physical properties.

[2-1] Water Absorption Time According to Vortex Method (Vortex)/Free Swell Rate (FSR)

Water-absorbing resin powder in accordance with an embodiment of the present invention has a water absorption time (Vortex), according to a vortex method, of 42 seconds or less or has a free swell rate (FSR) of 0.28 g/(g·s) or more. It is noted that both the water absorption time according to a vortex method (Vortex) and the free swell rate (FSR) are physical properties representing the water absorption speed of the water-absorbing resin powder.

Water-absorbing resin powder of an embodiment of the present invention in which the water absorption time according to a vortex method (Vortex) is 42 seconds or less is preferred, because liquid take-up is good enough and, when the water-absorbing resin powder is used in an absorbent body of an absorbent article, a user of the absorbent article is unlikely to feel uncomfortable. Although a water absorption time (Vortex) of 42 seconds or less may be good enough from the viewpoint of liquid take-up, the water absorption time (Vortex) is preferably 40 seconds or less, more preferably 35 seconds or less, even more preferably 30 seconds or less, particularly preferably 25 seconds or less. Furthermore, the lower limit of the water absorption time (Vortex) is not particularly limited, provided that the lower limit is more than 0 seconds. In general, the lower limit is preferably 5 seconds or more, more preferably 10 seconds or more.

Water-absorbing resin powder of an embodiment of the present invention in which the free swell rate (FSR) is 0.28 g/(g·s) or more is preferred, because liquid take-up is good enough and, when the water-absorbing resin powder is used in an absorbent body of an absorbent article, a user of the absorbent article is unlikely to feel uncomfortable. Although a free swell rate (FSR) of 0.28 g/(g·s) or more may be good enough from the viewpoint of liquid take-up, the free swell rate (FSR) is preferably 0.30 g/(g·s) or more, more preferably 0.32 g/(g·s) or more, even more preferably 0.34 g/(g·s) or more, particularly preferably 0.36 g/(g·s) or more. Furthermore, the upper limit of the free swell rate (FSR) is preferably 1.00 g/(g·s) or less.

[2-2] Percentage of Water-absorbing Resin Powder having a Particle Size of 150 μm or more and Less than 850 μm Water-absorbing resin powder in accordance with an embodiment of the present invention is such that 90 weight % or more thereof has a particle size of 150 μm or more and less than 850 μm.

In this specification, the term "particle size" denotes a particle size defined by a JIS standard sieve (JIS Z 8801-1 (2000)). Furthermore, the term "water-absorbing resin powder having a particle size of 150 μm or more and less than 850 μm" denotes water-absorbing resin powder that can pass through a JIS standard sieve having a mesh size of 850 μm and that cannot pass through a JIS standard sieve having a mesh size of 150 μm. Furthermore, the term "percentage of water-absorbing resin powder having a particle size of 150 μm or more and less than 850 μm" denotes the weight percentage (unit: weight %) of water-absorbing resin powder having a particle size of 150 μm or more and less than 850 μm relative to the total amount of water-absorbing resin powder subjected to sieve classification.

Water-absorbing resin powder in which 90 weight % or more thereof has a particle size of 150 μm or more and less than 850 μm is preferred, because performance reduction resulting from fine particles of the water-absorbing resin is prevented and generation of powder dust is prevented. Although the percentage of water-absorbing resin powder having a particle size of 150 μm or more and less than 850 μm only has to be 90 weight % or more, the percentage is preferably 95 weight % or more, more preferably 97 weight % or more.

[2-3] Gel Particle's Collapse Rate at Swelling

Water-absorbing resin powder in accordance with an embodiment of the present invention has a gel particle's collapse rate at swelling of 10 weight % or less.

Water-absorbing resin powder having a gel particle's collapse rate at swelling of 10 weight % or less is preferred, because this reduces fine gel particles resulting from collapse of swollen gel during swelling. Although the gel particle's collapse rate at swelling only has to be 10 weight % or less, the gel particle's collapse rate at swelling is preferably 9.9 weight % or less, more preferably 9.8 weight % or less, even more preferably 9.6 weight % or less.

[2-4] Internal Gas Bubble Ratio

Water-absorbing resin powder in accordance with an embodiment of the present invention has an internal gas bubble ratio, defined by the following equation, of 0.1% to 2.5%:

Internal gas bubble ratio (%)=(true density−apparent density)/true density×100.

An internal gas bubble ratio of 0.1% to 2.5% is preferred, because water-absorbing resin powder having such an internal gas bubble ratio has a reduced volume and therefore more water-absorbing resin powder can be packed into each transportation container (for example, a flexible container bag) and, as a result, transportation cost is reduced. The water-absorbing resin powder having the above internal gas bubble ratio is preferred also because collapse of closed-cells due to damage is less likely to occur, such that the water-absorbing resin powder is resistant to damage.

Although an internal gas bubble ratio of 0.1% to 2.5% is good enough from the above points of view, the internal gas bubble ratio is preferably 0.2% to 2.0%, more preferably 0.3% to 1.7%, even more preferably 0.5% to 1.5%.

[2-5] Other Physical Properties

Polyacrylic acid (salt)-based water-absorbing resin powder in accordance with an embodiment of the present invention satisfies the physical properties (1) to (4) and preferably further satisfies any one or more of the following physical properties (5) to (9):

(5) a fluid retention capacity under pressure (AAP) is 20 g/g or more;

(6) a saline flow conductivity (SFC) is $10 \times 10^{-7} \cdot cm^3 \cdot s \cdot g^{-1}$ or more;

(7) the percentage of water-absorbing resin powder having a particle size less than 150 μm is 5 weight % or less;

(8) the percentage of water-absorbing resin powder having a particle size of 850 μm or more is 5 weight % or less; and (9) a centrifuge retention capacity (CRC) is 10 g/g or more.

The following describes the physical properties (5) to (9).

[2-5-1] Fluid Retention Capacity under Pressure (AAP)

The water-absorbing resin powder in accordance with an embodiment of the present invention has a fluid retention capacity under pressure (AAP), which is under a load of 4.83 kPa, of preferably 20 g/g or more, more preferably 21 g/g or more, even more preferably 22 g/g or more, particularly preferably 23 g/g or more. Although the upper limit of the fluid retention capacity under pressure (AAP) is not particularly limited, the upper limit is preferably 35 g/g or less, more preferably 30 g/g or less, even more preferably 28 g/g or less, from the viewpoint of balancing with other physical properties.

A fluid retention capacity under pressure (AAP) of 20 g/g or more is preferred, because this prevents liquid leakage when the water-absorbing resin powder of an embodiment of the present invention is used in a sanitary product such as a disposable diaper. It is apparent that the fluid retention capacity under pressure (AAP) becomes high in a case where the gel particle's collapse rate at swelling is 10 weight % or less.

[2-5-2] Saline Flow Conductivity (SFC)

The water-absorbing resin powder in accordance with an embodiment of the present invention has a saline flow conductivity (SFC) (unit: $\times 10^{-7} \cdot cm^3 \cdot s \cdot g^{-1}$, the unit is hereinafter omitted), under a load of 2.07 kPa, of preferably 10 or more, more preferably 20 or more, even more preferably 30 or more, further still more preferably 50 or more, particularly preferably 70 or more, most preferably 90 or more. An SFC of 10 or more is preferred, because this prevents liquid leakage when the water-absorbing resin powder of an embodiment of the present invention is used in an absorbent body of an absorbent article such as a disposable diaper. It is apparent that the saline flow conductivity (SFC) becomes high in a case where the gel particle's collapse rate at swelling is 10 weight % or less.

[2-5-3] Percentage of Water-absorbing Resin Powder having a Particle Size Less than 150 μm The water-absorbing resin powder in accordance with an embodiment of the present invention preferably contains fine particles that pass through a sieve (JIS standard sieve) having a mesh size of 150 μm in as small an amount as possible, from the viewpoint of an improvement in physical properties of the water-absorbing resin powder. Therefore, the percentage of water-absorbing resin powder having a particle size less than 150 μm is preferably 5 weight % or less, more preferably 4 weight % or less, even more preferably 3 weight % or less, relative to the entire water-absorbing resin powder subjected to sieve classification.

[2-5-4] Percentage of Water-absorbing Resin Powder having a Particle Size of 850 μm or more The water-absorbing resin powder in accordance with an embodiment of the present invention preferably contains coarse particles that cannot pass through a sieve (JIS standard sieve) having a mesh size of 850 μm in as small an amount as possible, from the viewpoint of an improvement in physical properties of the water-absorbing resin powder. Therefore, the percentage of water-absorbing resin powder having a particle size of 850 μm or more is preferably 5 weight % or less, more preferably 3 weight % or less, and even more preferably 1 weight % or less, relative to the entire water-absorbing resin powder subjected to sieve classification.

[2-5-4] Centrifuge Retention Capacity (CRC)

The water-absorbing resin powder in accordance with an embodiment of the present invention has a centrifuge retention capacity (CRC) of preferably 10 g/g or more, more preferably 20 g/g or more, even more preferably 25 g/g or more, particularly preferably 30 g/g or more. Although the upper limit of the centrifuge retention capacity (CRC) is not particularly limited, the upper limit is preferably 50 g/g or less, more preferably 45 g/g or less, even more preferably 40 g/g or less, from the viewpoint of balancing with other physical properties. A centrifuge retention capacity (CRC) within the above range is preferred, because water-absorbing resin powder having such a centrifuge retention capacity can be used as an absorbent body of an absorbent article such as a disposable diaper.

[3] Method for Producing Polyacrylic Acid (Salt)-based Water-absorbing Resin Powder As described above, polyacrylic acid (salt)-based water-absorbing resin powder in accordance with an embodiment of the present invention undergoes little collapse when swells into gel and, as a result, has an excellent fluid retention capacity under pressure and an excellent liquid permeability as well as an excellent water absorption speed.

The polyacrylic acid (salt)-based water-absorbing resin powder may be obtained by a polyacrylic acid (salt)-based water-absorbing resin powder production method which includes: a polymerization step of polymerizing an acrylic acid (salt)-based aqueous monomer solution; a gel-crushing step of crushing a crosslinked hydrogel polymer during or after polymerization; and a drying step performed after gel-crushing, where, in the gel-crushing step, an inorganic compound and/or water-absorbing resin fine particles is/are added to the crosslinked hydrogel polymer having a resin solid content of 10 weight % or more and 80 weight % or less and gel-crushing of the crosslinked hydrogel polymer is performed under specific gel-crushing conditions.

[3-1] Polymerization Step

In an embodiment of the present invention, the polymerization step is a step of polymerizing an acrylic acid (salt)-based aqueous monomer solution to obtain a crosslinked hydrogel polymer. It is noted that, in this specification, the term "acrylic acid (salt)-based aqueous monomer solution" (in this specification, this may be hereinafter simply referred to as "aqueous monomer solution") denotes an aqueous monomer solution containing acrylic acid (salt) as a main component. As used herein, the term "aqueous monomer solution containing acrylic acid (salt) as a main component" denotes an aqueous monomer solution that contains acrylic acid (salt) as monomer in an amount of preferably 50 mol % to 100 mol %, more preferably 70 mol % to 100 mol %, even more preferably 90 mol % to 100 mol %, particularly preferably substantially 100 mol %.

(Monomer)

The water-absorbing resin powder obtained in an embodiment of the present invention is created using, as a raw material thereof, monomer that contains acrylic acid (salt) as a main component, and is polymerized normally in the state of an aqueous solution. The monomer concentration of the acrylic acid (salt)-based aqueous monomer solution is preferably 10 weight % to 80 weight %, more preferably 20 weight % to 80 weight %, even more preferably 30 weight % to 70 weight %, particularly preferably 40 weight % to 60 weight %.

Furthermore, it is preferable that, from the viewpoint of water absorption performance and residual monomers, the acid groups of the crosslinked hydrogel polymer obtained via polymerization of the acrylic acid (salt)-based aqueous monomer solution be at least partially neutralized. Although such a partially neutralized salt is not limited to a particular kind, the partially neutralized salt is preferably a monovalent salt selected from alkali metal salts, ammonium salts, and amine salts, more preferably an alkali metal salt, even more preferably an alkali metal salt selected from sodium salts, lithium salts and potassium salts, particularly preferably a sodium salt, from the viewpoint of water absorption performance. Therefore, although a basic substance for use in the neutralization is not limited to a particular kind, the basic substance is preferably a monovalent basic substance such as a hydroxide of an alkali metal (e.g., sodium hydroxide, potassium hydroxide, lithium hydroxide) or a (hydrogen) carbonate (e.g., sodium (hydrogen)carbonate, potassium (hydrogen)carbonate), and particularly preferably sodium hydroxide.

The neutralization may be performed in the form and condition before polymerization, during polymerization, or after polymerization. For example, the neutralization may be a neutralization of a crosslinked hydrogel polymer obtained via polymerization of acrylic acid that is unneutralized or neutralized to a low degree (for example, mol % to 30 mol % neutralized), especially performed concurrently with gel-crushing. However, from the viewpoint of improvements in productivity and physical properties, it is preferable that the acrylic acid be neutralized before polymerization. That is, it is preferable that neutralized acrylic acid (that is, partially neutralized salt of acrylic acid) be used as monomer.

Although the neutralization rate in the neutralization is not particularly limited, the neutralization rate is preferably 10 mol % to 100 mol %, more preferably 30 mol % to 95 mol %, even more preferably 45 mol % to 90 mol %, particularly preferably 60 mol % to 80 mol %. The neutralization temperature is not particularly limited as well, and is preferably 10° C. to 100° C., more preferably 30° C. to 90° C. In regard to other conditions for the neutralization process, the conditions disclosed in European Patent No. 574260 are suitably used in an embodiment of the present invention. It is preferable that the crosslinked hydrogel polymer having a neutralization rate falling within the above range be subjected to gel-crushing in the gel-crushing step described later.

Furthermore, for the purpose of improving physical properties of the water-absorbing resin powder obtained in an embodiment of the present invention, some component may be added to an acrylic acid (salt)-based aqueous monomer solution, a crosslinked hydrogel polymer, a dry polymer, a water-absorbing resin, or the like at any step of the production process of an embodiment of the present invention. Examples of the component include: water soluble resins such as starch, cellulose, polyvinyl alcohol (PVA), and polyethyleneimine; foaming agents such as carbonates, azo compounds, and gas bubbles; surfactants; and the like. The amount of such a component(s) added is, in a case where the component(s) is/are any of the above water-soluble resins, preferably 50 weight % or less, more preferably 20 weight % or less, even more preferably 10 weight % or less, particularly preferably 3 weight % or less, relative to the monomers. On the other hand, in a case where the component(s) is/are any of the foaming agents or surfactants, the amount of the foaming agent or surfactant added is preferably 5 weight % or less, and more preferably 1 weight % or less, relative to the monomers. The addition of the above aqueous solution resin(s) gives a graft polymer such as, specifically, a starch-acrylic acid polymer or a PVA-acrylic acid polymer. These polymers are also regarded as polyacrylic acids (salts) in an embodiment of the present invention.

Furthermore, for improvements in color stability (color stability over long-term storage under high-temperature and humidity conditions) and urine resistance (prevention of gel deterioration) of the water-absorbing resin powder obtained in an embodiment of the present invention, a chelating agent, an α-hydroxycarboxylic acid compound, an inorganic reducing agent, and/or the like may be used. Of these, a chelating agent is particularly preferred. The amount of any of these used is preferably 10 ppm to 5000 ppm, more preferably 10 ppm to 1000 ppm, even more preferably 50 ppm to 1000 ppm, particularly preferably 100 ppm to 1000 ppm, relative to the water-absorbing resin. It is noted that the chelating agents disclosed in U.S. Pat. No. 6,599,989 and International Publication No. WO 2008/090961 may also be used in an embodiment of the present invention. Of these, aminocarboxylic acid-based metal chelating agents and polyvalent phosphoric acid-based compounds are preferred.

In a case where acrylic acid (salt) is used as a main component in an embodiment of the present invention, a hydrophilic or hydrophobic unsaturated monomer other than the acrylic acid (salt) (in this specification, such a hydrophilic or hydrophobic unsaturated monomer is hereinafter referred to as "other monomer") may be used in combination with the acrylic acid (salt). Such other monomer is not limited to a particular kind, and examples of the monomer include: methacrylic acid, maleic acid (anhydride), 2-(meth)acrylamide-2-methylpropanesulfonic acid, (meth)acryloxy alkanesulfonic acid, N-vinyl-2-pyrrolidone, N-vinylacetamide, (meth)acrylamide, N-isopropyl(meth)acrylamide, N,N-dimethyl(meth)acrylamide, 2-hydroxyethyl(meth)acrylate, methoxypolyethyleneglycol(meth)acrylate, polyethyleneglycol(meth)acrylate, stearyl acrylate, and salts thereof. In a case where such other monomer is used, the amount of the monomer used is determined appropriately so as not to impair water absorption performance of the resulting water-absorbing resin powder, and is not particularly limited. The amount of such other monomer used is preferably less than 50 mol %, more preferably less than 30 mol %, even more preferably less than 10 mol %, relative to the total weight of the monomers. It is noted that the lower limit of the amount used is 0 mol %.

(Internal Crosslinking Agent)

In an embodiment of the present invention, it is preferable to use an internal crosslinking agent, from the viewpoint of water absorption performance of the resulting water-absorbing resin powder. The internal crosslinking agent is not limited to a particular kind, and examples of the internal crosslinking agent include crosslinking agents polymerizable with acrylic acid, crosslinking agents reactive with carboxyl group, and crosslinking agents polymerizable with acrylic acid and reactive with carboxyl group.

Examples of the polymerizable crosslinking agents include compounds having at least two polymerizable double bonds per molecule, such as N,N'-methylene bisacrylamide, (poly)ethylene glycol di(meth)acrylate, (polyoxyethylene)trimethylolpropane tri(meth)acrylate, and poly(meth)allyloxy alkanes. Examples of the reactive crosslinking agents include: covalently bonding crosslinking agents such as polyglycidyl ethers (e.g., ethylene glycol diglycidyl ether) and polyhydric alcohols (e.g., propanediol, glycerin, sorbitol); and ionic bonding crosslinking agents such as polyvalent metal compounds (e.g., aluminum salt). Of these, from the viewpoint of water absorption performance, crosslinking agents polymerizable with acrylic acid are preferred, and acrylate-based polymerizable crosslinking agents, allyl-based polymerizable crosslinking agents, and acrylamide-based polymerizable crosslinking agents are more preferred. One of these internal crosslinking agents may be used individually or two or more of these internal crosslinking agents may be used in combination. It is noted that, in a case where any of the above polymerizable crosslinking agents and any of the above covalently bonding crosslinking agents are used in combination, the ratio of mixture is preferably 1:10 to 10:1.

The amount of the internal crosslinking agent used is, from the viewpoint of physical properties, preferably 0.001 mol % to 5 mol %, more preferably 0.002 mol % to 2 mol %, even more preferably 0.04 mol % to 1 mol %, particularly preferably 0.06 mol % to 0.5 mol %, most preferably 0.07 mol % to 0.2 mol %, relative to all the monomers excluding the crosslinking agent. In a particularly preferred embodiment of the present invention, the polymerizable crosslinking agent is used in an amount of preferably 0.01 mol % to 1 mol %, more preferably 0.04 mol % to 0.5 mol %, even more preferably 0.07 mol % to 0.1 mol %, relative to all the monomers excluding the crosslinking agent.

(Polymerization Initiator)

A polymerization initiator for use in an embodiment of the present invention is selected appropriately depending on how polymerization is performed, and is not limited to a particular kind. The polymerization initiator is, for example, a photolytic-type polymerization initiator, a pyrolysis-type polymerization initiator, a redox-type polymerization initiator, or the like.

Examples of the photolytic-type polymerization initiator include benzoin derivatives, benzyl derivatives, acetophenone derivatives, benzophenone derivatives, and azo compounds. Examples of the pyrolysis-type polymerization initiator include: persulfates such as sodium persulfate, potassium persulfate, and ammonium persulfate; peroxides such as hydrogen peroxide, t-butyl peroxide, and methyl ethyl ketone peroxide; and azo compounds such as 2,2'-azobis(2-amidinopropane)dihydrochloride and 2,2'-azobis[2-(2-imidazoline-2-yl)propane]dihydrochloride. Examples of the redox-type polymerization initiator include systems in which any of the persulfates and/or peroxides is/are used in combination with a reducing compound(s) such as L-ascorbic acid and/or acid sodium sulfite. It is also preferable to employ an embodiment in which any of the photolytic-type polymerization initiators and any of the pyrolysis-type polymerization initiators are used in combination.

The amount of the polymerization initiator used is preferably 0.0001 mol % to 1 mol %, more preferably 0.0005 mol % to 0.5 mol % relative to all the monomers. The polymerization initiator used in an amount of 1 mol % or less is preferred, because this prevents or reduces deterioration of color of the water-absorbing resin. Furthermore, the polymerization initiator used in an amount of 0.0001 mol % or more is preferred, because this prevents or reduces an increase in residual monomers.

(Polymerization Method)

A method for producing water-absorbing resin powder in accordance with an embodiment of the present invention may employ, as a polymerization method thereof, spray droplet polymerization or reversed phase suspension polymerization to obtain a particulate crosslinked hydrogel polymer. However, from the viewpoint of the liquid permeability (SFC) and free swell rate (FSR) of the resulting water-absorbing resin powder as well as polymerization controllability and the like, it is preferable to employ aqueous solution polymerization. The aqueous solution polymerization is not limited to a particular kind, and is more preferably continuous aqueous solution polymerization, even more preferably high-concentration continuous aqueous solution polymerization, particularly preferably high-concentration, high-temperature starting continuous aqueous solution polymerization. The polymerization is performed preferably via belt polymerization without stirring or via kneader polymerization with stirring. It is noted that the kneader polymerization with stirring means polymerizing a crosslinked hydrogel polymer (crosslinked hydrogel polymer having a polymerization rate of preferably 10 mol % or more, more preferably 50 mol % or more) preferably with stirring, more preferably with stirring and grain refining. Alternatively, an aqueous monomer solution (having a polymerization rate less than 10 mol %) may be stirred as needed before and/or after the belt polymerization without stirring.

Specific examples of the belt polymerization and the kneader polymerization include: continuous kneader polymerization disclosed in U.S. Pat. Nos. 6,987,171, 6,710,141, and the like; and continuous belt polymerization disclosed in U.S. Pat. Nos. 4,893,999 and 6,241,928, U.S. Patent Application Publication No. 2005/215734, and the like. These kinds of aqueous solution polymerization can produce water-absorbing resin powder with high productivity.

It is noted that, in the high-concentration continuous aqueous solution polymerization, the monomer concentration (solid content) is preferably 35 weight % or more, more preferably 40 weight % or more, even more preferably 45 weight % or more (upper limit is saturation concentration). In the high-temperature starting continuous aqueous solution polymerization, the temperature at the initiation of polymerization is preferably 30° C. or above, more preferably 35° C. or above, even more preferably 40° C. or above, particularly preferably 50° C. or above (upper limit is boiling point). It is also possible to employ high-concentration, high-temperature starting continuous aqueous solution polymerization which is a combination of the polymerization methods mentioned above.

Examples of the high-concentration, high-temperature starting continuous aqueous solution polymerization include the polymerization methods disclosed in U.S. Pat. Nos. 6,906,159 and 7,091,253. This polymerization method is preferred because it can produce water-absorbing resin powder with a high degree of whiteness and also can be easily applied to industrial-scale production.

The polymerization method in the production method in accordance with an embodiment of the present invention is suitably used in a large-scale スーパー: 61 production apparatus which handles a large production volume per line. The production volume is preferably 0.5 t/hr or more, more preferably 1 t/hr or more, even more preferably 5 t/hr or more, particularly preferably 10 t/hr or more.

The polymerization may be performed even under an air atmosphere, but is preferably performed under an inert gas atmosphere such as water vapor, nitrogen or argon (for example, an atmosphere having an oxygen concentration of volume % or less) from the viewpoint of preventing coloration. It is more preferable that the oxygen dissolved in monomer or in a solution containing monomer be replaced with an inert gas (degassed) so that the oxygen is, for example, less than 1 mg/L, before polymerization is performed. Such degassing makes the monomer highly stable, prevents gelation before polymerization, and thus makes it possible to provide more white water-absorbing resin powder having better physical properties.

[3-2] Gel-crushing Step

The definition of the gel-crushing step in an embodiment of the present invention was described earlier. In other words, the gel-crushing step is to obtain a particulate crosslinked hydrogel polymer (in this specification, this may be hereinafter referred to as "particulate hydrogel") by grain-refining the earlier-described crosslinked hydrogel polymer during or after polymerization. It is noted that this step is referred to as "gel-crushing" in distinction from "pulverization" in the following "[3-4] Pulverizing step and classification step".

In an embodiment of the present invention, in the gel-crushing step, an inorganic compound and/or water-absorbing resin fine particles is/are added to the crosslinked hydrogel polymer having a resin solid content of 10 weight % or more and 80 weight % or less and gel-crushing that satisfies at least one of the following (1) and (2) is performed:

(1) a gel grinding energy (GGE) is 18 J/g to 60 J/g;
(2) a gel grinding energy (2) (GGE (2)) is 9 J/g to 40 J/g.

It is preferable that, in an embodiment of the present invention, the gel-crushing step further satisfy any one or more of the following (3) to (5):

(3) the weight average molecular weight of a water-soluble component of the crosslinked hydrogel polymer increases by 10000 Da to 500000 Da;

(4) the particulate crosslinked hydrogel polymer obtained has a weight average particle diameter (D50) of 350 μm to 2000 μm; and (5) a logarithmic standard deviation ($\sigma\zeta$) of a particle size distribution of the particulate crosslinked hydrogel polymer obtained is 0.2 to 1.0.

(Resin Solid Content of Crosslinked Hydrogel Polymer that has not been Subjected to Gel-Crushing)

The resin solid content of the crosslinked hydrogel polymer that has not been subjected to gel-crushing is, from the viewpoint of physical properties, 10 weight % to 80 weight %, more preferably 30 weight % to 80 weight %, even more preferably 40 weight % to 80 weight %, particularly preferably 45 weight % to 60 weight %, most preferably 50 weight % to 60 weight %. In a case where the resin solid content is 10 weight % or more, the softness of the crosslinked hydrogel polymer does not increase, whereas in a case where the resin solid content is 80 weight % or less, the firmness of the crosslinked hydrogel polymer does not increase, and therefore such cases are preferred for good controllability of particle shape and particle size distribution. The resin solid content of such a crosslinked hydrogel polymer can be controlled appropriately by controlling the polymerization concentration, moisture evaporation during polymerization, addition of water-absorbing resin fine powder in the polymerization step (fine powder recycle step) and, optionally, water addition and/or partial drying after the polymerization, and/or the like. It is noted that, in this specification, the term "crosslinked hydrogel polymer that has not been subjected to gel-crushing" denotes a crosslinked hydrogel polymer immediately before being subjected to the gel-crushing step and may also be referred to as a "crosslinked hydrogel polymer subjected to gel-crushing".

The resin solid content of the crosslinked hydrogel polymer that has not been subjected to gel-crushing can be found from a drying loss as described in the section (f) of [1-3] mentioned earlier, after cutting and grain-refining the crosslinked hydrogel polymer that has not been subjected to gel-crushing into pieces 5 mm or less on a side, more preferably 1 mm to 3 mm on a side, with the use of scissors, a cutter, or the like. The gel grinding energy at the time of cutting using scissors, a cutter, or the like is substantially zero.

Furthermore, the moisture content of the crosslinked hydrogel polymer that has not been subjected to gel-crushing is 20 weight % to 90 weight %, more preferably 30 weight % to 90 weight %, even more preferably 40 weight % to 55 weight %.

(Inorganic Compound)

The water-absorbing resin powder in accordance with an embodiment of the present invention is preferably arranged such that some particles of the water-absorbing resin powder include an inorganic compound internally present therein. When particles include an inorganic compound therein, it is possible to reduce fine gel particles resulting from gel collapse that would occur when the water-absorbing resin powder swells into gel and thus possible to obtain water-absorbing resin powder having an excellent fluid retention capacity under pressure, an excellent water absorption speed, and an excellent liquid permeability.

The following substances, which are examples of the inorganic compound, also include substances that may be added as additives in an additive addition step subsequent to gel-crushing and drying in the production process of the water-absorbing resin. However, such additives, if added in the additive addition step in this manner, will stay at the surface of the water-absorbing resin and will not enter the inside of particles.

On the other hand, in the water-absorbing resin powder in accordance with an embodiment of the present invention, the inorganic compound is present inside the particles. Such a structure makes it possible to reduce fine gel particles resulting from gel collapse that would occur when the water-absorbing resin powder swells into gel and thus possible to obtain water-absorbing resin powder having a good fluid retention capacity under pressure, a good water absorption speed, and a good liquid permeability.

If the inorganic compound described below was added in the polymerization step, the inorganic compound would be uniformly distributed over the water-absorbing resin powder. However, in an embodiment of the present invention, the inorganic compound is added in the gel-crushing step and thereby the inorganic component is non-uniformly distributed over the water-absorbing resin powder. This arrangement also contributes to reducing fine gel particles resulting from gel collapse that would occur when the water-absorbing resin powder swells into gel and making it possible to obtain water-absorbing resin powder having a good fluid retention capacity under pressure, a good water absorption speed, and a good liquid permeability.

Inorganic particles may be suitably used as the inorganic compound.

Since the inorganic compound is present inside the particles of the water-absorbing resin powder, it is possible to reduce fine gel particles resulting from gel collapse that would occur when the water-absorbing resin powder absorbs water and swells into gel. In order to achieve this effect, it seems necessary that the inorganic compound exist at the interface between dry polymer particles which have become stuck together when dried. In order to achieve such a situation, it is most preferable to crush the gel in specific conditions in the presence of an inorganic compound (that is, by adding an inorganic compound during gel-crushing). On the other hand, for example, in another addition embodiment in which the inorganic compound is added to monomer before polymerization, the inorganic compound will be dispersed uniformly, which is not adequate. In a further addition embodiment in which the inorganic compound is added to dried, pulverized particles, the inorganic compound will stay only at the surfaces of the particles, which is not adequate. Another option is to add an inorganic compound when granulating dried particles with water or the like. However, this method is not adequate to obtain the effects of embodiments of the present invention for the following reasons: the particles have a low moisture content (gel is firm); pressure applied is small (particles are less likely to stick together); the surface area for sticking is very large; and the like.

Examples of the inorganic particles include minerals, polyvalent metal salts, polyvalent metal oxides, polyvalent metal hydroxides, oxide complexes, hydrotalcite-like compounds, and a combination of two or more of these.

More specifically, specific examples of the inorganic particles include: minerals such as talc, kaolin, fuller's earth, bentonite, activated clay, barite, naturally occurring asphaltum, strontium ore, ilmenite, and pearlite; aluminum compounds such as aluminum sulfate tetradeca-, pentadeca-, hexadeca-, heptadeca-, and octadecahydrates (or anhydrates), potassium aluminum sulfate dodecahydrate, aluminum sodium sulfate dodecahydrate, aluminum ammonium sulfate dodecahydrate, aluminum chloride, polyaluminum chloride, and aluminum oxide; other polyvalent metal salts, polyvalent metal oxides and polyvalent metal hydroxides; silicas such as hydrophilic amorphous silica (for example, dry method: Reolosil QS-20 available from Tokuyama Corporation, precipitation method: Sipernat 22S, Sipernat 2200 available from DEGUSSA); oxide complexes such as complexes of silicon oxide, aluminum oxide and magnesium oxide (for example, Attagel#50 available from ENGELHARD), complexes of silicon oxide and aluminum oxide, and complexes of silicon oxide and magnesium oxide; hydrotalcite-like compounds; and the like. Furthermore, the inorganic particles disclosed as examples in U.S. Pat. No. 5,164,459 and European Patent No. 761241 and the like may also be used. In an embodiment of the present invention, one kind of these inorganic particles may be used individually or two or more kinds of them may be used in combination.

The hydrotalcite-like compounds are multicomponent metal compounds having a hydrotalcite-like structure and containing divalent and trivalent metal cations and a hydroxyl group. Examples of the divalent metal cation include $mg^{2+}$, $Fe^{2+}$, $Zn^{2+}$, $Ca^{2+}$, $Ni^{2+}$, $Co^{2+}$, and $Cu^{2+}$, and, from the viewpoint of heat resistance and the like, $Mg^{2+}$ is more preferred. Examples of the trivalent metal cation include $Al^{3+}$, $Fe^{3+}$, and $Mn^{3+}$, and, from the viewpoint of heat resistance and the like, $Al^{3+}$ is more preferred. Therefore, more preferred hydrotalcite-like compounds are, for example, hydrotalcite-like compounds in which the divalent metal cation is magnesium cation and the trivalent metal cation is aluminum cation.

The hydrotalcite-like compound preferably has a hydrotalcite-like structure that is represented by the following general formula (1) and that is known as a structure of a layered compound:

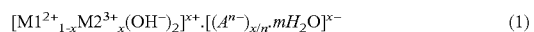

(1)

where $M1^{2+}$ represents a divalent metal cation, $M2^{3+}$ represents a trivalent metal cation, $A^{n-}$ represents an n– valent anion, and $H_2O$ represents water.

In regard to the proportions of the divalent and trivalent metal cations in the general formula (1), x is preferably 0.2 to 0.75, more preferably 0.25 to 0.70, even more preferably 0.25 to 0.50. Examples of the anion include $OH^-$, $F^-$, $Cl^-$, $Br^-$, $NO_3^-$, $CO_3^{2-}$, $SO_4^{2-}$, $Fe(CN)_6^{3-}$, $CH_3COO—$, oxalate ion, and salicylate ion, and a preferred anion is carbonate anion. Furthermore, m in the general formula (1) is a real number more than 0. It is more preferable that $0 < m \leq 10$.

The hydrotalcite-like compound may further have an organic compound intercalated between layers thereof and/or may be surface-treated so that the bindability with a water-absorbing resin improves.

More specific examples of the hydrotalcite-like compound include $Mg_6Al_2(OH)_{16}CO_3 \cdot 4H_2O$ and $Mg_4Al_2(OH)_{12}CO_3 \cdot 3H_2O$. DHT-4H and DHT-6 available from Kyowa Chemical Industry Co., Ltd., STABIACE HT-1-NC and STABIACE HT-P available from SAKAI CHEMICAL INDUSTRY CO., LTD., and the like may be suitably used.

The particle diameter of the inorganic particles for use in an embodiment of the present invention is, from the viewpoint of handleability and effects brought about by addition, preferably 500 μm or less, more preferably 100 μm or less, even more preferably 10 μm or less. As used herein, the term "particle diameter" includes the particle diameter of primary particles and the particle diameter of secondary particles (granulated material, aggregate). In a case of using particles of a compound that are firm and not easily broken from impact, such as unaggregated particles (primary particles) of silica or alumina, the particle diameter of the primary particles is preferably 5 μm or less, more preferably 1 μm or less, even more preferably 0.1 μm or less.

In a case where the inorganic particles are a hydrotalcite-like compound, the inorganic particles preferably have a specific particle size, and the volume average particle diameter is preferably 2 μm or less, more preferably 1.5 μm or less, even more preferably 1 μm or less. On the other hand, the volume average particle diameter is preferably 0.05 μm or more, more preferably 0.1 μm or more, even more preferably 0.3 μm or more. It is noted that the volume average particle diameter of a hydrotalcite-like compound can be determined by a "laser diffraction scattering method" (for example, determined using a particle size analyzer Microtrac MT3000II (product name) available from NIKKISO CO., LTD.). The average particle diameter of a hydrotalcite-like compound attached to the surface of a water-absorbing resin can be determined by a measurement method using a scanning electron microscope (SEM), which is the method described in Examples.

(Addition of Inorganic Compound)

In this step, an inorganic compound is added while the gel-crushing is performed. In an embodiment of the present invention, it is important to add an inorganic compound in the gel-crushing step. By doing so, the inorganic compound is kneaded into the particulate hydrogel and, when the obtained water-absorbing resin powder swells into gel, the gel is less likely to collapse and generates no or few fine gel particles. Therefore, polyacrylic acid (salt)-based water-absorbing resin powder obtained by the production method in accordance with an embodiment of the present invention has a good fluid retention capacity under pressure, a good water absorption speed, and a good liquid permeability.

The amount of the inorganic compound added is preferably 0.001 parts by weight to 5.0 parts by weight, more preferably 0.005 parts by weight to 1.0 part by weight, even more preferably 0.01 parts by weight to 0.5 parts by weight, particularly preferably 0.05 parts by weight to 0.2 parts by weight, relative to 100 parts by weight of the water-absorbing resin powder. The inorganic compound in an amount of 0.001 parts by weight or more is preferred, because this brings about the above-described effects of an embodiment of the present invention. The inorganic compound in an amount of 5.0 parts by weight or less is preferred, because the inorganic compound in such an amount is not excessive and the above-described effects are obtained.

A method of adding the inorganic compound is not limited to a particular kind, and is for example a method by which an inorganic compound in the form of a solution is added, a method by which an inorganic compound in the form of a dispersion liquid is added, a method by which an inorganic compound in the form of powder is added, or the like. Of these, from the viewpoint of kneading an inorganic compound into a particulate hydrogel, it is preferable to use a method by which an inorganic compound in the form of a solution is added or a method by which an inorganic compound in the form of a dispersion solution is added.

In a case where an inorganic compound in the form of a solution is added, the solvent is not limited to a particular kind and may be water or an organic solvent. Examples of the organic solvent include propylene glycol and 1,3-propanediol.

In a case where an inorganic compound in the form of a dispersion liquid is added, the dispersion medium is not limited to a particular kind and may be water or an organic dispersion medium. Examples of the organic dispersion medium include propylene glycol and 1,3-propanediol.

Of the methods listed above, a method by which an inorganic compound in the form of an aqueous solution is added and a method by which an inorganic compound in the form of an aqueous dispersion liquid is added are particularly preferred, because, with the use of water as a solvent or a dispersion medium, the inorganic compound is mixed uniformly and water can be easily removed by drying. It is assumed in an embodiment of the present invention that "water" includes at least one of the solid, liquid, and gaseous forms. From the viewpoint of handleability, "water" is more preferably in liquid form.

The concentration of a solution of the inorganic compound is not particularly limited as well, and the concentration of the inorganic compound in the solution is preferably 1 weight % to 70 weight %, more preferably 5 weight % to 50 weight %. The concentration of a dispersion liquid of the inorganic compound is not particularly limited as well, and the weight percentage of the inorganic compound in the dispersion liquid is preferably 1 weight % to 70 weight %, more preferably 5 weight % to 50 weight %.

There is no particular limitation on when to add the inorganic compound, provided that the inorganic compound is added while the crosslinked hydrogel polymer resides in a gel-crusher. However, it is preferable that the inorganic compound be fed concurrently with the crosslinked hydrogel polymer. It is more preferable that the feeding of the inorganic compound be performed downstream of where the crosslinked hydrogel polymer is fed (i.e., performed at a position closer to where crushed hydrogel is discharged).

In a case where the inorganic compound is added in the form of a solution or a dispersion liquid, the temperature of the solution or the dispersion liquid at the time of addition is preferably 10° C. to 95° C., more preferably 50° C. to 90° C.

(Addition of Water-absorbing Resin Fine Particles)

In an embodiment of the present invention, water-absorbing resin fine particles are added after the first gel-crushing step (preferably the gel-crushing that is performed concurrently with the progress of polymerization). The amount of the water-absorbing resin fine particles added is 10 weight % or more, preferably 12 weight % or more, more preferably 15 weight % or more, relative to the solid content of the gel. The upper limit is 30 weight %. When the amount of the water-absorbing resin fine particles added is over 30 weight %, performances of interest (e.g., SFC) may decrease.

(Gel-crusher)

A gel-crusher for use in the present step is not limited to a particular kind, and may be, for example: a batch-type or a continuous kneader, particularly a batch-type or a continuous dual-arm kneader or the like; a gel-crusher having a plurality of stirrer impellers; a screw extruder such as a single screw extruder, a twin screw extruder, or a meat chopper; or the like.

Of those listed above, the gel-crusher for use in the present step is more preferably a screw extruder, even more preferably a screw extruder having a porous plate at one end of the casing thereof. An example of such a screw extruder is the screw extruder disclosed in Japanese Patent Application Publication, Tokukai, No. 2000-63527. The following describes one example of a screw extruder for use in the present step.

A screw extruder for use in the present step is constituted by, for example, a casing, a table, a screw, a feed orifice, a hopper, a discharge orifice, a porous plate, a rotary blade, a ring, a backflow preventer, a motor, a ridge, and/or the like. The casing is in the form of a cylinder and has the screw therein. The casing has the discharge orifice at one end thereof, through which the crosslinked hydrogel polymer is extruded and subjected to gel-crushing, and has the porous plate placed short of the discharge orifice. The casing has, at the other end, the motor and a drive system and the like for rotation of the screw. There is the table under the casing and thereby the screw extruder can sit stably. The casing has, on the other hand, the feed orifice at the top thereof, through which the crosslinked hydrogel polymer is fed. The feed orifice is provided with the hopper for easy feeding of the crosslinked hydrogel polymer. The shape and size of the casing are not particularly limited, provided that the casing has an inner surface in the form of a cylinder that corresponds to the shape of the screw. The speed of the screw varies depending on the shape of the screw extruder and is not particularly limited, but is preferably adjustable as will be described later. Furthermore, for example, the screw extruder may include the backflow preventer near the discharge orifice and may have the ridge on the screw. The arrangements of these components, materials for these components, sizes of these components, materials for the backflow preventer and the rotary blades attached to the screw, and all other arrangements related to the screw extruder may be determined in accordance with the method disclosed in the above-mentioned Japanese Patent Application Publication, Tokukai, No. 2000-63527.

For example, the backflow preventer is not limited to a particular kind, provided that the backflow of the crosslinked hydrogel polymer at or near the discharge orifice is prevented by the structure of the backflow preventer. The backflow preventer is, for example, a ridge in the form of a spiral or ridges in the form of concentric circles on the inner wall of the casing, a linear, particulate, spherical, or angular projection parallel to the screw, or the like. When the pressure at or near the discharge orifice increases as the gel-crushing proceeds, the crosslinked hydrogel polymer tries to flow back toward the feed orifice. Providing the backflow preventer makes it possible to prevent the backflow of the crosslinked hydrogel polymer while performing gel-crushing of the crosslinked hydrogel polymer.

In regard to the porous plate at the exit of the casing of the gel-crusher, the thickness, pore diameter, and the open area of the porous plate may be selected as appropriate depending on the volume per unit time of the crosslinked hydrogel polymer crushed by the gel-crusher, the properties of the crosslinked hydrogel polymer, and the like and are not particularly limited. The thickness of the porous plate is preferably 3.5 mm to 40 mm, more preferably 6 mm to 20 mm. The pore diameter of the porous plate is preferably 3.2 mm to 24 mm, more preferably 7.5 mm to 24 mm. Furthermore, the open area of the porous plate is preferably 20% to 80%, more preferably within a range of 30% to 55%. It is noted that, in a case where a plurality of porous plates having different pore diameters (mm) are used, the simple average of the pore diameters of the porous plates is used as the pore diameter of the porous plates of the gel-crusher. The shape of the pore is preferably a circle. In a case where the shape of the pore is a shape other than a circle, such as a square, an oval, a slit, or the like, the area of the pore is converted into the area of a circle and this diameter of the circle is used as a pore diameter (mm).

If the thickness of the porous plate is less than 3.5 mm, the pore diameter of the porous plate is more than 24 mm, and/or the open area of the porous plate is more than 80%, such a porous plate may not be able to apply sufficient shearing and compressive forces to the crosslinked hydrogel polymer. On the contrary, if the thickness of the porous plate is more than 40 mm, the pore diameter of the porous plate is less than 3.2 mm, and/or the open area of the porous plate is less than 20%, such a porous plate may apply excessive shearing and compressive forces to the crosslinked hydrogel polymer, resulting in a reduction in physical properties of the crosslinked hydrogel polymer.

(Gel Grinding Energy (GGE)/Gel Grinding Energy (2) (GGE2))

In an embodiment of the present invention, in the gel-crushing step, the inorganic compound and/or the water-absorbing resin fine particles is/are added to the crosslinked hydrogel polymer having a resin solid content of 10 weight % or more and 80 weight % or less and gel-crushing that satisfies at least one of the above-mentioned (1) and (2) is performed.

In gel-crushing that satisfies the above-mentioned (1), the gel grinding energy (GGE) is controlled within a specified range. Specifically, the crosslinked hydrogel polymer is subjected to gel-crushing at a gel grinding energy (GGE) within a range of 18 J/g to 60 J/g.

In gel-crushing that satisfies the above-mentioned (2), the gel grinding energy (2) (GGE (2)) is controlled within a specified range. Specifically, the crosslinked hydrogel polymer is subjected to gel-crushing at a gel grinding energy (2) (GGE (2)) within a range of 9 J/g to 40 J/g.

It is noted that most of the existing gel-crushing techniques are to perform gel-crushing while minimizing shearing force, like those disclosed in U.S. Pat. Nos. 7,694,900, 6,565,768, and 6,140,395. However, an embodiment of the present invention includes applying a shearing force, which is equal to or greater than the existing techniques, to an extent such that the weight average molecular weight of the water-soluble component increases.

It is noted herein that the GGE can be controlled by, for example, the method shown in the earlier-described section [1-11].

The upper limit of the gel grinding energy (GGE) is preferably 60 J/g or less, more preferably 50 J/g or less, even more preferably 40 J/g or less, and the lower limit of the gel grinding energy (GGE) is preferably 18 J/g or more, more preferably 20 J/g or more, even more preferably 25 J/g or more. For example, in an embodiment of the present invention, the gel grinding energy (GGE) for gel-crushing of the crosslinked hydrogel polymer is preferably 18 J/g to 60 J/kg, more preferably 20 J/g to 50 J/g, even more preferably 25 J/g to 40 J/kg. By controlling the GGE within the above range, it is possible to perform gel-crushing while applying adequate shearing and compressive forces to the crosslinked hydrogel polymer. It is noted that the gel grinding energy (GGE) includes the energy that the gel-crusher consumes in the idle state.

In an embodiment of the present invention, the gel grinding energy for gel-crushing of the crosslinked hydrogel polymer may be alternatively specified by the gel grinding energy (2) (GGE(2)), which excludes the energy that the gel-crusher consumes in the idle state.

Specifically, in an embodiment of the present invention, the upper limit of the gel grinding energy (2) (GGE (2)) for gel-crushing of the crosslinked hydrogel polymer is preferably 40 J/g or less, more preferably 32 J/g or less, even more preferably 25 J/g or less, and the lower limit of the gel grinding energy (2) (GGE (2)) is preferably 9 J/g or more, more preferably 12 J/g or more, even more preferably 15 J/g or more. For example, in an embodiment of the present invention, the gel grinding energy (2) (GGE (2)) for gel-crushing of the crosslinked hydrogel polymer is preferably 9 J/g to 40 J/kg, more preferably 12 J/g to 32 J/g, even more preferably 15 J/g to 25 J/kg. By controlling the GGE (2) within the above range, it is possible to perform gel-crushing while applying adequate shearing and compressive forces to the crosslinked hydrogel polymer.

By drying, under specific conditions, the particulate crosslinked hydrogel polymer obtained in the gel-crushing step, it is possible to improve the shape of a water-absorbing resin and thus achieve both high liquid permeability and high water absorption speed. It is noted that, in a case where the gel-crushing is performed with the use of a plurality of crushers such as using a screw extruder after kneader polymerization or using a plurality of screw extruders, the sum of the energies consumed by the crushers is used as a gel grinding energy (GGE) or a gel grinding energy (2) (GGE (2)).

(Increase in Weight Average Molecular Weight of Water-soluble Component of Crosslinked Hydrogel Polymer)

The gel-crushing that satisfies the earlier-mentioned (3) includes performing gel-crushing so that the weight average molecular weight of the water-soluble component of the crosslinked hydrogel polymer increases by 10000 Da to 500000 Da. One way to achieve this is a production method by which the gel-crushing of the crosslinked hydrogel polymer is performed at a gel grinding energy (GGE) of 18 J/g to 60 J/g.

The gel Ext, i.e., the water-soluble content of the crosslinked hydrogel polymer that has not been subjected to gel-crushing, is preferably 0.1 weight % to 10 weight %, more preferably 0.5 weight % to 8 weight %, even more preferably 1 weight % to 5 weight %. In a case where the gel Ext is 10 weight % or less, the increase in weight average molecular weight of the water-soluble component resulting from shearing by gel-crushing is not excessive and therefore a desired liquid permeability is achieved. Although a smaller gel Ext is more preferred, the lower limit of the gel Ext is within the above range from the viewpoint of balancing with gel CRC, production cost necessary for reducing gel Ext, productivity reduction, and the like.

The gel Ext can be determined by the measurement method which will be described later in section (i) of [Examples], after cutting and grain-refining the crosslinked hydrogel polymer that has not been subjected to gel-crushing into pieces 5 mm or less on a side, preferably 1 mm to 3 mm on a side with the use of scissors, a cutter, or the like.

The weight average molecular weight of the water-soluble component of the crosslinked hydrogel polymer that has not been subjected to gel-crushing is preferably 50000 Da to 450000 Da, more preferably 100000 Da to 430000 Da, even more preferably 150000 Da to 400000 Da.

In a case where the weight average molecular weight of the water-soluble component is 50000 Da or more, the particle size of the particulate hydrogel resulting from gel-crushing does not become too small and therefore water-absorbing resin powder of desired physical properties is obtained. In a case where the weight average molecular weight of the water-soluble component is 450000 Da or less, there is a sufficient number of crosslinked points and thus the crosslinked hydrogel polymer is not unduly damaged from shearing, and therefore the water-soluble content does not increase much at gel-crushing and a high-performance water-absorbing resin is obtained. Such a weight average molecular weight of the water-soluble component can be controlled appropriately by controlling the amount of a crosslinking agent added during polymerization and the polymerization concentration and, in addition, if necessary, by use of, for example, a chain transfer agent.

The weight average molecular weight of the water-soluble component in the crosslinked hydrogel polymer that has not been subjected to gel-crushing can be determined by the measurement method which will be described later in section (j) of [Examples], after cutting and grain-refining the crosslinked hydrogel polymer that has not been subjected to gel-crushing into pieces 5 mm or less on a side, preferably 1 mm to 3 mm on a side with the use of scissors, a cutter, or the like.

On the other hand, the gel Ext of the particulate hydrogel that has been subjected to gel-crushing is preferably 0.1 weight % to 20 weight %, more preferably 0.1 weight % to 10 weight %, even more preferably 0.1 weight % to 8 weight %, particularly preferably 0.1 weight % to 5 weight %, relative to the resin solid content in the hydrogel. The increase in gel Ext of the particulate hydrogel from before to after gel-crushing is preferably 5 weight % or less, more preferably 4 weight % or less, even more preferably 3 weight % or less, particularly preferably 2 weight % or less, most preferably 1 weight % or less. The lower limit may be a negative value (for example, −3.0 weight % or −1.0 weight %), but is usually more than 0 weight %, preferably 0.1 weight % or more, more preferably 0.2 weight % or more, even more preferably 0.3 weight % or more. Specifically, gel-crushing may be performed until the gel Ext increases to an extent such that the increase falls within any selected range defined by the upper and lower limits described above, such as preferably 5.0 weight % or less, more preferably 0.1 weight % to 3.0 weight %.

In an embodiment of the present invention, the lower limit of the increase, which results from gel-crushing, in weight average molecular weight of the water-soluble component of the crosslinked hydrogel polymer is preferably 10000 Da or more, more preferably 20000 Da or more, even more preferably 30000 Da or more, and the upper limit of the increase is preferably 500000 Da or less, more preferably 400000 Da or less, even more preferably 250000 Da or less, particularly preferably 100000 Da or less. For example, in an embodiment of the present invention, the increase in weight average molecular weight of the water-soluble component of the particulate hydrogel from before to after gel-crushing of the crosslinked hydrogel polymer is preferably 10000 Da to 500000 Da, more preferably 20000 Da to 400000 Da, even more preferably 30000 Da to 250000 Da.

In a case of existing gel-crushing, the increase in weight average molecular weight of the water-soluble component is less than 10000 Da in many cases. In this regard, in an embodiment of the present invention, a larger amount of gel grinding energy (GGE), that is, larger amounts of shearing force and compressive force, are applied to the crosslinked hydrogel polymer and thereby the polymer main chains are broken and the weight average molecular weight of the water-soluble component increases greatly. However, the increase, resulting from gel-crushing, in weight average molecular weight of the water-soluble component is 500000 Da or less. This is preferred because the crosslinked hydrogel polymer does not experience excessive external mechanical force and therefore the increase in water-soluble component due to breakage of crosslinked polymer chains is not excessive, and thus physical properties do not deteriorate.

(Weight Average Particle Diameter (D50)/Logarithmic Standard Deviation ($\sigma\zeta$) of Particle Size Distribution)

Gel-crushing that satisfies the earlier-mentioned (4) and/or the earlier-mentioned (5) includes performing gel-crushing until the weight average particle diameter (D50) of the resulting particulate crosslinked hydrogel polymer falls within 350 μm to 2000 μm and/or the logarithmic standard deviation ($\sigma\zeta$) of a particle size distribution of the resulting particulate crosslinked hydrogel polymer falls within 0.2 to 1.0.

The crosslinked hydrogel polymer obtained in the polymerization step is crushed with the use of any of the earlier-described gel-crushers (kneader, meat chopper, screw extruder, or the like), with which the gel-crushing of an embodiment of the present invention is performed, into a particulate crosslinked hydrogel polymer. It is noted that the particle size of the particulate crosslinked hydrogel polymer may be controlled alternatively by classification, blending, or the like, but is preferably controlled by gel-crushing.

The weight average particle diameter (D50) (determined by sieve classification) of the particulate hydrogel resulting from gel-crushing is 350 μm to 2000 μm, more preferably 400 μm to 1500 μm, even more preferably 500 μm to 1000 μm. The logarithmic standard deviation ($\sigma\zeta$) of a particle size distribution of the particulate hydrogel is 0.2 to 1.0, more preferably 0.2 to 0.8, even more preferably thought to be 0.2 to 0.7.

In a case where the weight average particle diameter is 2000 μm or less, the crosslinked hydrogel polymer receives uniform and sufficient shearing and compressive forces and therefore such a case is preferred.

Furthermore, in the case where the weight average particle diameter is 2000 μm or less, the degree of dryness does not differ greatly between the inside and the surface of the crosslinked hydrogel polymer and therefore particles with uneven physical properties are unlikely to form from pulverization after drying, which prevents deterioration of physical properties that would otherwise result from such uneven particles. On the other hand, in a case where the weight average particle diameter is 350 μm or more, the surface area of the crosslinked hydrogel polymer does not become too large and thus excessive dryness is not likely to occur, resulting in sufficient reduction in residual monomers in the drying step. Furthermore, the amount of fine powder resulting from the pulverization of the dried polymer is reduced, and therefore the particle size is easily controlled and also the physical properties such as liquid permeability (SFC) become excellent. It is noted that a normal gel-crushing operation alone may not be enough to perform gel-crushing until the weight average particle diameter of the crosslinked hydrogel polymer reaches less than 350 μm and that some other special operation, such as classification of crushed gel (e.g., Japanese Patent Application Publication, Tokukaihei, No. 6-107800 etc.) or particle size control during polymerization prior to gel-crushing (e.g., method of obtaining gel particles having a sharp particle size distribution by reversed phase suspension polymerization; European Patent No. 0349240 etc.) is needed. The use of the above-mentioned special method in addition to gel-crushing necessitates, for example, a large amount of surfactant and organic solvent for polymerization and classification and causes a reduction in productivity (increase in cost) and deterioration of physical properties (an increase in residual monomers, an increase in fine powder). This leads to a new problem. Therefore, a particulate hydrogel having a weight average particle diameter less than 350 μm is not only difficult to obtain but also is not preferred.

Furthermore, although a smaller logarithmic standard deviation ($\sigma\zeta$) is more preferred from the viewpoint of obtaining more uniform dryness, as with the case with the weight average particle diameter, in order to obtain a logarithmic standard deviation ($\sigma\zeta$) less than 0.2, a special operation such as classification of crushed gel, particle size control during polymerization prior to gel-crushing, or the like is needed. Therefore, in consideration of productivity and cost, a particulate hydrogel having a logarithmic standard deviation ($\sigma\zeta$) less than 0.2 is not preferred and is substantially not obtainable. One way to control the particle size as described above is gel-crushing of an embodiment of the present invention. The gel-crushing may be performed especially with the use of a screw extruder under conditions such that the above-described particle size is obtained.

(Polymerization Rate of Crosslinked Hydrogel Polymer that has not been Subjected to Gel-crushing)

In an embodiment of the present invention, the gel-crushing is performed during polymerization or after polymerization. The gel-crushing is performed more preferably with respect to the polymerized, crosslinked hydrogel polymer. The polymerization rate of the crosslinked hydrogel polymer subjected to gel-crushing is preferably 90 mol % or more, more preferably 93 mol % or more, even more preferably 95 mol % or more, particularly preferably 97 mol % or more. The upper limit is preferably 99.5 mol %. The crosslinked hydrogel polymer subjected to gel-crushing having a polymerization rate of preferably 90 mol % or more is preferred, because residual monomers contained in the resulting water-absorbing resin powder become small in number.

As used herein, the polymerization rate, which is also referred to as conversion rate, means a value calculated from polymer content calculated from pH titration of the crosslinked hydrogel polymer and residual monomer content.

The polymerization rate of the crosslinked hydrogel polymer subjected to gel-crushing preferably falls within the above range. However, in a case where gel-crushing is performed during polymerization, such as performing kneader polymerization, it is assumed that the gel-crushing step starts when the aqueous monomer solution has turned into a "sufficiently gelled state".

For example, in a case where the kneader polymerization is employed, the aqueous monomer solution changes into a crosslinked hydrogel polymer as polymerization progresses. Specifically, an aqueous monomer solution is stirred at the initiation of polymerization, a crosslinked hydrogel polymer having a certain viscosity and a low degree of polymerization is stirred during polymerization, gel-crushing of part of the crosslinked hydrogel polymer starts as the polymerization progresses, and gel-crushing is performed in the last half or in the final stage of the polymerization, sequentially in a single region. Therefore, for clear distinction between "stirring of an aqueous monomer solution" at the initiation of the polymerization and "gel-crushing" in the final stage of the polymerization, it is judged that a transition to the gel-crushing step has occurred when the "sufficiently gelled state" is reached.

The term "sufficiently gelled state" denotes a state in which the crosslinked hydrogel polymer can be grain-refined by applying shearing force and which occurs when or after the maximum polymerization temperature (polymerization peak temperature) is reached. The term "sufficiently gelled state" also denotes a state in which the crosslinked hydrogel polymer can be grain-refined by applying shearing force and which occurs when or after the polymerization rate of monomers in the aqueous monomer solution reaches preferably 90 mol % or more, more preferably 93 mol % or more, even more preferably 95 mol % or more, particularly preferably 97 mol % or more. That is, in the gel-crushing step of an embodiment of the present invention, a crosslinked hydrogel polymer having a monomer polymerization rate falling within the above range is subjected to the gel-crushing. It is noted that, in a case of a polymerization reaction that shows no polymerization peak temperature (for example, in a case where entire polymerization proceeds at constant temperature, a case where the polymerization temperature continues to rise, or the like), the "sufficiently gelled state" is defined by the above-described monomer polymerization rate.

Therefore, in a case where batch-type kneader polymerization is employed, the GGE may be measured when or after the polymerization peak temperature is reached or when or after the above conversion rate is reached in the kneader polymerization. In a case where continuous kneader polymerization is used, the GGE is found by multiplying "the total GGE for the entire polymerization step" by "the ratio of the amount of polymerization time after the polymerization peak temperature is reached to the total amount of polymerization time" or by "the ratio of the amount of polymerization time after the above conversion rate is reached to the total amount of polymerization time" (refer to Equation (3)).

GGE[J/g]=(total GGE)×(amount of polymerization time after polymerization peak temperature is reached or after conversion rate is reached)/ (total amount of polymerization time)　　Equation (3)

It is noted that, even in a case where a batch-type or a continuous kneader polymerizer is employed as described above, another gel-crushing may be performed after the kneader polymerization. In this case, the sum of the energy consumed by an apparatus that performs such another gel-crushing and the GGE or GGE (2) for the above-described kneader polymerization is used for evaluation of the GGE or GGE (2) of an embodiment of the present invention.

In a case where the polymerization step is performed by belt polymerization, a crosslinked hydrogel polymer may be chopped or broken during or after polymerization, preferably after polymerization, to a size of about several tens of centimeters prior to the gel-crushing. This operation makes it easily to feed the crosslinked hydrogel polymer into the gel-crusher and thus possible to more smoothly perform the gel-crushing step. It is noted that the chopping or breaking is preferably performed by a method that enables chopping or breaking of the crosslinked hydrogel polymer without kneading the crosslinked hydrogel polymer, and is, for example, chopping or breaking or the like using a guillotine cutter. The size and shape of the chopped or broken crosslinked hydrogel polymer are not particularly limited, provided that the crosslinked hydrogel polymer can be fed into the gel-crusher. Furthermore, in a case where the weight of each gel piece resulting from breaking is one-tenth or less of "the weight of a crosslinked hydrogel polymer fed into the gel-crusher per second", the energy used for the breaking is also included in the GGE for crushing.

(Operating Conditions of Gel-crusher)

In a case where the gel-crusher for use in the gel-crushing step of an embodiment of the present invention is a screw extruder, the rotation speed of a screw shaft of the screw extruder cannot be specified by a particular value because the peripheral speed of the impeller blades varies depending on the inner diameter of the casing of the screw extruder. The shaft rotation speed is preferably 90 rpm to 500 rpm, more preferably 100 rpm to 400 pm, even more preferably 120 rpm to 200 rpm. In a case where the shaft rotation speed is 90 rpm or more, shearing and compressing forces necessary for gel-crushing are achieved. In a case where the shaft rotation speed is 500 rpm or less, the shearing and compressive forces applied to the crosslinked hydrogel polymer are not excessive and therefore physical properties are not likely to deteriorate, and the gel-crusher does not experience large load and thus is not prone to breakage. Furthermore, the peripheral speed of the impeller blades at this time is preferably 0.5 m/s to 5 m/s, more preferably 0.5 m/s to 4 m/s. The temperature of the gel-crusher in an embodiment of the present invention is raised to or maintained at preferably 40° C. to 120° C., more preferably 60° C. to 100° C., for prevention of adhesion or the like of the crosslinked hydrogel polymer.

(Gel Temperature)

Gel temperature, specifically, the temperature of a crosslinked hydrogel polymer that has not been subjected to gel-crushing, is preferably 40° C. to 120° C., more preferably 60° C. to 120° C., even more preferably 60° C. to 110° C., particularly preferably 65° C. to 110° C., from the viewpoint of particle size control and physical properties. In a case where the gel temperature is 40° C. or above, the crosslinked hydrogel polymer is less likely to become firm because of its characteristics and thus the particle shape and particle size distribution are easy to control when gel-crushing is performed. In a case where the gel temperature is 120° C. or below, on the contrary, the crosslinked hydrogel polymer does not become too soft, and therefore the particle shape and particle size distribution are easy to control. Such a gel temperature can be controlled appropriately by polymerization temperature, heating after polymerization, heat retention after polymerization, cooling after polymerization, or the like.

(Gel CRC)

The gel CRC of a crosslinked hydrogel polymer that has not been subjected to gel-crushing is preferably 10 g/g to 35 g/g, more preferably 10 g/g to 32 g/g, even more preferably 10 g/g to 30 g/g, particularly preferably 15 g/g to 30 g/g. In a case where the gel CRC is 10 g/g to 35 g/g, particle shape and particle size distribution are easy to control when gel-crushing is performed, and thus such a case is preferred. Such a gel CRC can be appropriately controlled by the amount of a crosslinking agent added during polymerization and other parameters such as polymerization concentration. It is noted that it is well known that a water absorbent resin having a high CRC is preferred. It was, however, found that, in a case where the gel CRC is more than 35 g/g, it may be difficult to control particle shape and particle size distribution.

The gel CRC is determined by the measurement method which will be described later in section (g) of [Examples], after cutting and grain-refining the crosslinked hydrogel polymer that has not been subjected to gel-crushing into pieces 5 mm or less on a side, more preferably 1 mm to 3 mm on a side with the use of scissors, a cutter, or the like.

The gel CRC of a particulate hydrogel resulting from gel-crushing is preferably 10 g/g to 35 g/g, more preferably 10 g/g to 32 g/g, even more preferably 15 g/g to 30 g/g. It is noted that the gel CRC after gel-crushing, relative to the gel CRC before gel-crushing, is preferably −1 g/g to +3 g/g, more preferably 0.1 g/g to 2 g/g, even more preferably 0.3 g/g to 1.5 g/g.

(Resin Solid Content after Gel-crushing)

In an embodiment of the present invention, the resin solid content of a particulate hydrogel resulting from gel-crushing is, from the viewpoint of physical properties, preferably 10 weight % to 80 weight %, more preferably 30 weight % to 80 weight %, even more preferably 50 weight % to 80 weight %. It is preferable that the resin solid content of the particulate hydrogel resulting from gel-crushing fall within the above range, because an increase in CRC due to drying is easy to control and damage caused by drying (for example, increase in water-soluble component) is small. It is noted that the resin solid content after gel-crushing can be appropriately controlled by, for example, the resin solid content before gel-crushing, water added when necessary, and water vaporization by heating during gel-crushing.

(Number of Samples Subjected to Measurement)

In order to evaluate the physical properties of a crosslinked hydrogel polymer that has not been subjected to gel-crushing or the physical properties of a particulate hydrogel resulting from gel-crushing, it is necessary to sample a necessary amount from a production apparatus and measure the sample at necessary frequency. In an embodiment of the present invention, evaluations are performed on the basis of the weight average molecular weight of the water-soluble component of a crosslinked hydrogel polymer that has not been subjected to gel-crushing. The value of the weight average molecular weight should be a fully averaged value. In this regard, in a case where, for example, continuous gel-crushing using a continuous kneader, a meat chopper or the like is used to produce water-absorbing resin powder in an amount of 1 t/hr to 20 t/hr or 1 t/hr to 10 t/hr, two or more samples per 100 kg of the crosslinked hydrogel polymer, at least ten samples in total, may be sampled and subjected to the measurement. In a case of batch-type gel-crushing (for example, batch-type kneader), at least ten samples may be sampled from batch samples and subjected to the measurement to evaluate the physical properties of the particulate hydrogel.

(Use of Water)

In the gel-crushing step of an embodiment of the present invention, water may be added to a crosslinked hydrogel polymer before subjecting the crosslinked hydrogel polymer to gel-crushing. It is assumed in an embodiment of the present invention that "water" includes at least one of the solid, liquid, and gaseous forms.

How and when water is added are not particularly limited, provided that water is fed to the gel-crusher while a crosslinked hydrogel polymer resides in the gel-crusher. Alternatively, a crosslinked hydrogel polymer to which water has been added may be fed into the gel-crusher. Furthermore, the water is not limited to "water alone" and may be in the form of a mixture of water and another additive (for example, surfactant, base for neutralization) or a solvent other than water. However, in this case, the water content is preferably 90 weight % to 100 weight %, more preferably 99 weight % to 100 weight %, even more preferably substantially 100 weight %.

In an embodiment of the present invention, the water in at least one of the solid, liquid, and gaseous forms may be used, but the water in liquid and/or gaseous form is preferred from the viewpoint of handleability. The amount of water fed is preferably more than 0 parts by weight and 4 parts by weight or less, more preferably more than 0 parts by weight and 2 parts by weight or less, relative to 100 parts by weight of the crosslinked hydrogel polymer. In a case where the amount of the water fed is more than 4 parts by weight, this may cause some problems such as undried materials left undried even after drying.

In a case where the water is fed in liquid form, the temperature of the water when fed is preferably 10° C. to 100° C., more preferably 40° C. to 100° C. In a case where the water is fed in gaseous form, the temperature of the water fed is preferably 100° C. to 220°, more preferably 100° C. to 160° C., even more preferably 100° C. to 130° C. It is noted that, when water is fed in gaseous form, a method of preparing the water in gaseous form is not particularly limited. The water in gaseous form may be prepared by, for example: a method using water vapor generated from heat made by a boiler; a method using water in gaseous form released from the surface of water ultrasonically vibrated; or the like. In an embodiment of the present invention, in a case where water is fed in gaseous form, the water is preferably water vapor with higher pressure than atmospheric pressure, more preferably water vapor generated by a boiler.

(Use of Additive)

As described earlier, it is preferable to perform gel-crushing of a crosslinked hydrogel polymer to which water has been added. In doing so, some other additive other than water, such as a neutralizer, may be added and kneaded into the crosslinked hydrogel polymer before gel-crushing. The water-absorbing resin thus obtained may further be modified. Specifically, when gel-crushing is performed, an aqueous solution containing a basic substance described in section [3-1] (for example, a 10 weight % to 50 weight % sodium hydroxide aqueous solution) may be added to cause neutralization (particularly within the range of the neutralization rate described earlier). Furthermore, a polymerization initiator, a reducing agent, and/or a chelating agent may be added and mixed in an amount of 0.001 weight % to 3 weight % (relative to resin solid content) when gel-crushing is performed, thereby reducing residual monomers, improving color, and/or imparting durability.

[3-3] Drying Step

The drying step in an embodiment of the present invention is a step of drying the particulate hydrogel obtained in the gel-crushing step to obtain a dried polymer. More specifically, the drying step is a step of drying the particulate crosslinked hydrogel polymer obtained in the gel-crushing step with the use of a dryer at a drying temperature of 150° C. to 250° C. to obtain a dried polymer.

The following describes a drying method suitable for use in an embodiment of the present invention.

A drying method that can be used in the drying step of an embodiment of the present invention is, for example, drying by heating, hot air drying, drying under reduced pressure, infrared drying, microwave drying, drum dryer dying, drying by azeotropic dehydration with hydrophobic organic solvent, high-humidity drying using hot water vapor, or the like. Of these, hot air drying is preferred, and hot air drying in which a dew point is preferably 40° C. to 100° C., more preferably 50° C. to 90° C., is more preferred.

A dryer that can be used in the drying step of an embodiment of the present invention is, for example, a heat transfer dryer, a heat radiating dryer, a hot air heat transfer dryer, a dielectric heating dryer, or the like. One of these dryers may be used individually or two or more of the dryers may be used in combination. Of these, a hot air heat transfer dryer, that is, a hot air dryer, is preferred, from the viewpoint of drying speed. It is noted that the hot air dryer may be, for example, a through-flow belt hot air dryer, a through-flow circuit hot air dryer, a vertical through-flow hot air dryer, a parallel through-flow belt hot air dryer, a through-flow tunnel hot air dryer, a through-flow groove stirring hot air dryer, a fluidized-bed hot air dryer, a flash hot air dryer, a spray hot air dryer, or the like. In an embodiment of the present invention, a through-flow belt hot air dryer is preferably used from the viewpoint of physical property control.

In an embodiment of the present invention, the particulate hydrogel may be dried by any of the various drying methods described above. In a more preferred aspect, a through-flow belt hot air dryer is preferably used. In a case where a through-flow belt hot air dryer is used, the hot air in the dryer should flow perpendicularly to a layer of the particulate hydrogel placed and left to stand on the through-flow belt (for example, air flowing upward and downward, air flowing upward, or air flowing downward). By using a through-flow belt hot air dryer and using hot air flowing perpendicularly to the particulate hydrogel, it is possible to dry the particulate hydrogel in a uniform manner and thus possible to obtain a water-absorbing resin having excellent physical properties such as excellent liquid permeability. It is noted that the term "perpendicularly" or "perpendicular" described above denotes a state in which hot air flows through the layer of the particulate hydrogel (layer of particulate hydrogel 10 mm to 300 mm in thickness placed on a perforated metal or a metal gauge) upward and/or downward (flows through the layer of the particulate hydrogel from top to bottom, and/or from bottom to top), and is not limited to the exact perpendicular direction, provided that the hot air flows through the layer upward and/or downward. For example, hot air flowing at an angle may be used. In this case, hot air flowing at an angle of 30° or less, more preferably 20° or less, even more preferably 10° or less, particularly preferably 5° or less, most preferably 0° to the perpendicular direction is used.

It is noted that, in a case were gel-crushing that satisfies the earlier-described (4) and/or (5) is performed, it is preferable that, in the drying step, the resin solid content of a polymer in the form of a particulate hydrogel when the polymer is fed into a through-flow belt hot air dryer be 10 weight % to 80 weight %, the drying temperature of the through-flow belt hot air dryer be 150° C. to 250° C., and the air velocity of the hot air in the perpendicular direction be 0.8 m/s to 2.5 m/s.

The following describes drying conditions and the like of the drying step of an embodiment of the present invention. By performing drying under the following drying conditions, it is possible to improve the liquid permeability and water absorption speed of water-absorbing resin powder that is obtained by surface-treating the resulting dried polymer.

(Drying Temperature)

The drying temperature in the present step is 150° C. to 250° C., more preferably 160° C. to 220° C., even more preferably 170° C. to 200° C. A drying temperature of 150° C. to 250° C. makes it possible to shorten drying time and also reduce coloration of the resulting dried polymer. At such a drying temperature, the liquid permeability and water absorption speed of the resulting water-absorbing resin powder also tend to improve. It is noted that a drying temperature of 250° C. or below prevents or reduces damage to polymer chains and thus makes it possible to reduce deterioration of physical properties. Furthermore, a drying temperature of 150° C. or above improves water absorption speed, and reduces undried products left undried and thus prevents clogging that would be caused by the undried products during the subsequent pulverizing step.

(Drying Time)

The drying time in the present step depends on the surface area of a particulate hydrogel, type of dryer, and the like, and therefore may be selected appropriately in a manner such that a target moisture content is achieved. The drying time is normally preferably 1 minute to 10 hours, more preferably 5 minutes to 2 hours, even more preferably 10 minutes to 120 minutes, particularly preferably 20 minutes to 60 minutes.

Furthermore, the time taken by the particulate hydrogel to proceed from the end of the gel-crushing step of the earlier-described section [3-2] to the start of the drying step, specifically, the time taken by the particulate hydrogel to travel from the exit of the gel-crusher to the entrance of the dryer, is preferably short, from the viewpoint of coloration of the water-absorbing resin powder. Specifically, such time is preferably 2 hours or less, more preferably 1 hour or less, even more preferably 30 minutes or less, particularly preferably 10 minutes or less, most preferably 2 minutes or less.

(Air Velocity)

In a case where a through-flow belt hot air dryer is used as a dryer in the present step, the air velocity of the hot air in a perpendicular direction (upward and/or downward) is preferably 0.8 m/s to 2.5 m/s, more preferably 1.0 m/s to 2.0 m/s. An air velocity of 0.8 m/s or more shortens the drying time and improves liquid permeability and water absorption speed of the resulting water-absorbing resin powder. Furthermore, an air velocity of 2.5 m/s or less makes it possible to perform drying in a uniform manner and makes it easy to control the moisture content of the resulting dried polymer within a desired range. It is noted that the air velocity is, for example, in a case of a through-flow belt hot air dryer, represented as the mean flow velocity of the hot air flowing through a horizontally moving band face in a direction perpendicular to the band face. Therefore, the mean flow velocity of the hot air may be found by dividing the air volume of the through-flow belt hot air dryer by the area of the through-flow belt.

It is noted that the air velocity may be controlled so as not to impair the effects of an embodiment of the present invention. For example, the air velocity may be controlled during 70% or more, preferably 90% or more, even more preferably 95% or more, of the drying time.

The particulate hydrogel having a specific particle size, which was obtained in the gel-crushing step, is dried with a through-flow belt hot air dryer having a specific temperature and a specific air velocity, and thereby the liquid permeability and water absorption speed of the water-absorbing resin powder are improved. That is, when the air velocity of the hot air falls within the above-described range, the water absorption speed of the resulting dried polymer improves.

(Dew Point of Hot Air)

In a case where a through-flow belt hot air dryer is used as a dryer in the present step, the hot air used in the through-flow belt hot air dryer at least contains water vapor and has a dew point of preferably 30° C. to 100° C., more preferably 30° C. to 80° C. When the dew point of the hot air is controlled within the above-described range and more preferably the particle size of the particulate hydrogel is controlled within the earlier-described range, it is possible to reduce residual monomers and also prevent a reduction in bulk specific gravity of the dried polymer. It is assumed that the dew point is that at the time when a particulate hydrogel has a moisture content of at least 10 weight % or more, preferably 20 weight % or more.

Furthermore, in the present step, from the view point of reducing residual monomers, improving water absorption performance, reducing coloration, and the like, it is preferable that the dew point at or near the entrance of the dryer (or a dew point in the initial stage of the drying, for example, when or before the drying time reaches 50%) be higher than the dew point at or near the exit of the dryer (or a dew point in the final stage of the drying, for example, when or after the drying time reaches 50%). Specifically, it is preferable that, at or near the entrance of the dryer, the hot air having a dew point preferably 10° C. to 50° C. above, more preferably 15° C. to 40° C. above the dew point at or near the exit of the dryer be brought into contact with the particulate hydrogel. When the dew point is controlled within the above range, it is possible to prevent a reduction in bulk specific gravity of the dried polymer.

In a case where a through-flow belt hot air dryer is used as a dryer to dry a particulate hydrogel in the present step, it is preferable that the particulate hydrogel be continuously fed so that the particulate hydrogel forms a layer on the belt of the through-flow belt hot air dryer and be hot-air dried. The width of the belt of the through-flow belt hot air dryer used here is not particularly limited and preferably 0.5 m or more, more preferably 1 m or more. The upper limit of the width is preferably 10 m or less, more preferably 5 m or less. Furthermore, the length of the belt is preferably 20 m or more, more preferably 40 m or more. The upper limit of the length is preferably 100 m or less, more preferably 50 m or less.

Furthermore, from the viewpoint of drying efficiency, the particulate hydrogel on the belt has a layer length (thickness of the gel layer) of preferably 10 mm to 300 mm, more preferably 50 mm to 200 mm, even more preferably 80 mm to 150 mm, particularly preferably 90 mm to 110 mm.

Furthermore, the speed of travel of the particulate hydrogel on the belt may be selected appropriately depending on the belt width, belt length, production volume, drying time, and the like, but, from the view point of a load on a belt drive device and durability of the device, is preferably 0.3 m/min to 5 m/min, more preferably 0.5 m/min to 2.5 m/min, even more preferably 0.5 m/min to 2 m/min, particularly preferably 0.7 m/min to 1.5 m/min.

The method for producing polyacrylic acid (salt)-based water-absorbing resin powder in accordance with an embodiment of the present invention is more suitable for continuous operation. When the above-described various conditions for the drying step fall within the above-described ranges, the method shows remarkable effects of improving productivity, physical properties of the resulting water-absorbing resin powder, and the like.

In achieving an embodiment of the present invention, it is further preferable that the drying temperature, dew point of hot air, and air volume vary in steps. Therefore, it is more preferable that the dryer be a through-flow belt hot air dryer having preferably five or more chambers, more preferably six or more chambers, even more preferably eight or more chambers. The upper limit is selected appropriately depending on the size of the apparatus such as production volume, but is normally about twenty chambers.

(Resin Solid Content)

The particulate hydrogel obtained in the gel-crushing step is dried in the present drying step to obtain a dried polymer. The resin solid content of the dried polymer, which is found from drying loss (drying loss after 1 g of powder is heated at 180° C. for 3 hours to dryness), is preferably more than 80 weight %, more preferably 85 weight % to 99 weight %, even more preferably 90 weight % to 98 weight %, particularly preferably 92 weight % to 97 weight %.

(Surface Temperature of Particulate Hydrogel)

Immediately before being introduced into the dryer, the particulate hydrogel obtained in the gel-crushing step has a surface temperature of preferably 40° C. to 110° C., more preferably 60° C. to 110° C., even more preferably 60° C. to 100° C., particularly preferably 70° C. to 100° C. A surface temperature of 40° C. or above is preferred, because balloon-like dried materials do not form during drying, no or little fine powder generates during pulverization, and therefore physical properties do not deteriorate. A surface temperature of 110° C. or below is preferred, because the dried water-absorbing resin does not undergo deterioration (e.g., increase in water-soluble component or the like) or coloration.

[3-4] Pulverizing Step and Classification Step

The present steps are steps of pulverizing and classifying the dried polymer obtained in the drying step to obtain water-absorbing resin powder that is to be subjected to a surface treatment step. It is noted that the present steps are different from the earlier-described "[3-2] Gel-crushing step" in resin solid content at the time of pulverization (crushing), particularly different in that a target to be pulverized has already been subjected to the drying step (preferably dried to have the resin solid content described earlier). The water-absorbing resin powder obtained through the pulverizing step may be referred to as a pulverized substance.

The dried polymer obtained in the drying step may be used "as-is" as a water-absorbing resin. However, the dried polymer is preferably surface-treated, particularly preferably surface-crosslinked, in the surface treatment step described later, and, for achieving improved physical properties in the surface treatment step, is more preferably controlled to have a specific particle size. The particle size control may be performed appropriately not only in the present pulverizing step and classification step but also in the polymerization step, a fine powder recycling step, a granulation step, and/or the like. As described earlier, the particle size is defined using standard sieves (JIS Z 8801-1 (2000)).

A pulverizer that can be used in the pulverizing step is not limited to a particular kind, and is, for example, a vibration mill, a roll granulator, a knuckle-type pulverizer, a roll mill, a high-speed rotation pulverizer (such as a pin mill, a hammer mill, or a screw mill), a cylindrical mixer, or the like. Of these pulverizers, it is more preferable to use a multi-tier roll mill or roll granulator from the viewpoint of particle size control.

The classification step includes performing a classification operation so as to achieve the following particle size. In a case where surface crosslinking is performed, the classification operation is preferably performed before the surface-crosslinking step (such classification is a first classification step). Another classification operation may also be performed after the surface crosslinking (such classification is a second classification step).

The classification operation is not particularly limited. In a case of sieving using sieves, the classification is performed in the following manner. That is, in a case where a target particle size distribution of water-absorbing resin powder is 150 μm or more and less than 850 μm, for example, first, the pulverized substance is sieved using a sieve with a mesh size of 850 μm, and the portion that has passed through the sieve is further sieved using a sieve with a mesh size of 150 μm. Then, the portion remaining on the sieve with a mesh size of 150 μm is the water-absorbing resin powder having the desired particle size distribution. Instead of sieve classification, some other classifier such as an air sifter may be used.

The above classification step may be used also to cause water-absorbing resin powder in accordance with an embodiment of the present invention to satisfy the condition "the percentage of water-absorbing resin powder having a particle size of 150 μm or more and less than 850 μm is 90 weight % or more".

[3-5] Surface Treatment Step

The method for producing polyacrylic acid (salt)-based water-absorbing resin powder in accordance with an embodiment of the present invention preferably further includes a surface treatment step to improve water absorption performance (absorbability under pressure, liquid permeability, absorption speed, and the like). The surface treatment step includes a surface-crosslinking step using a known surface-crosslinking agent and a known surface-crosslinking method and, optionally, further includes some other addition step.

(Surface-crosslinking Agent)

The water-absorbing resin powder in accordance with an embodiment of the present invention is more preferably surface-crosslinked. The surface crosslinking may be performed using a known surface-crosslinking agent and a known surface-crosslinking method.

Examples of the surface-crosslinking agent include various organic surface-crosslinking agents and inorganic surface-crosslinking agents. Organic covalently bonding surface-crosslinking agents are more preferred. Examples of covalently bonding surface-crosslinking agents include polyhydric alcohol compounds, epoxy compounds, polyamine compounds, products of condensation of polyamine and haloepoxy compounds, oxazoline compounds, (mono-, di-, or poly-)oxazolidinone compounds, and alkylene carbonate compounds.

In particular, dehydration crosslinking agents composed of a polyhydric alcohol compound, an alkylene carbonate compound, and/or an oxazolidinone compound, which require high temperature to react, may be used. More specific examples of dehydration crosslinking agents include the compounds disclosed in U.S. Pat. Nos. 6,228,930, 6,071,976, 6,254,990, and the like.

More specific examples of the covalently bonding surface-crosslinking agents include polyhydric alcohol compounds such as mono-, di-, tri-, or tetra-propylene glycol, 1,3-propanediol, glycerin, 1,4-butanediol, 1,3-butanediol, 1,5-pentanediol, 1,6-hexanediol, and sorbitol; epoxy compounds such as ethylene glycol diglycidyl ether and glycidol; alkylene carbonate compounds such as ethylene carbonate; oxetane compounds; and cyclic urea compounds such as 2-imidazolidinone.

The amount of the surface-crosslinking agent used is preferably 0.001 parts by weight to 10 parts by weight, more preferably 0.01 to 5 parts by weight, relative to 100 parts by weight of the water-absorbing resin powder subjected to surface crosslinking. It is preferable that water be used in combination with the surface-crosslinking agent. The amount of water used is preferably 0.5 parts by weight to 20 parts by weight, more preferably 0.5 parts by weight to 10 parts by weight, relative to 100 parts by weight of the water-absorbing resin powder subjected to surface crosslinking. Also in a case where an inorganic surface-crosslinking agent and an organic surface-crosslinking agent are used in combination, the amount of each surface-crosslinking agent is preferably 0.001 parts by weight to 10 parts by weight, more preferably 0.01 parts by weight to 5 parts by weight, relative to 100 parts by weight of the water-absorbing resin powder subjected to surface crosslinking.

A hydrophilic organic solvent may also be used here. The amount of the hydrophilic organic solvent used is preferably more than 0 parts by weight and 10 parts by weight or less, more preferably more than 0 parts by weight and 5 parts by weight or less, relative to 100 parts by weight of the water-absorbing resin powder subjected to surface crosslinking. In addition, when a crosslinking agent solution is mixed into the water-absorbing resin powder that is to be subjected to surface crosslinking, water-insoluble fine particle powder and/or a surfactant may coexist in an amount that does not impair the effects of an embodiment of the present invention, e.g., in an amount of preferably more than 0 parts by weight and 10 parts by weight or less, more preferably more than 0 parts by weight and 5 parts by weight or less, even more preferably more than 0 parts by weight and 1 part by weight or less. Examples of the surfactant for use and the amount thereof are disclosed in U.S. Pat. No. 7,473,739 and the like.

The water-absorbing resin powder in accordance with an embodiment of the present invention may be surface-crosslinked with the use of an inorganic surface-crosslinking agent, more preferably an ionic bonding surface-crosslinking agent (e.g., polyvalent metal salt), instead of or in addition to the above-described organic surface-crosslinking agent. This improves the liquid permeability and water absorption speed of the water-absorbing resin powder. The inorganic surface-crosslinking agent may be added concurrently with or separately from the organic surface-crosslinking agent. Examples of the ionic bonding surface-crosslinking agent used include salts (organic salts and inorganic salts) and hydroxides of di- or greater valent metals, preferably trivalent or tetravalent metals. Examples of the polyvalent metals include aluminum and zirconium, and examples of polyvalent metal salts include aluminum salts of organic acid and/or inorganic acid, such as aluminum lactate, aluminum sulfate, and aluminum acetate, and aluminum malate. The ionic bonding surface-crosslinking agent is more preferably aluminum sulfate and/or aluminum lactate.

Surface crosslinking using a polyvalent metal salt is disclosed in International Publication Nos. WO 2007/121037, WO 2008/09843, and WO 2008/09842, U.S. Pat. Nos. 7,157,141, 6,605,673, and 6,620,889, and U.S. Patent Application Publication Nos. 2005/0288182, 2005/0070671, 2007/0106013, and 2006/0073969.

The amount of the polyvalent metal salt added is preferably 0.01 weight % to 5.0 weight %, more preferably 0.05 weight % to 1.0 weight %, relative to the water-absorbing resin powder. The polyvalent metal salt added in an amount of 0.01 weight % or more is preferred, because liquid permeability improves. The polyvalent metal salt added in an amount of 5.0 weight % or less is preferred, because fluid retention capacity under pressure does not become too low.

(Solvent and Others)

The amount of the surface-crosslinking agent used is preferably 0.001 parts by weight to 10 parts by weight, more preferably 0.01 parts by weight to 5 parts by weight, relative to 100 parts by weight of the water-absorbing resin powder to be subjected to surface treatment. The surface-crosslinking agent is used preferably in combination with water. The amount of water used is preferably 0.5 parts by weight to 20 parts by weight, more preferably 0.5 parts by weight to 10 parts by weight, relative to 100 parts by weight of the water-absorbing resin powder to be subjected to surface treatment. Also in a case where an inorganic surface-crosslinking agent and an organic surface-crosslinking agent are used in combination, the amount of each of the inorganic and organic surface-crosslinking agents is preferably 0.001 parts by weight to 10 parts by weight, more preferably 0.01 parts by weight to 5 parts by weight, relative to 100 parts by weight of the water-absorbing resin powder subjected to surface treatment.

A hydrophilic organic solvent may also be used here. The amount of the hydrophilic organic solvent used is preferably more than 0 parts by weight and 10 parts by weight or less, more preferably more than 0 parts by weight and 5 parts by weight or less, relative to 100 parts by weight of the water-absorbing resin powder subjected to surface treatment. In addition, when a crosslinking agent solution is mixed into the water-absorbing resin powder that is to be subjected to surface treatment, water-insoluble fine particle powder and/or a surfactant may coexist in an amount that does not impair the effects of an embodiment of the present invention, e.g., in an amount of preferably more than 0 parts by weight and 10 parts by weight or less, more preferably more than 0 parts by weight and 5 parts by weight or less, even more preferably more than 0 parts by weight and 1 part by weight or less. Examples of the surfactant for use and the amount thereof are disclosed in U.S. Pat. No. 7,473,739 and the like.

(Mixing)

When a solution of the surface-crosslinking agent is mixed with the water-absorbing resin powder that is to be subjected to surface treatment, the water-absorbing resin powder that is to be subjected to surface treatment swells with water or the like contained in the surface-crosslinking agent solution. The swollen water-absorbing resin powder is dried with heat. The heating temperature here is preferably 80° C. to 220° C. and the heating time is preferably 10 minutes to 120 minutes.

When the mixing of the surface-crosslinking agent is performed, a vertical or horizontal high-speed stirring mixer is suitably used. The rotation speed of the mixer is preferably 100 rpm to 10000 rpm, more preferably 300 rpm to 2000 rpm. The retention time is preferably 180 seconds or shorter, more preferably 0.1 seconds to 60 seconds, even more preferably 1 second to 30 seconds.

(Ionic Bonding Surface-crosslinking Agent)

In a case where surface crosslinking is performed with the use of an inorganic surface-crosslinking agent, more preferably an ionic bonding surface-crosslinking agent (e.g., a polyvalent metal salt) in the present step, such an inorganic surface-crosslinking agent may be used instead of or in addition to the earlier-mentioned organic surface-crosslinking agent. The inorganic surface-crosslinking agent may be added concurrently with or separately from the organic surface-crosslinking agent.

[3-6] Other Steps (Granulation Step and the Like Steps)

The method of an embodiment of the present invention may optionally include a step of recycling evaporated monomers, a granulation step, a fine powder removal step, and/or the like, in addition to the above-described steps. In any of or all of the above steps, any of the following additives may be used optionally to achieve long-lasting color tone stability, prevent gel deterioration, and the like. Specifically, a water-soluble or water-insoluble polymer, a lubricant, a chelating agent, a deodorant, an antibacterial agent, water, a surfactant, water-insoluble fine particles, an antioxidant, a reducing agent, and/or the like may be added and mixed in an amount of preferably more than 0 weight % and 30 weight % or less, more preferably 0.01 weight % to 10 weight %, relative to the water-absorbing resin. Any of these additives may also be used as a surface treating agent.

Furthermore, according to the intended use, an oxidant, an antioxidant, water, a polyvalent metal compound, water-insoluble inorganic or organic powder such as silica or metallic soap, a deodorant, an antibacterial agent, a high molecular polyamine, pulp, thermoplastic fiber, and/or the like may be added to the water-absorbing resin in an amount of 3 weight % or less, preferably 1 weight % or less.

[4] Method for Evaluating Polyacrylic Acid (Salt)-based Water-absorbing Resin Powder The gel particle's collapse rate at swelling of polyacrylic acid (salt)-based water-absorbing resin powder in accordance with an embodiment of the present invention is determined in the following manner. Specifically, i) water-absorbing resin powder obtained through classification to have a particle size of 150 μm or more and less than 850 μm is allowed to swell in a 0.9 weight % aqueous sodium chloride solution for 1 hour to become swollen gel particles, ii) the swollen gel particles obtained in the i) are wet-classified using sieves and a graph is created which plots: the cumulative percentage of swollen gel particles that have passed through each sieve, which is found from the amount of swollen gel particles remaining on the mesh of each sieve; and the mesh sizes in terms of dry classification calculated from the mesh sizes of the sieves used in the wet classification, and iii) the gel particle's collapse rate at swelling of the water-absorbing resin powder is calculated from the weight percentage (unit: weight %) of particles having a particle size less than 180 μm in terms of dry classification found from the graph created in the ii).

More specifically, a method of evaluating the degree of collapse of swollen gel particles of an embodiment of the present invention may preferably include the following six procedures:

(procedure 1) classifying water-absorbing resin powder having a moisture content of 10 weight % or less with the use of two or more sieves having different mesh sizes;

(procedure 2) allowing all or part of the water-absorbing resin powder to swell with a sweller liquid to become swollen gel particles;

(procedure 3) further classifying the swollen gel particles with the use of two or more sieves having different mesh sizes and finding the cumulative percentage of swollen gel particles that pass through each of the sieves;

(procedure 4) calculating a swelling capacity from the weight or volume of the all or part of the water-absorbing resin powder subjected to the procedure 2 and the weight or volume of the swollen gel particles obtained in the procedure 3;

(procedure 5) on the basis of the swelling capacity, converting the mesh sizes of the sieves used in the procedure 1 into respective mesh sizes of sieves for use in the procedure 3 or converting the mesh sizes of the sieves used in the procedure 3 into respective mesh sizes of sieves for use in the procedure 1;

(procedure 6) finding the rate of collapse of the swollen gel particles from a plot of the mesh sizes of the sieves calculated in the procedure 5 and the cumulative percentage of the swollen gel particles that pass through each of the sieves obtained in the procedure 3.

The following describes, in detail, polyacrylic acid (salt)-based water-absorbing resin powder, which is to be evaluated in an embodiment of the present invention, and each procedure of a method of evaluating the polyacrylic acid (salt)-based water-absorbing resin powder.

[4-1] Polyacrylic Acid (Salt)-based Water-absorbing Resin Powder

A method for evaluating polyacrylic acid (salt)-based water-absorbing resin powder in accordance with an embodiment of the present invention includes performing evaluation using water-absorbing resin powder that satisfies the physical properties described in the earlier-described section [2] and that has a specific moisture content described below. The evaluation method in accordance with an embodiment of the present invention uses such water-absorbing resin powder and therefore is able to cause swelling with a sweller liquid and, as a result, to perform a comparison between the states before and after the swelling.

The water-absorbing resin powder is not particularly limited, provided that the water-absorbing resin powder is so dry that it can swell. It is desirable that the water-absorbing resin powder be pre-adjusted so that the moisture content of the water-absorbing resin powder is preferably 10 weight % or less, more preferably 8 weight % or less, even more preferably 5 weight % or less.

The water-absorbing resin powder, which is to be evaluated by the evaluation method in accordance with an embodiment of the present invention, is a water-absorbing resin in powder form produced through the polymerization step, the gel-crushing step, and the drying step, and, optionally, the pulverizing step, the classification step, the surface-crosslinking step, and/or the like.

In an embodiment of the present invention, if the water-absorbing resin powder thus obtained has a moisture content of 10 weight % or less, then the water-absorbing resin powder may be used "as-is" in the evaluation method of an embodiment of the present invention. On the other hand, in a case where the water-absorbing resin powder has a moisture content more than 10 weight % because the water-absorbing resin powder has absorbed moisture in the air or the like, the water-absorbing resin powder may be dried under reduced pressure at around 60° C. so that the moisture content thereof is pre-adjusted to 10 weight % or less before being used in the evaluation method of an embodiment of the present invention. It is noted that the above-described steps such as the polymerization step, the gel-crushing step, and the drying step may be performed appropriately using a technique normally used in this field.

[4-2] Method for Evaluating Polyacrylic Acid (Salt)-based Water-absorbing Resin Powder (Procedure 1) First Classification Operation The evaluation method in accordance with an embodiment of the present invention includes an operation of classifying, with the use of sieves, water-absorbing resin powder having a specific moisture content (procedure 1: first classification operation). The classification (first classification) is performed on dry water-absorbing resin powder and therefore is preferably dry classification. It is noted that the "classification" in the evaluation method in accordance with an embodiment of the present invention means an operation of separating water-absorbing resin powder or swollen gel particles into different particle diameters, and therefore is different from the "classification" in the classification step of the production process of the water-absorbing resin powder.

In the procedure 1, the classification is performed with the use of two or more sieves having different mesh sizes, and thereby the water-absorbing resin powder can be separated into specific particle diameters or the particle size distribution of the water-absorbing resin powder can be determined.

The sieves for use in the first classification operation are not limited to particular mesh sizes, provided that water-absorbing resin powder having a desired particle size distribution can be obtained with the sieves. Therefore, sieves having any mesh sizes may be used. It is noted that, in a case where the particle size distribution is defined using JIS standard sieves (JIS Z 8801-1(2000)) (hereinafter merely referred to as "sieves"), the mesh sizes of the sieves described here are in conformity with the values of the "nominal mesh sizes" disclosed in JIS standard. Specifically, Appendix 2 of JIS Z 8801-1(2000) provides the "nominal mesh sizes" such as 850 μm, 710 μm, 600 μm, 500 μm, 425 μm, 355 μm, 300 μm, 250 μm, 212 μm, 180 μm, 150 μm, 125 μm, 106 μm, 90 μm, 75 μm, and the like. This specification uses these values unless otherwise specified. It is noted that, although the "nominal mesh sizes" of 1 mm and more described in Appendix 1 of JIS Z 8801-1(2000) are also included, this specification omits the descriptions of such mesh sizes.

The number of sieves for use in the procedure 1 is not particularly limited, provided that two or more sieves having different mesh sizes are used. The number of sieves may be selected appropriately from, for example, about two to ten. The use of more sieves enables a more finely graduated particle size distribution.

In a case where two or more sieves having different mesh sizes are used in the procedure 1, the sieve having the largest mesh size (coarsest sieve) may be selected appropriately from preferably sieves having a mesh size of 600 μm or more, more preferably sieves having a mesh size of 710 μm or more, and even more preferably sieves having a mesh size of 850 μm or more. The sieve having the smallest mesh size (finest sieve) may be selected appropriately from preferably sieves having a mesh size of 300 μm or less, more preferably sieves having a mesh size of 250 μm or less, even more preferably sieves having a mesh size of 212 μm or less, particularly preferably sieves having a mesh size of 180 μm or less, most particularly sieves having a mesh size of 150 μm or less.

It is noted that, in a case where the number of sieves for use in the procedure 1 is two, the two sieves may be any combination of a sieve selected from the above coarsest sieves and a sieve selected from the above finest sieves. For example, the two sieves may be a combination of a sieve having a mesh size of 600 μm and a sieve having a mesh size of 212 μm, a combination of a sieve having a mesh size of 710 μm and a sieve having a mesh size of 180 μm, a combination of a sieve having a mesh size of 850 μm and a sieve having a mesh size of 150 μm, or the like combination.

The following further describes the case where the number of sieves for use in the procedure 1 is two. For example, in a case where a sieve having a mesh size of A μm (such a sieve is referred to as "sieve A") and a sieve having a mesh size B μm (such a sieve is referred to as "sieve B") (assume that the mesh sizes satisfy A<B) are used to perform classification, first, water-absorbing resin powder is classified with the use of sieve B and then water-absorbing resin powder that has passed through sieve B is further classified with the use of sieve A. Water-absorbing resin powder remaining on sieve A as a result is the water-absorbing resin powder having a particle size distribution of A μm or more and less than B μm. Specifically, in a case where a combination of a sieve having a mesh size of 850 μm and a sieve having a mesh size of 150 μm is selected, sieve A corresponds to the sieve having a mesh size of 150 μm whereas sieve B corresponds to the sieve having a mesh size of 850 μm.

The following describes a case in which the number of sieves for use in the procedure 1 is two or more. For example, in a case where a sieve having a mesh size of A μm (such a sieve is referred to as "sieve A"), a sieve having a mesh size B μm (such a sieve is referred to as "sieve B"), a sieve having mesh size of C μm (such a sieve is referred to as "sieve C"), a sieve having a mesh size D μm (such a sieve is referred to as "sieve D"), a sieve having a mesh size of E μm (such a sieve is referred to as "sieve E"), and a sieve having a mesh size F μm (such a sieve is referred to as "sieve F") (assume that the mesh sizes satisfy A<B<C<D<E<F) are used to perform classification, the sieve having the largest mesh size (sieve F in the above example) may be located at the top, subsequent sieves may be arranged so that the mesh size decreases from top to bottom, and the sieve having the smallest mesh size (sieve A in the above example) may be located at the bottom. It is noted that sieve F may be any sieve selected from the earlier-mentioned coarsest sieves, and sieve A may be any sieve selected from the earlier-mentioned finest sieves. Furthermore, the mesh sizes of sieves B to E may be any mesh sizes selected from the earlier-mentioned nominal mesh sizes, provided that the above arrangement of the mesh sizes is satisfied. The sieves B to E may be alternatively selected from the earlier-mentioned coarsest sieves or the finest sieves.

The water-absorbing resin powder remaining on sieve A as a result of the classification is water-absorbing resin powder having a particle size distribution of A μm or more and less than B μm. Similarly, the water-absorbing resin powder remaining on sieve B is water-absorbing resin powder having a particle size distribution of B μm or more and less than C μm, the water-absorbing resin powder remaining on sieve C is water-absorbing resin powder having a particle size distribution of C μm or more and less than D μm, the water-absorbing resin powder remaining on sieve D is water-absorbing resin powder having a particle size distribution of D μm or more and less than E μm, the water-absorbing resin powder remaining on sieve E is water-absorbing resin powder having a particle size distribution of E μm or more and less than F μm, and the water-absorbing resin powder remaining on sieve F is water-absorbing resin powder having a particle size distribution of F μm or more.

The first classification operation of the procedure 1 provides water-absorbing resin powder having a specific particle diameter. It is noted that, in an embodiment of the present invention, the water-absorbing resin powder remaining on the coarsest sieve at the top is referred to as "coarse particles", and the water-absorbing resin powder that passes through the finest sieve at the bottom is referred to as "fine powder".

In an embodiment of the present invention, the water-absorbing resin powder resulting from the removal of the coarse particles and/or fine powder by the first classification operation has a polymerization represented as "a" (unit: g), which is used in calculation of swelling capacity in the following (procedure 4).

It is noted that the coarse particles are not limited to a particular particle diameter, and the particle diameter depends on the mesh size of a sieve used. The coarse particles have a particle diameter of preferably 600 μm or more, more preferably 710 μm or more, even more preferably 850 μm or more. The fine powder is not limited to a particular particle diameter and the particle diameter depends on the mesh size of a sieve used. The fine powder has a particle diameter of preferably less than 300 μm, more preferably less than 250 μm, even more preferably less than 212 μm, particularly preferably less than 180 μm, most preferably less than 150 μm.

For example, in a case where a sieve having a mesh size of 850 μm and a sieve having a mesh size of 150 μm are used to perform classification and thereby the coarse particles and fine powder are removed in the first classification operation, the total weight of particles having a particle diameter of 150 μm or more and less than 850 μm is used as the weight "a" of the water-absorbing resin powder.

It is noted that, instead of sieve classification, some other classifier such as an air sifter may be used.

In the first classification operation of the procedure 1, the amount of the water-absorbing resin powder placed in each sieve per unit area of the sieve may be selected appropriately so that the classification operation can be performed properly, and is preferably 0.01 kg/m² to 40 kg/m², more preferably 0.1 kg/m² to 5 kg/m². As used herein, the term "amount of the water-absorbing resin powder placed" denotes the weight of water-absorbing resin powder placed on each sieve. The above numeric range also applies to wet classification of swollen gel particles in the second classification operation in the procedure 3.

The efficiency of classification is, for example, 70 weight % or more, 80 weight % or more, 90 weight % or more, 91 weight % or more, 92 weight % or more, 93 weight % or more, 94 weight % or more, 95 weight % or more, 96 weight % or more, 97 weight % or more, 98 weight % or more, 99 weight % or more, 100 weight %, and is preferably 90 weight % or more. It is noted that the term "efficiency of classification" denotes, assuming that a certain amount of water-absorbing resin powder is classified and that the weight of particles which can pass through a sieve having a specific mesh size is 100, the weight percentage of particles that can pass through this sieve in a classification operation in the measurement method of an embodiment of the present invention.

The classification step enables separation into predetermined particle sizes, as described above.

(Procedure 2) Swelling Operation

The evaluation method in accordance with an embodiment of the present invention includes a swelling operation of allowing the water-absorbing resin powder obtained in the procedure 1 to swell to become swollen gel particles (procedure 2: swelling operation). The swelling is performed by allowing all or part of the water-absorbing resin powder to swell with a sweller liquid. Specifically, in one aspect, separation into water-absorbing resin powders having specific particle diameters is performed in the first classification operation, and water-absorbing resin powder obtained by the separation is allowed to swell in the procedure 2. In an alternative aspect, the entire water-absorbing resin powder may be subjected to the swelling operation without subjecting to the separation into water-absorbing resin powders having specific particle diameters in the first classification operation.

The swelling in the procedure 2 may be performed by a technique normally used in this field. For example, the swelling is performed by immersing water-absorbing resin powder in a specific sweller liquid and allowing it to stand for a certain period of time without pressure or by immersing water-absorbing resin powder in a specific sweller liquid and applying constant pressure.

The sweller liquid for use in the procedure 2 is not limited to a particular kind, provided that the sweller liquid can be taken up by water-absorbing resin powder and can cause the water-absorbing resin powder to swell. Examples of the sweller liquid include water such as pure water, deionized water, distilled water; aqueous sodium chloride solution; aqueous solutions containing polyvalent metal salts (artificial urine); aqueous solutions containing urea or the like (artificial urine); and aqueous solutions of a combination of any of those listed above. Of these, an aqueous sodium chloride solution is preferably used.

In a case where an aqueous sodium chloride solution is used as the sweller liquid, the concentration of the aqueous sodium chloride solution is not particularly limited, but a 0.9 weight % aqueous sodium chloride solution is preferably used.

The swelling time is not limited, provided that the swelling time is at least 30 minutes or longer, from the view point of comparing particles in unswollen and swollen states to correctly evaluate the degree of collapse of swollen gel particles. The swelling time may be selected appropriately from, for example, 30 minutes or longer, 45 minutes or longer, 60 minutes or longer, 75 minutes or longer, 90 minutes or longer, 2 hours or longer, 4 hours or longer, 8 hours or longer, 12 hours or longer, 16 hours or longer, and 24 hours or longer, depending on the type and the like of sweller liquid.

(Procedure 3) Second Classification Operation

The evaluation method in accordance with an embodiment of the present invention includes an operation of classifying the swollen gel particles obtained in the procedure 2 with the use of sieves (procedure 2: second classification operation). This classification (second classification) is performed on swollen gel particles containing water and therefore is preferably wet classification. It is noted that the classification in the procedure 2 is the same as the first classification operation in the above (Procedure 1), except that the classification in the procedure 2 is wet classification.

The mesh size of a sieve and the number of sieves in the procedure 2 are the same as the procedure 1 and are not particularly limited. From the viewpoint of accurately determining the degree of collapse of swollen gel particles, it is preferable that at least one of the sieves used have a mesh size of 300 μm or less.

The wet classification in an embodiment of the present invention is performed in the following manner. Specifically, first, the swollen gel particles obtained in the procedure 2 are sieved with a sieve having a desired mesh size to classify the swollen gel particles. Next, a sweller liquid remaining on the bottom surface of the sieve is wiped off, and thereafter the total weight of the sieve and swollen gel particles remaining on the sieve is measured. The pre-measured weight of the sieve is subtracted from this total weight to calculate the weight "w" (unit: g) of the swollen gel particles remaining on the sieve. This operation was performed on each of the sieves used in the wet classification, and the sum (total weight) of the weights "w" of swollen gel particles remaining on the sieves was used as the weight "Z" (unit: g) of the swollen gel particles.

In the above operation, the sweller liquid remaining on the bottom surface of the sieve is wiped off before the weight measurement. By doing this, the weight of the sweller liquid not contributing to swelling is excluded from the weight of the swollen gel particles and therefore the weight of the swollen gel particles is calculated more accurately.

The percentage "Y" (%) of swollen gel particles remaining on each of the sieves having respective mesh sizes can be found using the following (Equation 1).

$$Y(\%) = w/Z \times 100 \qquad \text{(Equation 1)}$$

Furthermore, the cumulative percentage of swollen gel particles passing through each sieve is found from the weight of the swollen gel particles remaining on each sieve described above.

(Procedure 4) Calculation of Swelling Capacity

The evaluation method in accordance with an embodiment of the present invention includes an operation of calculating swelling capacity (procedure 4: calculation of swelling capacity). In the procedure 4, swelling capacity is calculated from the weight or volume of the water-absorbing resin powder subjected to the procedure 2 and the weight or volume of the swollen gel particles obtained in the procedure 3.

The calculation of swelling capacity above is performed on the basis of the weight of the water-absorbing resin powder subjected to the procedure 2 and the weight of the swollen gel particles obtained in the procedure 3.

Assuming that the weight of the water-absorbing resin powder subjected to the procedure 2 is "a" and the weight of the swollen gel particles obtained in the procedure 3 is "Z", the swelling capacity "α" for the sweller liquid in this measurement is found using the following (Equation 2).

$$\alpha(g/g) = Z/a \qquad \text{(Equation 2)}$$

It is noted that the weight "Z" of the swollen gel particles is the total weight of the water-absorbing resin powder and the sweller liquid, that is, the sum of the weight of the sweller liquid and the weight (weight "a") of the water-absorbing resin powder (i.e., the weight of the swollen gel particles swollen with the sweller liquid). The weight "Z" of the swollen gel particles may be measured immediately after the water-absorbing resin powder has swollen or may be measured after the water-absorbing resin powder has swollen and then subjected to a classification step (second classification step).

Alternatively, the swelling capacity "α" can be calculated from the volume of the water-absorbing resin powder and the volume of the swollen gel particles.

Specifically, assuming that the volume of the water-absorbing resin powder is "a" and the volume of the swollen gel particles is "Z", the swelling capacity "α" can be calculated using the same equation as above.

(Procedure 5) Conversion of Mesh Sizes

The evaluation method in accordance with an embodiment of the present invention includes an operation of converting mesh sizes (procedure 5: conversion of mesh sizes). Specifically, the procedure 5 is an operation of correction by which, on the basis of the swelling capacity found in the procedure 4, a comparison becomes available between the particle diameter of the unswollen water-absorbing resin powder and the particle diameter of the swollen gel particles. A specific method therefor is not particularly limited.

For example, in the procedure 5, the mesh sizes in the first classification operation (dry classification) can be converted into mesh sizes for the second classification operation (wet classification) on the basis of the swelling capacity found in the procedure 4. Alternatively, in the procedure 5, the mesh sizes in the second classification operation (wet classification) can be converted into mesh sizes for the first classification operation (dry classification) on the basis of the swelling capacity found in the procedure 4.

That is, the conversion of mesh sizes on the basis of either the first classification operation or the second classification operation enables a comparison between the mesh sizes in the first classification operation and the mesh sizes in the second classification operation. That is, the conversion enables a comparison between the particle diameter of the unswollen water-absorbing resin powder and the particle diameter of the swollen gel particles. This makes it possible to perform a comparison of particle size distribution between unswollen and swollen particles.

Assume that mesh sizes in the second classification operation in an embodiment of the present invention are converted into mesh sizes for the first classification operation. For example, the following (Equation 3) can be used to calculate a mesh size "X", which is equivalent to a particle diameter of unswollen particles, from the mesh size "x" of each sieve.

$$X \, (\mu m) = x/\alpha(1/3) \quad \text{(Equation 3)}$$

(Procedure 6) Calculation of Rate of Collapse of Swollen Gel Particles

The evaluation method in accordance with an embodiment of the present invention includes an operation of calculating the rate of collapse of swollen gel particles on the basis of the values obtained in the procedures 1 to 5 (Procedure 6: calculation of rate of collapse of swollen gel particles). The procedure 6 is performed on the basis of the values obtained in the procedures 1 to 5. In this regard, in the procedure 5, the results obtained in the first classification operation and the second classification operation are not limited to a particular kind, provided that the results are indicative of information on particle size distribution.

In the procedure 6, in a case where the result of the first classification operation and the result of the second classification operation are of particle size distribution, the rate of collapse of swollen particles is calculated in the following manner, for example. Specifically, the "X" (mesh size equivalent to a particle diameter of unswollen particles) of each sieve found in the procedure 5 and the percentage (cumulative percentage) of particles passed thorough each sieve which is found from the "Y" (percentage of remaining swollen gel particles) are plotted on a graph. The plot is compared with the result of the pre-measured particle size distribution in the first classification operation. With this comparison, it is possible to calculate the particle size distribution of swollen particles from the particle size distribution of unswollen particles without having to actually allow the water-absorbing resin powder to swell.

It is noted that, if water-absorbing resin powder collapses to a greater extent when swelling to become swollen gel particles, fine gel powder generated during the swelling increases in percentage. Therefore, the procedure may alternatively include evaluating the degree of collapse of swollen gel particles by performing a comparison of percentage of fine powder (fine gel powder) smaller than a certain particle diameter between the first and second classification operations. In this comparison, the particle diameter of the fine gel powder in the second classification operation is converted into a particle diameter of unswollen particles.

The comparison of percentage of the fine gel powder between the first and second classification operations, that is, the comparison of percentage of the fine gel powder between unswollen and swollen particles, is performed in the following manner, for example. Specifically, first, in the same manner as above, the "X" (mesh size equivalent to a particle diameter of unswollen particles) and the percentage (cumulative percentage) of particles passed thorough each sieve which is found from the "Y" (percentage of remaining swollen gel particles) are plotted on a graph. Next, the percentage of fine gel powder smaller than a certain mesh size, which is a mesh size obtained by conversion into that for unswollen particles, is found by finding the percentage of swollen gel particles that pass through the mesh size equivalent to the above certain particle diameter (in regard to the above "X", the equation of a line connecting two points, which correspond to a finer sieve than a specific size and a coarser sieve than the specific size, is used to calculate the percentage of passed swollen gel particles corresponding to the specific size). This is compared with the result of pre-measured particle size distribution in the first classification step.

Assume a case in which water-absorbing resin powder having a specific particle diameter is separated by the first classification operation and the water-absorbing resin powder obtained as a result of the separation is allowed to swell in the swelling operation. In this case, when the smallest value in the particle diameter range of the water-absorbing resin powder obtained as a result of the separation by the first classification operation is used as the earlier-mentioned certain particle diameter that serves as the basis for determination of percentage of fine gel powder, it is possible to find the percentage of fine gel powder which generates as a result of collapse of swollen gel particles at swelling and which is smaller than the smallest value in the particle diameter range of the unswollen water-absorbing resin powder. Therefore, it is possible to quantify the degree of collapse of gel particles when a water-absorbing resin has swollen to become the gel particles.

Since dry classification and wet classification are different in classification efficiency, both use particles of different sizes as the basis for comparison. Generally, wet classification uses a larger particle than dry classification as the basis for comparison.

In an embodiment of the present invention, as described in "[1] Definitions", the percentage of fine gel particles that result when powder swells to become gel particles, measured under specific conditions, is referred to as "gel particle's collapse rate at swelling". The calculation of the gel particle's collapse rate at swelling in the procedure 6 makes it possible to determine, on the basis of this gel particle's collapse rate at swelling, to what extent swollen gel particles collapse when water-absorbing resin powder swells to become the swollen gel particles. Therefore, it is possible to select appropriate water-absorbing resin powder suitable for its purpose by using the gel particle's collapse rate at swelling as an indicator.

For example, in a case where water-absorbing resin powder having a high water absorption speed is desired, water-absorbing resin powder having a gel particle's collapse rate at swelling of more than 10 weight % may be selected. In a case where water-absorbing resin powder having a high liquid permeability is desired, water-absorbing resin powder having a gel particle's collapse rate at swelling of 10 weight % or less may be selected.

One possible aspect of a case in which water-absorbing resin powder having a high water absorption speed is desired is a case in which the water-absorbing resin powder is used as an absorbent body of an absorbent article such as a disposable diaper. In this case, when the water-absorbing resin powder is to absorb liquid such as urine, the water-absorbing resin powder is normally caused to absorb liquid such as urine two or more times. However, the water-absorbing resin powder after the first liquid absorption swells and thereby has a decreased osmotic pressure or the like, and the water absorption speed for the second liquid absorption tends to be lower than the first liquid absorption. In this regard, since the method of an embodiment of the present invention enables evaluation of the degree of collapse of gel particles when powder swells to become the gel particles, the method brings about a highly advantageous effect such that a water-absorbing resin can be designed to reduce the difference in water absorption speed between the first liquid absorption and the second liquid absorption.

Furthermore, one possible aspect of a case in which water-absorbing resin powder having a high liquid permeability is desired is a case in which an absorbent article such as a disposable diameter absorbs liquid such as urine. When an absorbent article such as a disposable diaper absorbs liquid such as urine, the following problem arises. That is, the water-absorbing resin powder swells to become gel particles and these swollen gel particles collapse, and fine swollen gel particles resulting from the collapse are fit into gaps between the swollen gel particles and block liquid pathways. As a result, the fluid retention capacity under pressure and liquid permeability decrease. In this regard, since the method of an embodiment of the present invention enables evaluation of the degree of collapse of gel particles when powder swells to become the gel particles, the method brings about a highly advantageous effect such that a water-absorbing resin can be designed to reduce the collapse of gel particles when the resin swells to become the gel particles.

[5] Applications of Polyacrylic Acid (Salt)-based Water-absorbing Resin Powder

The applications of water-absorbing resin powder in accordance with an embodiment of the present invention are not particularly limited. The water-absorbing resin powder is preferably used in an absorbent article such as a disposable diaper, a sanitary napkin, or an incontinence pad. The water-absorbing resin powder shows its high performance when used in a high-density diaper (a disposable diaper that contains a large amount of water-absorbing resin per one disposable diaper), which has had a problem of odor, color and the like derived from its raw materials, especially when used in an upper layer of the absorbent body of the absorbent article.

The amount (core concentration) of a water-absorbing resin contained in an absorbent body that optionally contains some other absorbent material (pulp fiber or the like), in any of the above absorbent articles, is preferably 30 weight % to 100 weight %, more preferably 40 weight % to 100 weight %, even more preferably 50 weight % to 100 weight %, yet further preferably 60 weight % to 100 weight %, particularly preferably 70 weight % to 100 weight %, most preferably 75 weight % to 95 weight %. For example, in a case where water-absorbing resin powder obtained by the production method in accordance with an embodiment of the present invention is used at any of the concentrations above especially in an upper portion of the absorbent body, a high liquid permeability is achieved and thereby absorbed liquid such as urine is diffused well. This efficiently distributes liquid and the entire absorbent article has improved absorption. Furthermore, it is possible to provide an absorbent article in which an absorbent body thereof maintains whiteness that looks clean.

This specification also describes the following aspects of the invention.

1. Water-absorbing resin powder containing a polyacrylic acid (salt) as a main component, which satisfies the following (1) to (4):

(1) a water absorption time according to a vortex method (Vortex) is 42 seconds or less or a free swell rate (FSR) is 0.28 g/(g·s) or more;

(2) the percentage of water-absorbing resin powder having a particle size of 150 μm or more and less than 850 μm is 90 weight % or more;

(3) a gel particle's collapse rate at swelling is 10 weight % or less;

(4) an internal gas bubble ratio defined by the following equation is 0.1% to 2.5%:

Internal gas bubble ratio (%)=(true density−apparent density)/true density×100.

2. The water-absorbing resin powder according to 1, which is surface-crosslinked with a covalently bonding surface-crosslinking agent and which has a fluid retention capacity under pressure (AAP) of 20 g/g or more.

3. The water-absorbing resin powder according to 1 or 2, which has a saline flow conductivity (SFC) of $10 \times 10^{-7} \cdot cm^3 \cdot s \cdot g^{-1}$ or more.

4. The water-absorbing resin powder according to any of 1 to 3, where the percentage of water-absorbing resin powder having a particle size less than 150 μm is 5 weight % or less.

5. The water-absorbing resin powder according to any of 1 to 4, where some particles of the water-absorbing resin powder include an inorganic compound internally present therein.

6. The water-absorbing resin powder according to any of 1 to 5, further containing a polyvalent metal salt.

7. The water-absorbing resin powder according to 5 or 6, where the inorganic compound is in the form of inorganic particles.

8. A method for producing polyacrylic acid (salt)-based water-absorbing resin powder, including a polymerization step of polymerizing an acrylic acid (salt)-based aqueous monomer solution, a gel-crushing step of crushing a crosslinked hydrogel polymer during or after polymerization, and a drying step performed after the gel-crushing, where an inorganic compound is added in the gel-crushing step to the crosslinked hydrogel polymer having a resin solid content of 10 weight % or more and 80 weight % or less, and after gel-crushing which satisfies at least one of the following (1) to (4) is performed:

(1) gel grinding energy (GGE) is 18 J/g to 60 J/g;

(2) gel grinding energy (2) (GGE(2)) is 9 J/g to 40 J/g;

(3) the weight average molecular weight of a water-soluble component of the crosslinked hydrogel polymer increases by 10000 Da to 500000 Da; and (4) gel-crushing is performed until the resultant particulate crosslinked hydrogel polymer has a weight average particle diameter (D50) of 350 μm to 2000 μm and a particle size distribution with a logarithmic standard deviation (σζ) of 0.2 to 1.0, a particulate crosslinked hydrogel polymer obtained from the gel-crushing step is dried using a dryer at a drying temperature of 150° C. to 250° C. in the drying step.

9. The method according to 8, further including a surface treatment step including surface-treating a water-absorbing resin.

10. The method according to 8 or 9, where, in a case where the dryer is a through-flow belt hot air dryer and the gel-crushing satisfies the condition (4), the particulate crosslinked hydrogel polymer when fed into the through-flow belt hot air dryer has a resin solid content of 10 weight % to 80 weight %, the through-flow belt hot air dryer has a drying temperature of 150° C. to 250° C., and hot air has an air velocity in a perpendicular direction (upward and/or downward direction) of 0.8 m/s to 2.5 m/s.

11. The method according to any of 8 to 10, where the inorganic compound is in the form of inorganic particles.

12. The method according to any of 8 to 11, where the inorganic particles are a mineral, a polyvalent metal salt, a polyvalent metal oxide, a polyvalent metal hydroxide, an oxide complex, a hydrotalcite-like compound, or a combination of two or more of these.

13. The method according to any of 8 to 12, where the inorganic compound is added in the form of an aqueous solution or an aqueous dispersion.

14. The method according to any of 8 to 13, where the crosslinked hydrogel polymer subjected to the gel-crushing has a moisture content of 20 weight % to 90 weight %.

15. The method according to any of 8 to 14, where the crosslinked hydrogel polymer subjected to the gel-crushing has a polymerization rate of 90 mol % to 99.5 mol %.

This specification also describes the following aspects of the invention.

1. A method for producing polyacrylic acid (salt)-based water-absorbing resin powder, including
a polymerization step of polymerizing an acrylic acid (salt)-based aqueous monomer solution to obtain a crosslinked hydrogel polymer, a gel-crushing step of gel-crushing the crosslinked hydrogel polymer obtained in the polymerization step to obtain a particulate crosslinked hydrogel polymer, and
a drying step of drying the particulate crosslinked hydrogel polymer obtained from the gel-crushing step,
the gel-crushing step being performed twice or more,
the method further including a step of adding water-absorbing resin fine particles having a particle diameter less than 150 μm during and/or after the first gel-crushing step,
where a mixture of the crosslinked hydrogel polymer having a resin solid content of 10 weight % to 80 weight % and the water-absorbing resin fine particles, the mixture being obtained by adding the water-absorbing resin fine particles, is at least once subjected to the gel-crushing step that satisfies either of the following (a) and (b):
(a) gel grinding energy (GGE) is 18 J/g to 39 J/g,
(b) gel grinding energy (2) (GGE(2)) is 9 J/g to 30 J/g, and
where the obtained particulate crosslinked hydrogel polymer is dried at a drying temperature of 150° C. to 250° C.

2. The method according to 1, further including a surface-crosslinking step of increasing a crosslink density of a surface layer of the water-absorbing resin powder, the surface-crosslinking step including performing surface crosslinking until the water-absorbing resin powder has a fluid retention capacity under pressure (AAP) of 20 g/g or more.

3. The method according to 1 or 2, further including a surface-crosslinking step of increasing a crosslink density of a surface layer of the water-absorbing resin powder, the surface-crosslinking step including performing surface crosslinking until the water-absorbing resin powder has a saline flow conductivity (SFC) of $10 \times 10^{-7} \cdot cm^3 \cdot s \cdot g^{-1}$ or more.

4. The method according to any of 1 to 3, where the water-absorbing resin fine particles are added in an amount of 10 weight % or more.

5. The method according to any of 1 to 4, where the first gel-crushing step is performed concurrently with the progress of the polymerization step.

6. The method according to any of 1 to 5, where the particulate crosslinked hydrogel polymer subjected to the drying step has a resin solid content of 10 weight % to 80 weight %.

7. The method according to any of 1 to 6, where a dryer used in the drying step is a through-flow belt hot air dryer, and hot air in the dryer flows upward and/or downward perpendicularly to a through-flow belt, the hot air having an air velocity of 0.8 m/s to 2.5 m/s.

8. The method according to 2 to 7, where the water-absorbing resin fine particles are added in the presence of a surface-crosslinking agent.

This specification also describes the following aspects of the invention.

1. A method for evaluating the degree of collapse of swollen gel particles when water-absorbing resin powder has swollen to become the swollen gel particles, including:
(procedure 1) classifying water-absorbing resin powder having a moisture content of 10 weight % or less with the use of two or more sieves having different mesh sizes;
(procedure 2) allowing all or part of the water-absorbing resin powder to swell with a sweller liquid to become swollen gel particles;
(procedure 3) further classifying the swollen gel particles with the use of two or more sieves having different mesh sizes and finding the cumulative percentage of swollen gel particles that pass through each of the two or more sieves;
(procedure 4) calculating swelling capacity from the weight or the volume of the all or part of the water-absorbing resin powder subjected to the procedure 2 and the weight or the volume of the swollen gel particles obtained in the procedure 3;
(procedure 5) on the basis of the swelling capacity, converting the mesh sizes of the two or more sieves used in the procedure 1 into respective mesh sizes of sieves for use in the procedure 3 or converting the mesh sizes of the two or more sieves used in the procedure 3 into respective mesh sizes of sieves for use in the procedure 1; (procedure 6) finding the rate of collapse of the swollen gel particles from a plot of the mesh sizes of the two or more sieves obtained by conversion in the procedure 5 and the cumulative percentage of the swollen gel particles that pass through each of the two or more sieves obtained in the procedure 3.

2. The method according to 1, where the all or part of the water-absorbing resin powder allowed to swell in the procedure 2 contains 90 weight % or more particles having a particle diameter of 150 μm or more and less than 850 μm.

3. The method according to 1 or 2, where the all or part of the water-absorbing resin powder allowed to swell in the procedure 2 is water-absorbing resin powder obtained as a result of separation by classification in the procedure 1.

4. The method according to any of 1 to 3, where the procedure 1 includes removing fine particles having a particle diameter less than 300 μm from the water-absorbing resin powder.

5. The method according to any of 1 to 4, where the sweller liquid used in the procedure 2 is a 0.9 weight % aqueous sodium chloride solution.

6. The method according to any of 1 to 5, where the procedure 2 includes allowing the all or part of the water-absorbing resin powder to swell for 30 minutes or longer.

7. The method according to any of 1 to 6, where at least one of the two or more sieves used for classification in the procedure 3 is a sieve having a mesh size of 300 μm or less.

8. The method according to any of 1 to 7, where, in at least one of the procedures 1 and 3, the amount of the swollen gel particles placed in each of the two or more sieves per unit area is 0.01 kg/m$^2$ to 40 kg/m$^2$.

9. The method according to any of 1 to 8, where the procedure 3 is performed by wet classification.

10. The method according to any of 1 to 9, where at least one of the procedures 1 and 3 has a classification efficiency of 90% or more.

11. The method according to any of 1 to 10, where water in gaps is removed before the weight of the swollen gel particles is measured.

EXAMPLES

The following describes embodiments of the present invention on the basis of Examples, but the Examples should not be construed as limiting the present invention. Furthermore, various physical properties provided in the claims and Examples of the present invention were determined in accordance with the EDANA methods and the following measurement methods under the conditions of room temperature (20° C. to 25° C.) and 50% RH humidity, unless otherwise specifically stated. Moreover, the electrical devices presented in Examples and Comparative Examples used a power source of 200 V or 100 V and 60 Hz. It is noted that the "liter" may be written as "L" and "weight %" may be written as "wt %" for convenience.

(a) Water Absorption Time According to Vortex Method (Vortex)

The water absorption time of water-absorbing resin powder in accordance with an embodiment of the present invention was measured in accordance with a vortex method (such water absorption time is referred to as Vortex) as set forth in the "Testing method for water absorption rate of super absorbent polymers" defined in JIS K7224.

(b) Free Swell Rate (FSR)

The free swell rate (FSR) of water-absorbing resin powder in accordance with an embodiment of the present invention was measured in accordance with the FSR testing method disclosed in International Publication No. WO 2009/016055.

(c) Measurement of Gel Particle's Collapse Rate at Swelling

This measurement is aiming at quantifying fine particles resulting from breakage or the like of swollen particles when water-absorbing resin powder absorbs liquid and swells to become the swollen particles.

Water-absorbing resin powder in an amount of 3 g was classified with JIS standard sieves with mesh sizes of 850 μm and 150 μm (Each JIS standard sieve was 80 mm in diameter and 20 mm in height. A Ro-Tap sieve shaker whose product name is "ES-65 sieve shaker" and which is available from iida-seisakusho Japan Corporation was used to perform sieving operation for 5 minutes.), and particles remaining on the sieve having a mesh size of 850 μm and fine particles that have passed through the sieve having a mesh size of 150 μm were removed. The weight of the remaining water-absorbing resin powder was measured (this weight is referred to as "a"), and thereafter the water-absorbing resin powder was placed into 1 L of a 0.9 weight % aqueous sodium chloride solution, and was allowed to stand for 1 hour. After 1 hour, the aqueous sodium chloride solution containing swollen particles is placed in pre-arranged sieves for wet particle size measurement. (These sieves are test sieves available from Retsch 200 mm in diameter and 50 mm in height, which were stacked together in a manner such that the mesh size decreases from top to bottom in the order of 710 μm, 600 μm, 425 μm, 300 μm, 150 μm, and 75 μm. A pan that has a capacity large enough to prevent overflow of the liquid passed through the sieves was placed at the bottom of the sieves. It is noted that the mesh sizes should be adjusted appropriately depending on the swelling capacity or the like of the water-absorbing resin powder.) The gel particles remaining in the vessel is washed with a 0.9 weight % aqueous sodium chloride solution so that the whole quantity is placed onto the sieves. Next, the following wet classification operation is performed.

Wet classification operation: the aqueous sodium chloride solution which has passed through the sieves is collected in a vessel (at least 600 mL or more), and spread on the uppermost sieve again. This operation is performed ten times. After that, the uppermost sieve is removed, the aqueous sodium chloride solution remaining between gel particles and the solution remaining on the sieve is wiped off thoroughly with a Kimtowel wiper (available from NIPPON PAPER CRECIA Co., LTD.) from the bottom surface of the sieve, and the total weight of the sieve and the gel particles on the sieve is measured. The pre-measured weight of the sieve is subtracted from this weight, whereby the weight of the gel particles remaining on the sieve is obtained.

The above-described wet classification operation is performed for each mesh size sieve from top to bottom, and the weight "w" of gel particles remaining on each mesh size sieve is measured. The total weight of gel particles remaining on all the sieves is calculated (this weight is referred to as "Z" g).

The percentage "Y" (%) of gel particles remaining on each mesh size sieve is found using the following equation.

$$Y (\%) = w/Z \times 100$$

Next, the swelling capacity "a" for the case of a 0.9 weight % aqueous sodium chloride solution in this measurement is found using the following equation.

$$\alpha (g/g) = Z/a$$

Next, for conversion of the sizes of swollen gel particles into particle diameters before swelling, a mesh size "X" equivalent to a particle diameter before swelling is calculated from the mesh size "x" of each sieve, using the following equation.

$$X (\mu m) = x/\alpha (1/3)$$

The thus-obtained "X" for each sieve and the percentage of particles passed through each sieve found from the "Y" of each sieve are plotted on a graph (The cumulative percentage of particles that have passed through each sieve is plotted. That is, the total amount of particles that have passed through that sieve is plotted.), and the percentage of passable particles corresponding to 180 μm on the plot is found (in regard to the above "X", the equation of a line connecting two points, which correspond to a sieve finer than 180 μm and a sieve coarser than 180 μm, is used to calculate the percentage of passable particles corresponding to 180 μm). Although particles having a particle diameter less than 150 μm were removed from the water-absorbing resin powder, the particle diameter "180 μm" is used here instead of "150 μm" because classification efficiency is different between dry classification and wet classification. The percentage of passable particles corresponding to 180 μm thus found was used as a gel particle's collapse rate at swelling (%).

(d) Internal Gas Bubble Ratio

The internal gas bubble ratio of water-absorbing resin powder in accordance with an embodiment of the present invention was measured in the following manner. Specifically, the internal gas bubble ratio of water-absorbing resin powder was calculated from an apparent density (this is represented as "ρ1" (unit: g/cm³)) measured by the method described in the following (Apparent density) and a true density (this is represented as "ρ2" (unit: g/cm³)) measured by the method described in the following (True density) using the following Equation (11).

$$\text{Internal gas bubble ratio [\%]} = (\rho_1 - \rho_2)/\rho_2 \times 100 \quad \text{Equation (11)}$$

(Apparent Density)

After moisture is removed from water-absorbing resin powder, the apparent density of the water-absorbing resin powder, which is found from the volume of a certain weight of the water-absorbing resin powder containing therein voids not communicating to the outside environment (such voids are referred to as closed cells), was measured with the use of a dry density meter.

Specifically, first, 6.0 g of water-absorbing resin powder was weighed in an aluminum cup whose bottom diameter was about 5 cm, and then allowed to stand for 3 hours or longer in a windless dryer at 180° C. until the moisture content of the water-absorbing resin powder reached 1 weight % or less, such that the water-absorbing resin powder was thoroughly dried. The apparent density (unit: g/cm$^3$) of 5.00 g of the dried water-absorbing resin powder was measured with the use of a dry automatic density meter (AccuPycII 1340TC-10CC, available from Shimadzu Corporation/carrier gas: helium). The measurement was repeated until the same value was obtained five or more times in a row.

(True Density)

Closed cells present inside the water-absorbing resin normally have a diameter of 1 μm to 300 μm. In pulverization, the water-absorbing resin starts breaking from portions near the closed cells. In view of this, if the water-absorbing resin powder is pulverized until the particle size reaches a size less than 45 μm, the resultant water-absorbing resin powder contains almost no closed cells. Therefore, the dry density of the water-absorbing resin powder having been pulverized to less than 45 μm was used as a true density for evaluation.

Specifically, 15.0 g of the water-absorbing resin powder and 400 g of columnar porcelain balls (diameter: 13 mm, length: 13 mm) were placed in a ball mill pot (available from TERAOKA, model No. 90, internal dimensions: 80 mm in diameter and 75 mm in height, external dimensions: 90 mm in diameter and 110 mm in height), and then the ball mill pot was operated at 60 Hz for 2 hours, such that a water-absorbing resin which pass through a JIS standard sieve having a mesh size of 45 μm (a water-absorbing resin having a particle size less than 45 μm) was obtained. Then, 6.0 g of that water-absorbing resin powder having a particle size less than 45 μm was dried at 180° C. for 3 hours or more as with the section "(d) Apparent density" described earlier, and thereafter the dry density was measured. The measured value thus obtained was used as the "true density" of an embodiment of the present invention.

(e) Fluid Retention Capacity under Pressure (AAP)

The fluid retention capacity under pressure (AAP) of water-absorbing resin powder in accordance with an embodiment of the present invention was measured in accordance with ERT442.2-02. It is noted that, in an embodiment of the present invention, the measurement was performed under the conditions in which the load was changed from 2.06 kPa (0.3 psi, 21 g/cm$^2$) to 4.83 kPa (0.7 psi, 49 g/cm$^2$).

(f) Saline Flow Conductivity (SFC)

The saline flow conductivity (SFC) of water-absorbing resin powder in accordance with an embodiment of the present invention was measured in accordance with the SFC test method disclosed in U.S. Pat. No. 5,669,894.

(g) Centrifuge Retention Capacity (CRC) and Gel CRC

The centrifuge retention capacity (CRC) of water-absorbing resin powder in accordance with an embodiment of the present invention was measured in accordance with ERT441.2-02. Specifically, 0.200 g of water-absorbing resin powder was weighed and uniformly placed in an nonwoven fabric bag (size: 60 mm×60 mm) and the bag was heat-sealed. Then, the bag was immersed in 1000 mL of a 0.9 weight % aqueous sodium chloride solution adjusted to a temperature of 25° C.±3° C. After 30 minutes, the bag was removed from the solution and drained with the use of a centrifugal separator (centrifuge available from KOKUSAN Co., Ltd., type H-122) at 250 G for 3 minutes.

After that, the weight "W1" (g) of the bag was measured. A bag containing no water-absorbing resin powder was subjected to the same operation, and the weight "W2" (g) of the bag after the operation was measured. The CRC was calculated using the following Equation (4):

$$\text{CRC[g/g]} = \{(W1-W2)/(\text{weight of water-absorbing resin})\} - 1 \quad \text{Equation (4)}$$

Furthermore, the CRC of a crosslinked hydrogel polymer (such a CRC is hereinafter referred to as "gel CRC") was measured in the following manner. Specifically, the gel CRC was measured by performing the same operation as above, except that 0.4 g of a crosslinked hydrogel polymer was used as a sample and the immersion time was changed from 30 minutes to 24 hours. Furthermore, the measurement of the resin solid content of the crosslinked hydrogel polymer was performed separately, the weight of the water-absorbing resin in 0.4 g of the crosslinked hydrogel polymer was determined, and the gel CRC was calculated using the following Equation (5). It is noted that the measurement was performed five times on each sample and the mean of the five values was used.

$$\text{Gel CRC[g/g]} = \{(mwi-mb)-msi\times(Wn/100)\}/\{msi\times(Wn/100)\} \quad \text{Equation (5)}$$

where $msi$ is the weight (g) of the crosslinked hydrogel polymer before the measurement;

$mb$ is the weight (g) of Blank (nonwoven fabric alone) freely swollen and drained;

$mwi$ is the weight (g) of the crosslinked hydrogel polymer freely swollen and drained; and $Wn$ is the solid content (weight %) of the crosslinked hydrogel polymer.

(h) Moisture Content/Resin Solid Content

The moisture content of water-absorbing resin powder in accordance with an embodiment of the present invention was measured in accordance with ERT430.2-02. Furthermore, the moisture content (unit: weight %) of a crosslinked hydrogel polymer was calculated from a drying loss measured in accordance with ERT430.2-02, except that the sample was changed to 2 g, drying temperature was changed to 180° C., and drying time was changed to 16 hours. It is noted that the measurement was performed five times on each sample and the mean of the five values was used.

Furthermore, the value calculated from the thus-obtained moisture content through "100−moisture content (unit: weight %)" was used as the resin solid content of the water-absorbing resin powder or the crosslinked hydrogel polymer. It is noted that the resin solid content of the crosslinked hydrogel polymer that has not been subjected to gel-crushing was determined using a sample obtained by cutting the crosslinked hydrogel polymer that has not been subjected to gel-crushing into pieces 3 mm or less on a side with the use of scissors, a cutter, or the like.

(i) Ext and Gel Ext

The water-soluble content (Ext) of water-absorbing resin powder in accordance with an embodiment of the present invention was measured in accordance with ERT470.2-02. Specifically, 1.000 g of a water-absorbing resin and 200 mL of a 0.90 weight % aqueous sodium chloride solution were placed in a 250 mL plastic container with a lid, and stirred with a cylindrical stirrer 3.5 cm in length and 6 mm in diameter at 500 rpm for 16 hours, such that a water-soluble component of the water-absorbing resin was extracted. The extract was filtered with the use of a sheet of filter paper (Advantec Toyo Kaisha, Ltd., Product name: JIS P 3801, No. 2, thickness 0.26 mm, retains particle size of 5 μm), and 50.0 g of the obtained filtrate was used as a liquid for measurement.

Next, the liquid for measurement was titrated with a 0.1N—NaOH aqueous solution until the liquid had a pH of 10, and then titrated with a 0.1N—HCl aqueous solution until the liquid had a pH of 2.7. The amounts of the aqueous solutions ([NaOH] mL, [HCl] mL) used in the titration operations were determined. Furthermore, the same operation was performed on a 0.90 weight % aqueous sodium chloride solution alone, and the amounts of the aqueous solutions ([bNaOH] mL, [bHCl] mL) used in the blank titration operations were determined. In the case of a water-absorbing resin of an embodiment of the present invention, the water-soluble content (Ext) was calculated from the average molecular weight of the monomers of the water-absorbing resin and the amounts of the aqueous solutions determined in the above operations, using the following Equation (6).

$$\text{Ext[weight \%]} = 0.1 \times (\text{average molecular weight of monomers}) \times 200 \times 100 \times ([\text{HCl}] - [\text{bHCl}])/1000/1.000/50.0 \qquad \text{Equation (6)}$$

On the other hand, gel Ext was measured by the same operation as described above, except that 5.0 g of a hydrogel cut into pieces about 1 mm to 5 mm on a side with scissors was used and the stirring time was 24 hours. Furthermore, the resin solid content of the hydrogel was measured separately, the weight of the water-absorbing resin in 5.0 g of the hydrogel was determined, and the gel Ext was calculated using the following Equation (7).

$$\text{Gel Ext[weight \%]} = \{(V_{HCl.s} - V_{HCl.b}) \times C_{HCl} \times Mw \times F_{dil} \times 100\}/\{ms \times (Wn/100) \times 1000\} \qquad \text{Equation (7)}$$

where

VHCl.s is the amount (mL) of HCl necessary to change the pH of a filtrate containing a dissolved polymer from 10 to 2.7;

VHCl.b is the amount (mL) of HCl necessary to change the pH of Blank (0.9 weight % aqueous sodium chloride solution) from 10 to 2.7;

CHCl is the concentration (mol/L) of the HCl solution;

Mw is the average molecular weight (g/mol) of monomer units in an acrylic acid (salt) polymer;

(e.g., Mw is 88.1 g/mol in a case where the neutralization rate is 73 mol %);

Fdil is the rate of dilution of the filtrate containing a dissolved polymer;

ms is the weight (g) of the crosslinked hydrogel polymer before the operation; and Wn is the solid content (weight %) of the crosslinked hydrogel polymer.

(j) Weight Average Molecular Weight of Water-Soluble Component

The weight average molecular weight of a water-soluble component is a value obtained by measuring, by GPC, the weight average molecular weight of the polymer dissolved in the aforementioned operations for measuring Ext and gel Ext. The following describes the GPC measurement.

The GPC was performed with the use of TDA302 (Registered Trademark) available from VISCOTECH CO., LTD. This instrument is constituted by a size exclusion chromatograph, a refractive index detector, a light diffusion detector, and a capillary viscometer. The measurement instrument and the measurement conditions were as described below.

Pump/autosampler: GPCmax available from VISCOTECH CO., LTD.

Guard column: SHODEX GF-7B

Column: two TOSOH GMPWXL columns connected in series were used

Detector: TDA302 available from VISCOTECH CO., LTD. (temperature in the system was maintained at 30° C.)

Solvent: aqueous solution of 60 mM sodium dihydrogen phosphate dihydrate and 20 mM disodium hydrogen phosphate dodecahydrate Flow rate: 0.5 mL/min Feeding amount: 100 μL The instrument was calibrated by using polyoxyethylene glycol (weight average molecular weight (Mw) 22396, differential refractive index (dn/dc)=0.132, solvent refractive index 1.33) as a standard sample.

In a case where the to-be-measured substance was a water-absorbing resin obtained by polymerizing monomer containing 99 mol % or more acrylic acid (salt), the measurement was performed on the assumption that the differential refractive index (dn/dc) of the polymer to be analyzed was 0.12. In a case where the to-be-measured substance was a copolymerized water-absorbing resin which contains a monomer other than acrylic acid (salt) in an amount of 1 mol % or more, the measurement was performed by measuring the value of the differential refractive index (dn/dc) inherent to that polymer in a solvent and using the obtained value. Furthermore, data of the refractive index, light scattering intensity, and viscosity were collected and analyzed with the use of Viscotek OmniSEC 3.1 (Registered Trademark) software. The weight average molecular weight (Mw) was calculated based on the data obtained from the refractive index and the light scattering intensity.

(k) PSD

The PSD of water-absorbing resin powder in accordance with an embodiment of the present invention was measured in accordance with ERT420.2-02. It is noted that the weight average particle diameter (D50) of the water-absorbing resin powder and the logarithmic standard deviation (σζ) of the particle size distribution of the water-absorbing resin powder were measured in accordance with the measurement method described in European Patent No. 0349240. On the other hand, the weight average particle diameter (D50) of a crosslinked hydrogel polymer and the logarithmic standard deviation (σζ) of the particle size distribution of the crosslinked hydrogel polymer were measured in the following manner.

Specifically, the following pretreatment was performed: 20 g of a crosslinked hydrogel polymer (solid content: "α" wt %) having a temperature of 20° C. to 25° C. was added to 500 g of a 20 weight % aqueous sodium chloride solution containing 0.08 weight % EMAL 20C (surfactant, available from Kao Corporation) (this aqueous solution is hereinafter referred to as "EMAL aqueous solution") to obtain a dispersion liquid; and the dispersion liquid was stirred with a stirrer chip 50 mm in length and 7 mm in diameter at 300 rpm for 60 minutes (a cylindrical polypropylene container having a capacity of about 1.14 L, a height of 21 cm, and a diameter of 8 cm was used).

After the stirring, the dispersion liquid was placed on a central portion of one of JIS standard sieves provided on a rotary table (diameter: 21 cm, mesh sizes of sieves: 8 mm/4 mm/2 mm/1 mm/0.60 mm/0.30 mm/0.15 mm/0.075 mm). The entire crosslinked hydrogel polymer was washed out onto the sieve by use of 100 g of the EMAL aqueous solution. Then, the crosslinked hydrogel polymer was classified by uniformly spraying 6000 g of the EMAL aqueous solution onto the sieve with the use of a shower (with 72 holes, flow rate: 6.0 L/min) from 30 cm above the sieve in a manner such that the spraying area (50 cm2) entirely covered the sieve while rotating the sieve with a hand (at 20 rpm). The crosslinked hydrogel polymer remaining on the top sieve, which was obtained as a result of the classification, was drained for about 2 minutes, and then the weight thereof was measured. The crosslinked hydrogel polymers on the second and subsequent sieves from top were classified by the same operation and drained, and the weight of the crosslinked hydrogel polymer remaining on each of the sieves was measured.

The weight percentage "weight %" of the crosslinked hydrogel polymer was calculated from the weight of the crosslinked hydrogel polymer remaining on each of the sieves, using Equation (8) below. The mesh sizes of the sieves after the draining were calculated using Equation (9) below, and the particle size distribution of the crosslinked hydrogel polymer was plotted on logarithmic probability paper. The particle size at which the cumulative percentage "% R" of particles on sieve on the plot corresponds to 50 weight % was used as the weight average particle diameter (D50) of the crosslinked hydrogel polymer.

Furthermore, the particle diameter at which the cumulative percentage "% R" of particles on sieve is 84.1% (referred to as "X1") and the particle diameter at which the cumulative percentage "% R" of particles on sieve is 15.9% (referred to as "X2") were found from the above plot, and a logarithmic standard deviation ($\sigma\zeta$) was found using Equation (10) below. A $\sigma\zeta$ having a smaller value means a narrower particle size distribution.

$$X[\%] = (w/W) \times 100 \qquad \text{Equation (8)}$$

$$R(\alpha)[mm] = (20/w)^{1/3} \times r \qquad \text{Equation (9)}$$

where

X is the weight % (%) of the crosslinked hydrogel polymer remaining on each of the sieves after classified and drained;

w is the weight (g) of the crosslinked hydrogel polymer remaining on each of the sieves after classified and drained;

W is the total weight (g) of the crosslinked hydrogel polymers remaining on the sieves after classified and drained;

$R(\alpha)$ is the mesh size (mm) of a sieve in terms of a crosslinked hydrogel polymer having a solid content of "a" weight %; and r is the mesh size (mm) of a sieve with which a crosslinked hydrogel polymer having swollen in a 20 weight % aqueous sodium chloride solution is classified.

$$\sigma\zeta = 0.5 \times \ln(X2/X1) \qquad \text{Equation (10)}$$

where X1 is the particle size when R=84.1% and X2 is the particle size when R=15.9%.

(l) Polymerization Rate of Crosslinked Hydrogel Polymer that has not been Subjected to Gel-Crushing The polymerization rate of a crosslinked hydrogel polymer that has not been subjected to gel-crushing is calculated from polymer content (mol) calculated from pH titration of the crosslinked hydrogel polymer and residual monomer content (mol).

Specifically, in regard to the polymer content (mol) calculated from pH titration, the same method as described in the above section "Ext (ERT470.2-02)" is applied to a hydrogel to calculate the number of moles of monomer units per unit gel weight. Next, in regard to the residual monomer content, the residual monomer content is measured by the same method as described in the above section "Residual Monomers" (ERT410.2-02) and this residual monomer content is converted into the number of moles of monomers. The number of moles of the residual monomers is divided by the number of moles of the monomer units to give a rate of unreacted monomers, and this rate is subtracted from 1 to give a polymerization rate. Since the polymerization rate is represented as a value of 0 to 1, the value is multiplied by 100 and represented in mol %.

(m) Test for Shape Retention Capacity of Gel Particles

The shape retention capacity of gel particles, which are a gelled version of water-absorbing resin powder of an embodiment of the present invention, was measured by the following method with the use of a measurement instrument 200 illustrated in FIG. 1. The following describes the test method with the reference numerals shown in FIGS. 1 and 2.

First, 12 g of water-absorbing resin powder 32 was uniformly spread in the middle of an acrylic resin tray 30 having internal dimensions of 401 mm length×151 mm width×30 mm height and external dimensions of 411 mm length×161 mm width×35 mm height. It is noted that the water-absorbing resin powder 32 was spread within a region referred to as a spread region 31, which had an area of 200 mm length×151 mm width (a region 100.5 mm inside from each inner wall along the length of the tray). The weight of the water-absorbing resin powder was 397 g/m². Before the water-absorbing resin powder 32 was spread, the tray 30 was subjected to some treatment to prevent occurrence of static electricity, such as application of an antistatic agent on the tray 30 or breath blown on the tray 30.

Next, after the water-absorbing resin powder 32 was spread, a top sheet 33 was placed on the water-absorbing resin 32 (FIG. 1). The top sheet 33 used here was a sheet that was removed from a disposable diaper available from Unicharm Corporation (Product Name: MamyPoko Tape, size L/purchased in Japan in June 2014, Number on the bottom of the package: 404088043).

The top sheet 33 had a size of 39 cm length×14 cm width and a weight of 3.3 g to 3.6 g. Since constituents of the disposable diaper such as pulp were attached to the top sheet 33 with adhesive, the constituents were thoroughly removed before use in this measurement. The top sheet 33 was equally spaced from the widthwise inner walls and equally spaced from the lengthwise inner walls.

Next, a wire gauze 34 was placed on the top sheet 33, and a top cover 36 made of acrylic resin was further placed on the wire gauze 34. The wire gauze 34 was a JIS wire gauze made of stainless steel and had a mesh size of 1.21 mm (14-mesh), a wire diameter of 0.6 mm, and a size of 398 mm length×148 mm width. The top cover 36 had a size of 400 mm length×150 mm width×20 mm thickness and had at its central portion a cylindrical inlet 70 mm in internal diameter and 70 mm in height.

Figure 2:
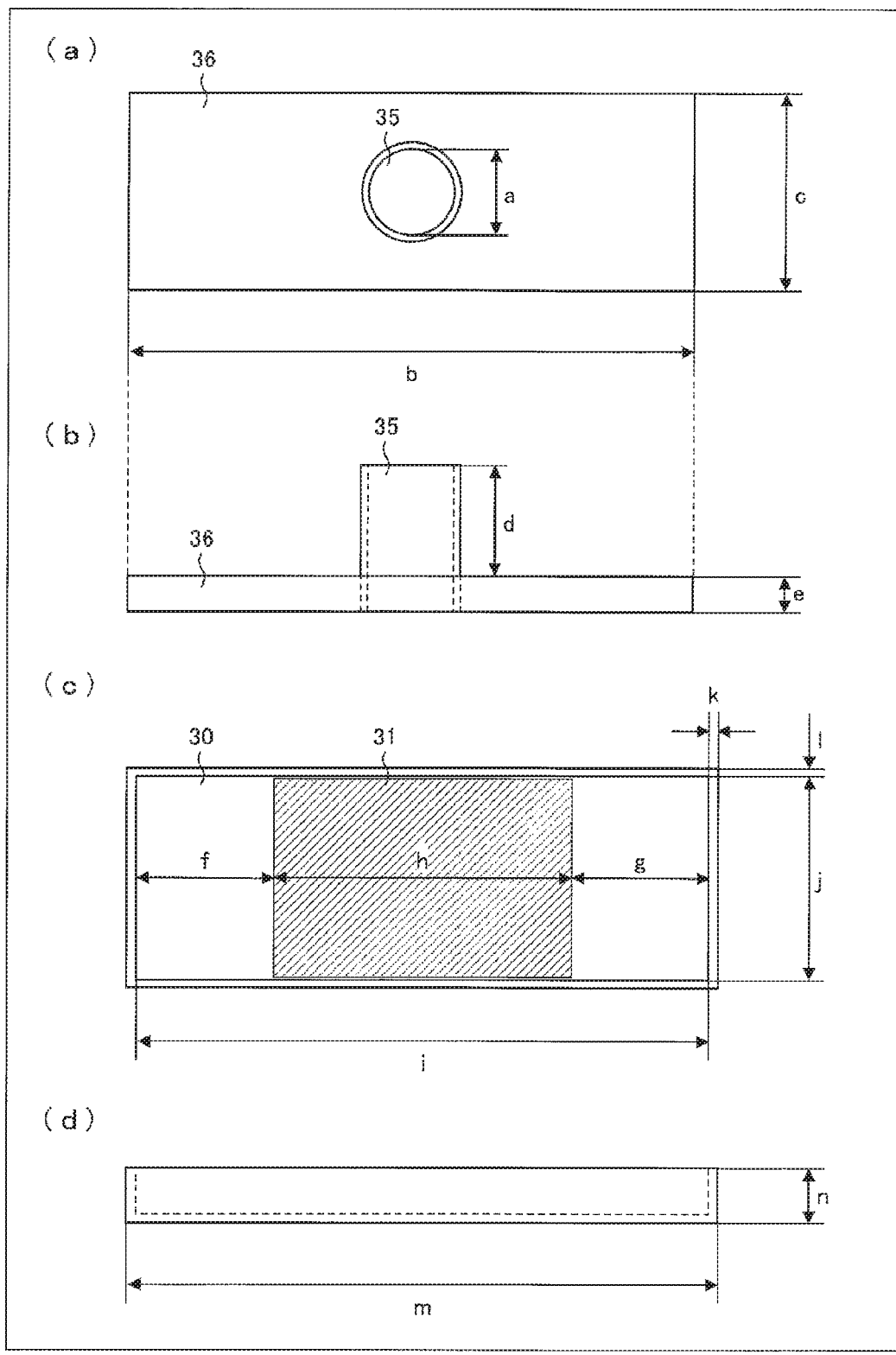
FIG. 2 illustrates the appearance of the measurement instrument for use in measuring the shape retention capacity of gel particles. (a) of FIG. 2 is a top view of a top cover, (b) of FIG. 2 is a side view of the top cover, (c) of FIG. 2 is a top view of a tray, and (d) of FIG. 2 is a side view of the tray.

Next, the top cover 36 illustrated in (a) and (b) of FIG. 2 was placed, and then weights 37 were placed on the top cover 36 as illustrated in FIG. 1. The weights 37 were made of stainless steel and placed in a manner such that a uniform load was applied on the water-absorbing resin powder 32. It is noted that the load was 9.45 g per square centimeter of the wire gauze and 18.8 g per square centimeter of the water-absorbing resin powder. That is, the weights 37 were adjusted so that the total weight of the wire gauze 34, the top cover 36, and the weights 37 was 5672 g.

Next, 100 g of a 0.9 weight % aqueous sodium chloride solution was fed through the cylindrical inlet 35 on the top cover 36 over five seconds. The aqueous sodium chloride solution passed through the wire gauze 34 while spreading over the wire gauze 34 and was absorbed by the water-absorbing resin powder 32.

The aqueous sodium chloride solution was fed three times in each test. In regard to the timing of feeding, the second feeding was performed 10 minutes after the start of the first feeding, and the third feeding was performed 10 minutes after the start of the second feeding.

Figure 3:
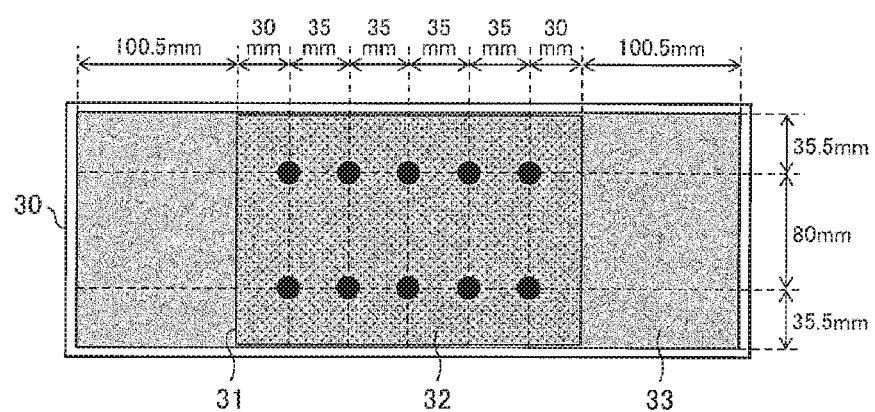
FIG. 3 shows the measurement instrument for use in measuring the shape retention capacity of gel particles viewed from above.

Ten minutes after the start of the third feeding, the weights 37, the top cover 36, and the wire gauze 34 were removed, and the gel layer was pressed perpendicularly against the bottom of the tray through the top sheet 33 with the ball of an index finger over three seconds until the finger felt the bottom of the tray 30. The texture of the gel particles at that time was evaluated on a three-level scale: Excellent; Good; and Poor. It is noted that the gel layer was pressed at the positions indicated by the filled circles (ten positions) illustrated in FIG. 3. The three-point-scale evaluation was conducted on each of these positions, and the most frequent evaluation was used as the shape retention capacity of the gel particles of that sample.

The evaluation scale for the texture of gel particles is as follows.

Excellent: Great resilience of particles having a particle diameter of about 2 mm is felt through the sheet.

Good: Resilience of particles having a particle diameter of about 2 mm is weak and collapse of particles is felt when pressing.

Poor: Particles having a particle diameter of about 2 mm are not felt.

Production Example 1

A crosslinked hydrogel polymer (a) was produced in accordance with Production Example 1 of International Publication No. WO 2011/126079.

As an apparatus for producing polyacrylic acid (salt)-based water-absorbing resin powder, a continuous production apparatus was prepared which includes a polymerization step, a gel-crushing step, a drying step, a pulverization step, a classification step, a surface-crosslinking step, a cooling step, a sizing step, and transportation steps for joining the above steps. It is noted that each of these steps is operated continuously. The continuous production apparatus has a production capacity of about 3500 kg/hr. The above steps can each include a single line or two or more lines. In a case where the above steps each include two or more lines, the production capacity is represented as the sum of the production capacities of the two or more lines. With the use of the continuous production apparatus, polyacrylic acid (salt)-based water-absorbing resin powder was produced continuously.

First, an aqueous monomer solution (a) containing 193.3 parts by weight of acrylic acid, 64.4 parts by weight of a 48 weight % aqueous sodium hydroxide solution, 1.26 parts by weight of polyethylene glycol diacrylate (average number of units: 9), 52 parts by weight of a 0.1 weight % aqueous pentasodium ethylenediamine tetra(methylene phosphonate) solution, and 134 parts by weight of deionized water was prepared.

Next, the aqueous monomer solution (a), which was adjusted to a temperature of 40° C., was continuously fed by use of a metering pump, while 97.1 parts by weight of a 48 weight % aqueous sodium hydroxide solution was line-mixed with the aqueous monomer solution (a) to give a mixture (a). It is noted that, in this operation, the temperature of the mixture (a) rose to 85° C. due to heat of neutralization.

Next, 8.05 parts by weight of a 4 weight % aqueous sodium persulfate solution was continuously line-mixed into the mixture (a), and then the resultant mixture was continuously fed to a continuous polymerization apparatus having a flat polymerization belt with a dam at each side in a manner such that the layer of the mixture had a thickness of about 7.5 mm. After that, polymerization (polymerization time: 3 minutes) was performed continuously, such that a crosslinked hydrogel polymer (a) in the shape of a belt was obtained. The belt-shaped crosslinked hydrogel polymer (a) had a gel CRC of 28.1 g/g, a resin solid content of 52.1 weight %, a water-soluble component in an amount of 3.1 weight %, the water-soluble component having a weight average molecular weight of $21.8 \times 10^4$ Da, and a polymerization rate of 99.5 mol %.

Next, the belt-shaped crosslinked hydrogel polymer (a) was continuously cut, in the width direction relative to the traveling direction of the polymerization belt, into equal lengths of about 300 mm. In this way, a cut crosslinked hydrogel polymer (hereinafter referred to as "cut hydrogel") (a) was obtained.

Comparative Example 1

The cut hydrogel (a) obtained in Production Example 1 above was fed into a gel-crusher (apparatus having a combination of Screw No. S86-445 and Barrel No. B88-478 disclosed in International Publication No. WO 2015/030129) which had, at an end thereof, a porous plate having a diameter of 100 mm, a thickness of 10 mm, and 54 pores in 8 mm diameter, and gel-crushing was performed.

The gel-crushing was performed under the conditions in which the speed of a screw was 96 rpm and the feed rate of the cut hydrogel (a) was 97 g/second. At the same time, hot water of 90° C. was fed into the gel-crusher at 1.08 g/second. The gel-crushing gave a comparative particulate hydrogel (1). It is noted that, in Comparative Example 1, gel grinding energy (GGE) was 10.9 J/g and gel grinding energy (2) (GGE(2)) was 9.9 J/g. Furthermore, the comparative particulate hydrogel (1) had a gel CRC of 28.5 g/g, a resin solid content of 50.9 weight %, a water-soluble component in an amount of 3.7 weight %, the water-soluble component having a weight average molecular weight of $23.5 \times 10^4$ Da, a weight average particle diameter (D50) of 725 μm, and a particle size distribution with a logarithmic standard deviation (σζ) of 0.93.

Next, the comparative particulate hydrogel (1) was spread over a through-flow plate of a hot air dryer within 1 minute from the end of the gel-crushing. The temperature of the comparative particulate hydrogel (1) in this operation was 80° C. After that, the comparative particulate hydrogel (1) was dried by passing hot air of 185° C. through the plate for 30 minutes, such that a comparative dried polymer (1) was obtained. The average air velocity of the hot air was 1.0 m/s in a direction perpendicular to the through-flow plate. The air velocity of the hot air was measured with the use of a constant-temperature thermal anemometer Anemomaster 6162 (available from Kanomax Japan Inc.).

Next, the entire comparative dried polymer (1) of about 60° C. was pulverized (pulverization step) with the use of a roll mill, and then classified (classification step) with the use of JIS standard sieves (JIS Z 8801-1(2000)) having mesh sizes of 710 μm and 175 μm to obtain comparative water-absorbing resin powder (B1). The comparative water-absorbing resin powder (B1) had a weight average particle diameter (D50) of 360 μm, a particle size distribution with a logarithmic standard deviation (σζ) of 0.32, a CRC of 32.8 g/g, a water-soluble component in an amount of 7.8 weight %, and 150 μm passable particles (percentage of water-absorbing resin powder passable through a sieve having a mesh size of 150 μm) in an amount of 1.2 weight %.

Next, 3.9 parts by weight of a covalently bonding surface-crosslinking agent solution composed of 0.3 parts by weight of ethylene carbonate, 0.6 parts by weight of propylene glycol, and 3.0 parts by weight of deionized water was added to 100 parts by weight of the comparative water-absorbing resin powder (B1) and mixed until uniformity was obtained, such that a comparative humidified substance (1) was obtained. After that, the humidified substance (1) was treated with heat at 208° C. for about 40 minutes so that the resultant water-absorbing resin powder (P1) would have a CRC of 26.6 g/g to 27.4 g/g. In this way, the comparative water-absorbing resin powder (P1) was obtained.

After that, the comparative water-absorbing resin powder (P1) was cooled, and an ionic bonding surface-crosslinking agent solution composed of 1.17 parts by weight of a 27.5 weight % aqueous aluminum sulfate solution (8 weight % in aluminum oxide equivalent), 0.196 parts by weight of a 60 weight % aqueous sodium lactate solution, and 0.029 parts by weight of propylene glycol was added to the comparative water-absorbing resin powder (P1) and mixed until uniformity was obtained. In this way, a comparative product (1) was obtained.

After that, the comparative product (1) was crushed (sizing step) until the comparative product (1) became able to pass through a JIS standard sieve having a mesh size of 710 μm. In this way, comparative water-absorbing resin powder (1) was obtained. Physical properties of the comparative water-absorbing resin powder (1) are shown in Tables 1 and 2.

Example 1

The same operation as described in Comparative Example 1 was performed, except that a silica dispersion was used in place of the hot water (90° C.) added during the gel-crushing in Comparative Example 1 and the amount of the dispersion added was 1.23 g/second. It is noted that the silica dispersion was a solution obtained by dispersing 11.84 weight % of Reolosil QS-20 (amorphous silica; available from Tokuyama Corporation) in deionized water and had a temperature adjusted to 90° C. Furthermore, in regard to the amount (1.23 g/second) of the dispersion added, the silica solid content relative to the amount of a hydrogel was 0.15 weight % and the silica solid content relative to the solid content of the hydrogel was 0.29 weight %.

It is noted that, in Example 1, gel grinding energy (GGE) was 12.0 J/g and gel grinding energy (2) (GGE (2)) was 10.9 J/g. Furthermore, a particulate hydrogel (1) had a gel CRC of 28.4 g/g, a resin solid content of 51.1 weight %, a water-soluble component in an amount of 3.6 weight %, the water-soluble component having a weight average molecular weight of $23.6 \times 10^4$ Da, a weight average particle diameter (D50) of 720 μm, and a particle size distribution with a logarithmic standard deviation (σζ) of 0.91.

Furthermore, water-absorbing resin powder (B1) obtained in Example 1 had a weight average particle diameter (D50) of 362 μm, a particle size distribution with a logarithmic standard deviation (σζ) of 0.32, a CRC of 32.7 g/g, a water-soluble component in an amount of 7.7 weight %, and 150 μm passable particles (percentage of water-absorbing resin powder passable through a sieve having a mesh size of 150 μm) in an amount of 1.1 weight %.

Physical properties of the final water-absorbing resin powder (1) are shown in Tables 1 and 2.

Example 2

The same operation as described in Comparative Example 1 was performed, except that a hydrotalcite dispersion was used in place of the hot water (90° C.) added during the gel-crushing in Comparative Example 1 and the amount of the dispersion added was 1.23 g/second. It is noted that the hydrotalcite dispersion was a solution obtained by dispersing 11.84 weight % of hydrotalcite (product name: DHT-6, available from Kyowa Chemical Industry Co., Ltd., $Mg_6Al_2(OH)_{16}CO_3 \cdot 4H_2O$ [x=0.25 and m=0.50 in General Formula (1)], volume average particle diameter 0.5 μm) in deionized water and had a temperature adjusted to 90° C. Furthermore, in regard to the amount (1.23 g/second) of the dispersion added, the hydrotalcite solid content relative to the amount of a hydrogel was 0.15 weight % and the hydrotalcite solid content relative to the solid content of the hydrogel was 0.29 weight %.

It is noted that, in Example 2, gel grinding energy (GGE) was 11.8 J/g and gel grinding energy (2) (GGE (2)) was 10.7 J/g. Furthermore, a particulate hydrogel (2) had a gel CRC of 28.4 g/g, a resin solid content of 51.0 weight %, a water-soluble component in an amount of 3.6 weight %, the water-soluble component having a weight average molecular weight of $23.6 \times 10^4$ Da, a weight average particle diameter (D50) of 715 μm, and a particle size distribution with a logarithmic standard deviation (σζ) of 0.91.

Furthermore, water-absorbing resin powder (B2) obtained in Example 2 had a weight average particle diameter (D50) of 361 μm, a particle size distribution with a logarithmic standard deviation (σζ) of 0.32, a CRC of 32.7 g/g, a water-soluble component in an amount of 7.7 weight %, and 150 μm passable particles (percentage of water-absorbing resin powder passable through a sieve having a mesh size of 150 μm) in an amount of 1.1 weight %.

Physical properties of the final water-absorbing resin powder (2) are shown in Tables 1 and 2.

Production Example 2

The same operation as described in Production Example 1 was performed, except that the amount of polyethylene glycol diacrylate (average number of units: 9) in Production Example 1 was changed from 1.26 parts by weight to 0.84 parts by weight.

A belt-shaped crosslinked hydrogel polymer (b) obtained in Production Example 2 had a gel CRC of 31.1 g/g, a resin solid content of 52.1 weight %, a water-soluble component in an amount of 4.1 weight %, the water-soluble component having a weight average molecular weight of $25.8 \times 10^4$ Da, and a polymerization rate of 99.4 mol %.

Next, the belt-shaped crosslinked hydrogel polymer (b) was continuously cut, in the width direction relative to the traveling direction of the polymerization belt, into equal lengths of about 300 mm. In this way, a cut hydrogel polymer (b) was obtained.

Comparative Example 2

The same operation as described in Comparative Example 1 was performed using the cut hydrogel (b) obtained in Production Example 2.

It is noted, however, that the mesh size of the JIS standard sieve used after the pulverization of the dried polymer was changed from 710 μm to 850 μm and ethylene carbonate in the covalently bonding surface-crosslinking agent was changed to 1,3-propanediol.

It is noted that, in Comparative Example 2, gel grinding energy (GGE) was 12.9 J/g and gel grinding energy (2) (GGE(2)) was 11.8 J/g. Furthermore, a comparative particulate hydrogel (2) had a gel CRC of 31.5 g/g, a resin solid content of 50.9 weight %, a water-soluble component in an amount of 4.8 weight %, the water-soluble component having a weight average molecular weight of $28.0 \times 10^4$ Da, a weight average particle diameter (D50) of 850 μm, and a particle size distribution with a logarithmic standard deviation (σζ) of 0.96.

Furthermore, comparative water-absorbing resin powder (B2) obtained in Comparative Example 2 had a weight average particle diameter (D50) of 440 μm, a particle size distribution with a logarithmic standard deviation (σζ) of 0.36, a CRC of 37.1 g/g, a water-soluble component in an amount of 9.3 weight %, and 150 μm passable particles (percentage of water-absorbing resin powder passable through a sieve having a mesh size of 150 μm) in an amount of 0.4 weight %.

Physical properties of the final comparative water-absorbing resin powder (2) are shown in Tables 1 and 2.

Example 3

The same operation as described in Comparative Example 2 was performed, except that a silica dispersion was used in place of the hot water (90° C.) added during the gel-crushing in Comparative Example 2 and the amount of the dispersion added was 1.23 g/second. It is noted that the silica dispersion was a solution obtained by dispersing 11.84 weight % of Reolosil QS-20 (amorphous silica; available from Tokuyama Corporation) in deionized water and had a temperature adjusted to 90° C. Furthermore, in regard to the amount (1.23 g/second) of the dispersion added, the silica solid content relative to the amount of a hydrogel was 0.15 weight % and the silica solid content relative to the solid content of the hydrogel was 0.29 weight %.

It is noted that, in Example 3, gel grinding energy (GGE) was 13.3 J/g and gel grinding energy (2) (GGE (2)) was 12.1 J/g. Furthermore, a particulate hydrogel (3) had a gel CRC of 31.4 g/g, a resin solid content of 51.0 weight %, a water-soluble component in an amount of 4.7 weight %, the water-soluble component having a weight average molecular weight of $28.2 \times 10^4$ Da, a weight average particle diameter (D50) of 830 μm, and a particle size distribution with a logarithmic standard deviation (σζ) of 0.96.

Furthermore, water-absorbing resin powder (B3) obtained in Example 3 had a weight average particle diameter (D50) of 439 μm, a particle size distribution with a logarithmic standard deviation (σζ) of 0.36, a CRC of 36.9 g/g, a water-soluble component in an amount of 9.1 weight %, and 150 μm passable particles (percentage of water-absorbing resin powder passable through a sieve having a mesh size of 150 μm) in an amount of 0.3 weight %.

Physical properties of the final water-absorbing resin powder (3) are shown in Tables 1 and 2.

Example 4

The same operation as described in Comparative Example 2 was performed, except that a hydrotalcite dispersion was used in place of the hot water (90° C.) added during the gel-crushing in Comparative Example 2 and the amount of the dispersion added was 1.23 g/second. It is noted that the hydrotalcite dispersion was a solution obtained by dispersing 11.84 weight % of hydrotalcite (product name: DHT-6, available from Kyowa Chemical Industry Co., Ltd., $Mg_6Al_2(OH)_{16}CO_3 \cdot 4H_2O$ [x=0.25 and m=0.50 in General Formula (1)], volume average particle diameter 0.5 μm) in deionized water and had a temperature adjusted to 90° C. Furthermore, in regard to the amount (1.23 g/second) of the dispersion added, the hydrotalcite solid content relative to the amount of a hydrogel was 0.15 weight % and the hydrotalcite solid content relative to the solid content of the hydrogel was 0.29 weight %.

It is noted that, in Example 4, gel grinding energy (GGE) was 13.2 J/g and gel grinding energy (2) (GGE (2)) was 12.1 J/g. Furthermore, a particulate hydrogel (4) had a gel CRC of 31.4 g/g, a resin solid content of 51.0 weight %, a water-soluble component in an amount of 4.6 weight %, the water-soluble component having a weight average molecular weight of $28.1 \times 10^4$ Da, a weight average particle diameter (D50) of 833 μm, and a particle size distribution with a logarithmic standard deviation (σζ) of 0.96.

Furthermore, water-absorbing resin powder (B4) obtained in Example 4 had a weight average particle diameter (D50) of 439 μm, a particle size distribution with a logarithmic standard deviation (σζ) of 0.36, a CRC of 36.8 g/g, a water-soluble component in an amount of 9.2 weight %, and 150 μm passable particles (percentage of water-absorbing resin powder passable through a sieve having a mesh size of 150 μm) in an amount of 0.3 weight %.

Physical properties of the final water-absorbing resin powder (4) are shown in Tables 1 and 2.

TABLE 1

| | Inorganic compound | Amount added [wt %] | CRC [g/g] | AAP [g/g] | SFC [(1)] | FSR [g/(g·s)] | Vortex [seconds] | Internal gas bubble ratio [%] | Gel particle's collapse rate at swelling [wt %] | Shape retention capacity of gel particles |
|---|---|---|---|---|---|---|---|---|---|---|
| Comparative Exapmle 1 | None | — | 27.0 | 23.4 | 135 | 0.34 | 35 | 1.8 | 10.2 | Good |
| Exapmle 1 | Silica | 0.15 | 27.1 | 23.9 | 146 | 0.39 | 28 | 1.8 | 8.8 | Excellent |
| Exapmle 2 | Hydrotalcite | 0.15 | 27.0 | 24.0 | 145 | 0.38 | 29 | 1.7 | 8.7 | Excellent |

TABLE 1-continued

|  | Inorganic compound | Amount added [wt %] | CRC [g/g] | AAP [g/g] | SFC [(1)] | FSR [g/(g · s)] | Vortex [seconds] | Internal gas bubble ratio [%] | Gel particle's collapse rate at swelling [wt %] | Shape retention capacity of gel particles |
|---|---|---|---|---|---|---|---|---|---|---|
| Comparative Exapmle 2 | None | — | 30.0 | 24.0 | 40 | 0.30 | 40 | 1.8 | 10.1 | Good |
| Exapmle 3 | Silica | 0.15 | 30.1 | 24.6 | 52 | 0.34 | 35 | 1.7 | 8.9 | Excellent |
| Exapmle 4 | Hydrotalcite | 0.15 | 30.0 | 24.6 | 51 | 0.34 | 35 | 1.8 | 8.8 | Excellent |

(1)SFC[×10$^{-7}$ · cm$^3$ · s · g$^{-1}$]

TABLE 2

|  |  | Comparative Exapmle 1 | Exapmle 1 | Exapmle 2 | Comparative Exapmle 2 | Exapmle 3 | Exapmle 4 |
|---|---|---|---|---|---|---|---|
| Percentage of water-absorbing resin powder having a particle size of 150 μm or more and less than 850 μm | [wt %] | 98.6 | 98.7 | 98.7 | 99.6 | 99.7 | 99.7 |
| Percentage of water-absorbing resin powder having a particle size less than 150 μm | [wt %] | 1.4 | 1.3 | 1.3 | 0.4 | 0.3 | 0.3 |
| Particle size distribution |  | 0.0 | 0.0 | 0.0 | 1.9 | 1.9 | 1.8 |
| 710 μm or more and less than 850 μm | [wt %] |  |  |  |  |  |  |
| 600 μm or more and less than 710 μm | [wt %] | 2.1 | 2.2 | 2.1 | 15.2 | 15.1 | 15.2 |
| 500 μm or more and less than 600 μm | [wt %] | 11.1 | 11.2 | 11.2 | 20.3 | 20.1 | 20.4 |
| 300 μm or more and less than 500 μm | [wt %] | 60.6 | 60.4 | 60.6 | 45.1 | 45.4 | 45.3 |
| 150 μm or more and less than 300 μm | [wt %] | 24.8 | 24.9 | 24.8 | 17.1 | 17.2 | 17.0 |
| less than 150 μm | [wt %] | 1.4 | 1.3 | 1.3 | 0.4 | 0.3 | 0.3 |

(Recap)

As demonstrated by the above Examples and Comparative Examples and as shown in Table 1, in Examples in which an inorganic compound was added in the gel-crushing step, the obtained water-absorbing resin powder had an excellent fluid retention capacity under pressure (AAP), an excellent liquid permeability (SFC), an excellent water absorption speed (FSR), a short water absorption time (Vortex), and a low particle's collapse rate as compared to Comparative Examples in which no inorganic compound was added. In addition, the water-absorbing resin powder having a low gel particle's collapse rate at swelling is also excellent in shape retention capacity when swelling to become gel particles and therefore is expected to improve comfortability of absorbent articles such as disposable diapers.

Production Example 3

In a reactor formed by attaching a lid to a dual-arm type stainless steel kneader having a capacity of 10 liters and equipped with two sigma-type blades and a jacket, 430.6 g of acrylic acid, 4106.5 g of a 37 weight % aqueous sodium acrylate solution, 403.8 g of pure water, and 10.42 g (0.09 mol %) of polyethylene glycol diacrylate (molecular weight: 523) were fed and mixed to obtain an aqueous monomer solution (c).

Next, the aqueous monomer solution (c) was degassed in a nitrogen gas atmosphere for 20 minutes. Then, 26.56 g of a 10 weight % aqueous sodium persulfate solution and 22.13 g of a 0.1 weight % aqueous L-ascorbic acid solution were added to the aqueous monomer solution (c) with stirring. This initiated polymerization after about 34 seconds. The polymerization was performed at a polymerization temperature in a range of 25° C. to 92° C. Thirty minutes after the start of the polymerization, a crosslinked hydrogel polymer (c) was removed from the reactor.

It is noted that, as the polymerization progresses, the aqueous monomer solution (c) is polymerized to become the crosslinked hydrogel polymer (c). In this process, the generated crosslinked hydrogel polymer (c) was subjected to gel-crushing by the kneader to be grain-refined to a particle diameter of about 5 mm or less.

Next, the grain-refined crosslinked hydrogel polymer (c) was spread on a 50-mesh wire gauze (through-flow plate) (mesh size: 300 μm), and was dried by passing hot air of 180° C. through the plate for 50 minutes and thereby the particulate crosslinked hydrogel polymer (c) was dried. In this way, a dried polymer (c) was obtained. The hot air was passed upward in perpendicular to the through-flow plate and the gel layer and the average air velocity of the hot air was 1.0 m/s. The air velocity of the hot air was measured with the use of a constant temperature thermal anemometer Anemomaster 6162 (available from Kanomax Japan Inc.).

Next, the entire dried polymer (c) was pulverized (pulverization step) with the use of a roll mill, and then classified (classification step) with the use of JIS standard sieves JIS Z 8801-1(2000)) having mesh sizes of 710 μm and 175 μm. The particles that passed though the JIS standard sieve having a mesh size of 175 μm obtained in the above operation were used as water-absorbing resin fine particles (c).

Example 5

In a reactor formed by attaching a lid to a dual-arm type stainless steel kneader having a capacity of 10 liters and equipped with two sigma-type blades and a jacket, 430.6 g of acrylic acid, 4106.5 g of a 37 weight % aqueous sodium acrylate solution, 403.8 g of pure water, and 10.42 g (0.09 mol %) of polyethylene glycol diacrylate (molecular weight: 523) were fed and mixed to obtain an aqueous monomer solution (5).

Next, the aqueous monomer solution (5) was degassed in a nitrogen gas atmosphere for 20 minutes. Then, 26.56 g of a 10 weight % aqueous sodium persulfate solution and 22.13 g of a 0.1 weight % aqueous L-ascorbic acid solution were added to the aqueous monomer solution (c) with stirring. This initiated polymerization after about seconds. The polymerization was performed at a polymerization temperature in a range of 25° C. to 92° C. Twenty minutes after the start of the polymerization, 195 g of the water-absorbing resin fine particles (c) obtained in Production Example 3 were added. Ten minutes after that, a crosslinked hydrogel polymer (5) was removed from the reactor.

It is noted that, as the polymerization progresses, the aqueous monomer solution (5) is polymerized to become the crosslinked hydrogel polymer (5). In this process, the generated crosslinked hydrogel polymer (5) was subjected to the first gel-crushing by the kneader to be grain-refined to a particle diameter of about 5 mm or less.

Next, the crosslinked hydrogel polymer (5) obtained in the above operation was fed into a gel-crusher and was subjected to the second gel-crushing. The gel-crusher had, at an end thereof, a porous plate having a diameter of 100 mm, a thickness of 10 mm, and 80 pores in 6.4 mm diameter. It is noted that, in this gel-crushing, gel grinding energy (GGE) was 29.1 J/g and gel grinding energy (2) (GGE (2)) was 26.8 J/g. This gel-crushing was performed to give a particulate crosslinked hydrogel polymer (5).

Next, the particulate crosslinked hydrogel polymer (5) was spread on a 50-mesh wire gauze (through-flow plate) (mesh size: 300 μm), and was dried by passing hot air of 180° C. through the plate for 50 minutes and thereby the particulate crosslinked hydrogel polymer (5) was dried. In this way, a dried polymer (5) was obtained. The hot air was passed upward in perpendicular to the through-flow plate and the gel layer and the average air velocity of the hot air was 1.0 m/s. The air velocity of the hot air was measured with the use of a constant temperature thermal anemometer Anemomaster 6162 (manufactured by Kanomax Japan Inc.).

Next, the entire dried polymer (5) was pulverized (pulverization step) with the use of a roll mill, and then classified (classification step) with the use of JIS standard sieves (JIS Z 8801-1(2000)) having mesh sizes of 710 μm and 175 μm. In this way, water-absorbing resin powder (B5) ground to have an uneven shape having a particle diameter of 175 μm or more and less than 710 μm was obtained.

Next, 3.9 parts by weight of a covalently bonding surface-crosslinking agent solution composed of 0.3 parts by weight of ethylene carbonate, 0.6 parts by weight of propylene glycol, and 3.0 parts by weight of deionized water was added to 100 parts by weight of the water-absorbing resin powder (B5) and mixed until uniformity was obtained. In this way, a humidified mixture (5) was obtained. After that, the humidified mixture (5) was treated with heat at 208° C. for about 40 minutes so that the resultant water-absorbing resin powder (P5) would have a CRC of 26.6 g/g to 27.4 g/g. In this way, the water-absorbing resin powder (P5) was obtained.

After that, the water-absorbing resin powder (P5) was cooled, and an ionic bonding surface-crosslinking agent solution composed of 1.17 parts by weight of a 27.5 weight % aqueous aluminum sulfate solution (8 weight % in aluminum oxide equivalent), 0.196 parts by weight of a 60 weight % aqueous sodium lactate solution, and 0.029 parts by weight of propylene glycol was added to the water-absorbing resin powder (P5) and mixed until uniformity was obtained. In this way, a product (5) was obtained.

After that, the product (5) was crushed (sizing step) until the product (5) became able to pass through a JIS standard sieve having a mesh size of 710 μm. In this way, water-absorbing resin powder (5) was obtained. Physical properties of the water-absorbing resin powder (5) are shown in Table 3.

Example 6

The same operation as described in Example 5 was performed, except that the porous plate of the gel-crusher in Example 5 was changed to a porous plate having a diameter of 100 mm, a thickness of 10 mm, and 18 pores in 12.5 mm diameter. Physical properties of the final water-absorbing resin powder (6) are shown in Table 3. In Example 6, gel grinding energy (GGE) was 20.4 J/g and gel grinding energy (2) (GGE (2)) was 18.7 J/g.

Comparative Example 3

The same operation as described in Example 5 was performed, except that the porous plate of the gel-crusher in Example 5 was changed to a porous plate having a diameter of 100 mm, a thickness of 10 mm, and 12 pores in 4.8 mm diameter. Physical properties of the final comparative water-absorbing resin powder (3) are shown in Table 3. In Comparative Example 3, gel grinding energy (GGE) was 40.0 J/g and gel grinding energy (2) (GGE (2)) was 37.0 J/g.

TABLE 3

| | CRC [g/g] | AAP [g/g] | SFC [(1)] | FSR [g/ (g · s)] | Vortex [seconds] | Internal gas bubble ratio [%] | Gel particle's collapse rate at swelling [wt %] | Shape retention capacity of gel particles |
|---|---|---|---|---|---|---|---|---|
| Exapmle 5 | 27.4 | 24.5 | 116 | 0.40 | 26 | 1.2 | 9.7 | Good |
| Exapmle 6 | 27.3 | 24.3 | 128 | 0.35 | 34 | 1.1 | 6.0 | Excellent |
| Comparative Exapmle 3 | 27.2 | 24.1 | 103 | 0.34 | 35 | 1.0 | 11.0 | Poor |

(1)SFC[×10$^{-7}$ · cm$^3$ · s · g$^{-1}$]

TABLE 4

| | | Exapmle 5 | Exapmle 6 | Comparative Exapmle 3 |
|---|---|---|---|---|
| Percentage of water-absorbing resin powder having a particle size of 150 μm or more and less than 850 μm | [wt %] | 98.4 | 98.8 | 98.7 |
| Percentage of water-absorbing resin powder having a particle size of less than 150 μm | [wt %] | 1.6 | 1.2 | 1.3 |
| Particle size distribution | | | | |
| 710 μm or more and less than 850 μm | [wt %] | 0.0 | 0.0 | 0.0 |

TABLE 4-continued

|  |  | Example 5 | Example 6 | Comparative Example 3 |
|---|---|---|---|---|
| 600 μm or more and less than 710 μm | [wt %] | 2.0 | 2.3 | 2.1 |
| 500 μm or more and less than 600 μm | [wt %] | 11.0 | 11.2 | 11.1 |
| 300 μm or more and less than 500 μm | [wt %] | 60.4 | 60.5 | 60.4 |
| 150 μm or more and less than 300 μm | [wt %] | 25.0 | 24.8 | 25.1 |
| less than 150 μm | [wt %] | 1.6 | 1.2 | 1.3 |

(Recap)

As demonstrated by the above Examples and Comparative Examples, Examples of the present invention provided water-absorbing resin powders having an excellent fluid retention capacity under pressure (AAP), an excellent liquid permeability (SFC), and a low particle's collapse rate as compared to Comparative Examples.

Furthermore, as shown in Tables 1 and 3 presented above, it was confirmed that the evaluation method of an embodiment of the present invention makes it possible to measure the gel particle's collapse rate at swelling as an example of the degree of collapse of swollen gel particles when water-absorbing resin powder swells to become the swollen gel particles. It was also confirmed that a low gel particle's collapse rate at swelling provides a high liquid permeability. In addition, water-absorbing resin powder having a low gel particle's collapse rate at swelling has an excellent shape retention capacity when swelling to become gel particles and is expected to improve conformability of absorbent articles such as disposable diapers.

INDUSTRIAL APPLICABILITY

Water-absorbing resin powder in accordance with an embodiment of the present invention is excellent especially in fluid retention capacity under pressure, water absorption speed, and liquid permeability, and therefore takes up liquid well and thus reduces liquid leakage and seeping-out of the absorbed liquid when used in a water absorbent core of an absorbent article such as a disposable diaper.

An evaluation method in accordance with an embodiment of the present invention is capable of evaluating the degree of collapse of swollen gel particles when water-absorbing resin powder has swollen to become the swollen gel particles. Furthermore, an embodiment of the present invention enables an advanced product design. For example, the degree of collapse of swollen gel particles may be used as an indicator to design a water-absorbing resin having a specific function.

Therefore, water-absorbing resin powder in accordance with an embodiment of the present invention is useful in absorbent articles such as disposable diapers, sanitary napkins, and blood absorbers for medical use. The water-absorbing resin powder may also be used in various applications such as animal urine absorbents, urine gelling agents for portable toilets, freshness keeping agents for green groceries and the like, drip absorbers for meat and marine products, ice packs, disposable body warmers, gelling agents for batteries, water retention agents for plants and soil and the like, dew condensation preventing agents, water blocking agents, packing agents, and artificial snow.

REFERENCE SIGNS LIST

30 Tray
31 Spread region
32 Water-absorbing resin powder
33 Top sheet
34 Wire gauze
35 Inlet
36 Top cover
37 Weight
200 Gel particle's shape retention capacity measuring instrument

The invention claimed is:

1. Polyacrylic acid (salt)-based water-absorbing resin powder comprising a polyacrylic acid (salt) as a main component, wherein some particles of said polyacrylic acid (salt)-based water-absorbing resin powder include an inorganic compound internally present therein, said polyacrylic acid (salt)-based water-absorbing resin powder satisfying the following physical properties (1) to (4):
  (1) a water absorption time according to a vortex method (Vortex) is 42 seconds or less or a free swell rate (FSR) is 0.28 g/(g·s) or more;
  (2) a percentage of water-absorbing resin powder having a particle size of 150 μm or more and less than 850 μm is 90 weight % or more;
  (3) a gel particle's collapse rate at swelling is 10 weight % or less;
  (4) an internal gas bubble ratio defined by the following equation is 0.1% to 2.5%:

Internal gas bubble ratio (%)=(true density−apparent density)/true density×100.

2. The polyacrylic acid (salt)-based water-absorbing resin powder according to claim 1, further satisfying any one or more of the following physical properties (5) to (9):
  (5) a fluid retention capacity under pressure (AAP) is 20 g/g or more;
  (6) a saline flow conductivity (SFC) is $10 \times 10^{-7}$·cm$^3$·s·g$^{-1}$ or more;
  (7) a percentage of water-absorbing resin powder having a particle size less than 150 μm is 5 weight % or less;
  (8) a percentage of water-absorbing resin powder having a particle size of 850 μm or more is 5 weight % or less; and
  (9) a centrifuge retention capacity (CRC) is 10 g/g or more.

3. The polyacrylic acid (salt)-based water-absorbing resin powder according to claim 1, wherein said polyacrylic acid (salt)-based water-absorbing resin powder is surface-cross-linked with a covalently bonding surface-crosslinking agent.

4. The polyacrylic acid (salt)-based water-absorbing resin powder according to claim 1, wherein said inorganic compound is in the form of inorganic particles, the inorganic particles being a polyvalent metal salt.

* * * * *